US012570597B2

(12) United States Patent
Xie et al.

(10) Patent No.: US 12,570,597 B2
(45) Date of Patent: Mar. 10, 2026

(54) POLYARYL CARBOXYLIC FULLERENE DERIVATIVE AND USE THEREOF IN ANTI-CORONAVIRUS INFECTION

(71) Applicants: XIAMEN UNIVERSITY, Xiamen (CN); XIAMEN FUNANO NEW MATERIAL TECHNOLOGY CO., LTD., Xiamen (CN)

(72) Inventors: Suyuan Xie, Xiamen (CN); Changfeng Zhu, Xiamen (CN); Qianyan Zhang, Xiamen (CN); Lansun Zheng, Xiamen (CN); Piaoyang Xu, Xiamen (CN); Tongzong Yang, Xiamen (CN); Linlong Deng, Xiamen (CN); Yuanzhi Tan, Xiamen (CN); Sheng Zhu, Xiamen (CN)

(73) Assignees: XIAMEN UNIVERSITY, Xiamen (CN); XIAMEN FUNANO NEW MATERIAL TECHNOLOGY CO., LTD., Xiamen (CN)

( * ) Notice: Subject to any disclaimer, the term of this patent is extended or adjusted under 35 U.S.C. 154(b) by 440 days.

(21) Appl. No.: 18/020,648

(22) PCT Filed: Aug. 9, 2021

(86) PCT No.: PCT/CN2021/111449

§ 371 (c)(1),
(2) Date: Feb. 10, 2023

(87) PCT Pub. No.: WO2022/033417

PCT Pub. Date: Feb. 17, 2022

(65) Prior Publication Data

US 2023/0348354 A1 Nov. 2, 2023

(30) Foreign Application Priority Data

Aug. 11, 2020 (CN) ........................ 202010803038.8

(51) Int. Cl.
*C07C 57/50* (2006.01)
*A61K 9/1272* (2025.01)
(Continued)

(52) U.S. Cl.
CPC ............ *C07C 57/50* (2013.01); *A61K 9/1272* (2013.01); *A61K 9/1277* (2013.01); *A61P 31/14* (2018.01); *C07C 2604/00* (2017.05)

(58) Field of Classification Search
CPC ..... C07C 57/50; C07C 2604/00; C07C 57/62; A61K 9/1272; A61K 9/1277;
(Continued)

(56) References Cited

U.S. PATENT DOCUMENTS 10,934,168 B1 * 3/2021 Brady .................. D06M 16/00
2009/0118527 A1 * 5/2009 Nakamura .............. C07F 17/02 977/734

FOREIGN PATENT DOCUMENTS

CN 106083626 A * 11/2016
CN 110078616 A * 8/2019 ........... C06B 23/006
(Continued)

OTHER PUBLICATIONS

English Translation of RU 2567299 C2. Originally published in Russian on Nov. 10, 2015. 16 printed pages. (Year: 2015).*
(Continued)

*Primary Examiner* — Daniel C. McCracken
(74) *Attorney, Agent, or Firm* — Bayramoglu Law Offices LLC

(57) ABSTRACT

A polyaryl carboxylic fullerene derivative and its use in anti-coronavirus infection are disclosed. Specifically, a compound shown in formula A: fullerene-$RR_1R_2R_3R_4R_5$ formula A, or a stereoisomer, prodrug, pharmaceutically acceptable salt, or pharmaceutically acceptable solvate of the compound is provided. The compound or a derivative
(Continued)

thereof has promising application prospects in anti-coronavirus infection.

20 Claims, 13 Drawing Sheets

(51) Int. Cl.
*A61K 9/1277* (2025.01)
*A61P 31/14* (2006.01)

(58) Field of Classification Search
CPC ........ A61K 31/194; A61P 31/14; A61P 11/00; C01B 32/15; C01B 32/18; C01B 32/152; C01B 32/154; C01B 32/156
See application file for complete search history.

(56) References Cited

FOREIGN PATENT DOCUMENTS

| | | | |
|---|---|---|---|
| CN | 110876757 | A | 3/2020 |
| RU | 2012129528 | A | 1/2014 |
| RU | 2567299 | C2 * | 11/2015 |

OTHER PUBLICATIONS

English Translation of CN 110078616 A. Originally published in Chinese on Aug. 2, 2019. 5 printed pages. (Year: 2019).*

English Translation of CN 106083626 A. Originally published in Chinese on Nov. 9, 2016. 13 printed pages. (Year: 2016).*

Kraevaya, et al., Diversion of the Arbuzov reaction: alkylation of C-CI instead of phosphonic ester formation on the fullerene cage, Org. Biomol Chem. 2019; 17: 7155-7160 (Year: 2019).*

Huang, et al., Fullerene Derivatives as Lung Cancer Cell Inhibitors: Investigation of Potential Descriptors Using QSAR Approaches, International Journal of Nanomedicine 2020; 15: 2485-2499 (Year: 2020).*

Kobzar, et al., Polycarboxylic fullerene derivatives as protein tyrosine phosphatase inhibitors, Mendeleev Commun. 2005; 25: 199-201 (Year: 2005).*

Smolina, et al., Influence of water-soluble derivatives of [60]fullerene on catalytic activity of monoamine oxidase B and their membranotropic properties, Russian Chemical Bulletin, International Edition 2016; 65(3): 784-789 (Year: 2016).*

Troshina, et al., Chlorofullerene C60CI6: a precursor for straightforward preparation of highly water-soluble polycarboxylic fullerene derivatives active against HIV, Org. Biomol. Chem. 2007; 5: 2783-2791 (Year: 2007).*

Kotelnikova, et al., Influence of water-soluble derivatives of [60]fullerene on therapeutically important targets related to neurogedenerative diseases, Medicinal Chemistry Communications DOI: 10.1039/x0xx00000x pp. 1-5 (2013) (Year: 2013).*

English Translation of the Written Opinion of the International Searching Authority in PCT/CN2021/111449 dated Oct. 29, 2021 (Year: 2021).*

Hung-Jin Huang, et al., Fullerene Derivatives as Lung Cancer Cell Inhibitors: Investigation of Potential Descriptors Using QSAR Approaches, International Journal of Nanomedicine, 2020, pp. 2485-2499, vol. 15 No. 1.

Olga A. Kraevaya, et al., Direct arylation of C60CI6 and C70CI8 with carboxylic acids: a synthetic avenue to water-soluble fullerene derivatives with promising antiviral activity, Chemical Communications, 2019, pp. 1179-1182, vol. 56 No. 8.

Olga A. Kraevaya, et al., Diversion of the Arbuzov reaction: alkylation of C-CI instead of phosphonic ester formation on the fullerene cage, Organic & Biomolecular Chemistry, 2019, pp. 7155-7160.

Diagnosis and Treatment Protocol for Novel Coronavirus Pneumonia, National Health Commission & State Administration of Traditional Chinese Medicine, 2020, Trial Version 7.

* cited by examiner

POLYARYL CARBOXYLIC FULLERENE DERIVATIVE AND USE THEREOF IN ANTI-CORONAVIRUS INFECTION

CROSS REFERENCE TO THE RELATED APPLICATIONS

This application is the national phase entry of International Application No. PCT/CN2021/111449, filed on Aug. 9, 2021, which is based upon and claims priority to Chinese Patent Application No. 202010803038.8, filed on Aug. 11, 2020, the entire contents of which are incorporated herein by reference.

TECHNICAL FIELD

The present disclosure relates to the field of pharmaceutical chemistry, particularly to a polyaryl carboxylic fullerene derivative and its use in anti-coronavirus infection.

BACKGROUND

Coronaviruses are from the Coronaviridae family of the Nidovirales order. Coronaviruses are a large class of viruses widely present in nature, which can infect vertebrates such as humans, rats, pigs, cats, dogs, wolves, chickens, cattle, and poultry and can cause a variety of acute and chronic diseases. In 2019, a novel coronavirus was discovered and officially named SARS-CoV-2 by the International Committee on Taxonomy of Viruses (ICTV), which is a 0-coronavirus and an RNA virus. SARS-CoV-2 has an envelope, and SARS-CoV-2 virions are round or oval and often polymorphic and have a diameter of 60 nm to 140 nm. SARS-CoV-2 has a similar structure to SARS coronavirus (SARS-CoV) and Middle East respiratory syndrome coronavirus (MERS-CoV) but has clearly different genetic traits. SARS-CoV-2 is the seventh member of the Coronaviridae family that infects humans. On Feb. 11, 2020, the 2019 novel coronavirus (2019-nCoV) was named COVID-19 by the World Health Organization (WHO). The disease caused by the virus SARS-CoV-2 is more contagious than the disease caused by SARS-CoV. On Mar. 11, 2020, the WHO declared that the COVID-19 outbreak could be regarded as a global pandemic.

In response to COVID-19 caused by SARS-CoV-2, scientists around the world have been actively looking for specific drugs. According to the "*Diagnosis and Treatment Plan for COVID*-19 (Trial Revised Version 7)" issued by the Chinese government on Mar. 4, 2020, the recommended treatment methods for COVID-19 include the administration of a lopinavir/ritonavir compound in combination with ribavirin, a biologic interferon-α nebulizer, chloroquine phosphate, and arbidol, and a number of traditional Chinese medicine (TCM) formulas and prescriptions for symptomatic treatment of COVID-19. According to reports inside and outside China, in clinical practice, the anti-influenza drug oseltamivir and the anti-Ebola virus candidate remdesivir exhibit a therapeutic effect for COVID-19 in certain cases. In addition, the anti-acquired immunodeficiency syndrome (AIDS) drug darunavir and the anti-influenza drug favipiravir have been shown to be effective in treating COVID-19 during in vitro studies.

However, it should be particularly noted that there is still a lack of effective antiviral drugs for treating COVID-19 so far. Therefore, antiviral drugs for treating COVID-19 need to be further developed.

SUMMARY

An objective of the present disclosure is to provide a water-soluble polyaryl carboxylic fullerene derivative and its use in the preparation of a drug for preventing or treating a coronavirus. The inventors evaluate the antiviral activity of the polyaryl carboxylic fullerene derivative using models infected by an rVSV-SARS2 pseudovirus and a SARS-CoV-2 envirus, and evaluation results show that the polyaryl carboxylic fullerene derivative can effectively inhibit the infection of the rVSV-SARS2 pseudovirus and SARS-CoV-2 envirus for cells.

Further, the inventors have discovered that the polyaryl carboxylic fullerene derivative can effectively inhibit a coronavirus.

In view of this, in a first aspect of the present disclosure, the present disclosure provides a compound of the following general formula:

fullerene-$RR_1R_2R_3R_4R_5$ formula A or a stereoisomer, prodrug, pharmaceutically acceptable salt, or pharmaceutically acceptable solvate of the compound, where the fullerene is a cage-like all-carbon structure composed of a five-membered carbon ring and a six-membered carbon ring;

R is selected from the group consisting of the following:

(2) H, F, Cl, Br, I, $C_1$-$C_6$ alkyl, and $C_1$-$C_6$ alkoxy; and (2)

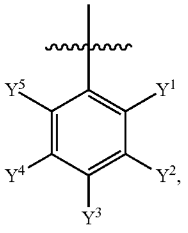

where $Y^1$, $Y^2$, $Y^3$, $Y^4$, and $Y^5$ are not all H and each are independently selected from the group consisting of the following:

2) H;

2)

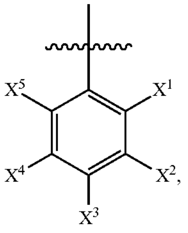

where $X^1$, $X^2$, $X^3$, $X^4$, and $X^5$ each are independently selected from the group consisting of H and $C_1$-$C_6$ alkyl substituted with 1, 2, or 3 carboxyl groups, and $X^1$, $X^2$, $X^3$, $X^4$, and $X^5$ are not all H; and (3)

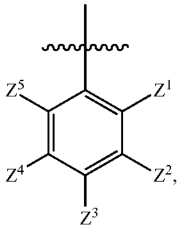

where $Z^1$, $Z^2$, $Z^3$, $Z^4$, and $Z^5$ each are independently selected from the group consisting of H and $C_1$-$C_6$ alkyl substituted with 1, 2, or 3 carboxyl groups, and $Z^1$, $Z^2$, $Z^3$, $Z^4$, and $Z^5$ are not all H; and $R^1$, $R^2$, $R^3$, $R^4$, and $R^5$ each are independently selected from the group consisting of the following:

(1)

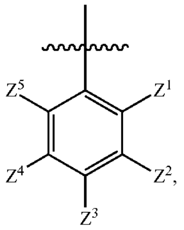

where $Z^1$, $Z^2$, $Z^3$, $Z^4$, and $Z^5$ each are independently selected from the group consisting of H and $C_1$-$C_6$ alkyl substituted with 1, 2, or 3 carboxyl groups, and $Z^1$, $Z^2$, $Z^3$, $Z^4$, and $Z^5$ are not all H; and (2)

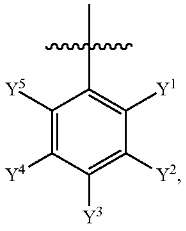

where $Y^1$, $Y^2$, $Y^3$, $Y^4$, and $Y^5$ are not all H and each are independently selected from the group consisting of the following:

2)

H; and

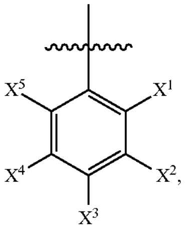

where $X^1$, $X^2$, $X^3$, $X^4$, and $X^5$ each are independently selected from the group consisting of H and $C_1$-$C_6$ alkyl substituted with 1, 2, or 3 carboxyl groups, and $X^1$, $X^2$, $X^3$, $X^4$, and $X^5$ are not all H.

Compounds shown in formula A do not include the following compounds:

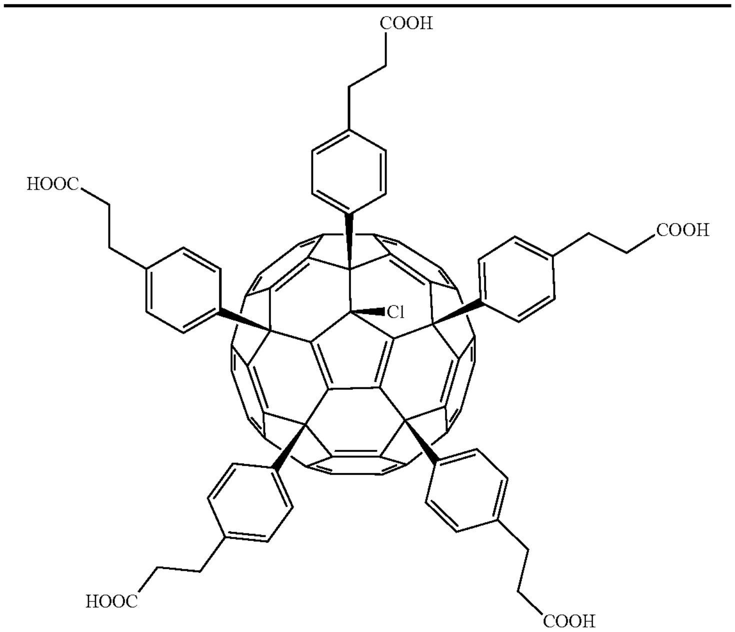
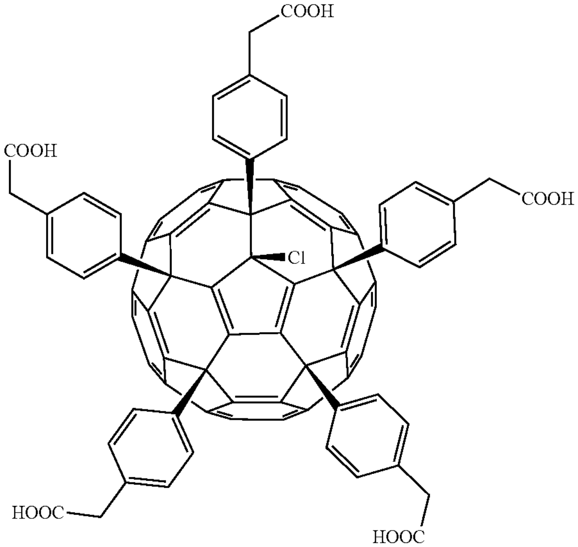
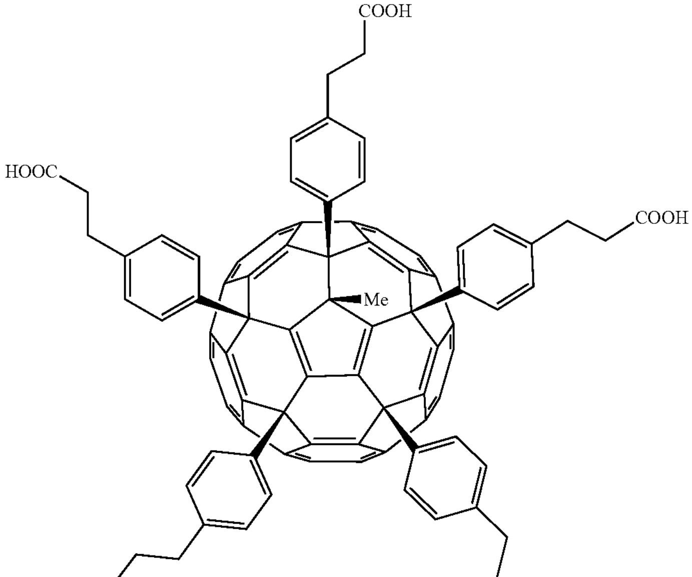

It should be noted that the structural formula "fullerene-$RR_1R_2R_3R_4R_5$" shown in formula A means that 6 atoms or groups linked to the fullerene are substituted with R, $R_1$, $R_2$, $R_3$, $R_4$, and $R_5$, respectively.

In some embodiments, the fullerene further includes a seven-membered carbon ring and/or a four-membered carbon ring.

In some embodiments, the fullerene is selected from the group consisting of $C_{60}$, $C_{70}$, $C_{84}$, $C_{90}$, and $C_{100}$.

In some embodiments, the fullerene is a hollow cage-like structure or a metal or cluster-embedded structure.

In some embodiments, the fullerene is $C_{60}$, and the fullerene is a hollow cage-like structure.

In some embodiments, the compound is a compound of the following general formula:

formula I

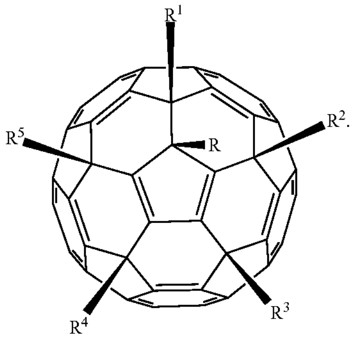

where

R is selected from the group consisting of the following:

(2) H, F, Cl, Br, I, $C_1$-$C_6$ alkyl, and $C_1$-$C_6$ alkoxy, preferably F, Cl, Br, I, and $C_1$-$C_4$ alkyl, more preferably Cl and methyl, and most preferably Cl; and (2)

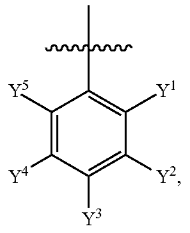

where $Y^1$, $Y^2$, $Y^3$, $Y^4$, and $Y^5$ are not all H and each are independently selected from the group consisting of the following:

1) H;

2)

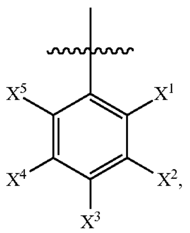

where $X^1$, $X^2$, $X^3$, $X^4$, and $X^5$ each are independently selected from the group consisting of H and $C_1$-$C_6$ alkyl substituted with 1, 2, or 3 carboxyl groups, and $X^1$, $X^2$, $X^3$, $X^4$, and $X^5$ are not all H; and (3)

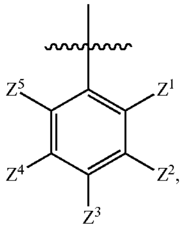

where $Z^1$, $Z^2$, $Z^3$, $Z^4$, and $Z^5$ each are independently selected from the group consisting of H and $C_1$-$C_6$ alkyl substituted with 1, 2, or 3 carboxyl groups, and $Z^1$, $Z^2$, $Z^3$, $Z^4$, and $Z^5$ are not all H.

$R^1$, $R^2$, $R^3$, $R^4$, and $R^5$ each are independently selected from the group consisting of the following:

(1)

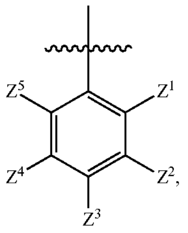

where $Z^1$, $Z^2$, $Z^3$, $Z^4$, and $Z^5$ each are independently selected from the group consisting of H and $C_1$-$C_6$ alkyl substituted with 1, 2, or 3 carboxyl groups, and $Z^1$, $Z^2$, $Z^3$, $Z^4$, and $Z^5$ are not all H; and (2)

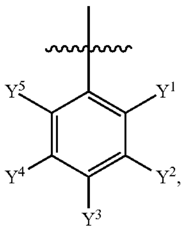

where $Y^1$, $Y^2$, $Y^3$, $Y^4$, and $Y^5$ are not all H and each are independently selected from the group consisting of the following:

1) H, and

2)

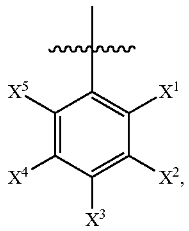
where
$X^1$, $X^2$, $X^3$, $X^4$, and $X^5$ each are independently selected from the group consisting of H and $C_1$-$C_6$ alkyl substituted with 1, 2, or 3 carboxyl groups, and $X^1$, $X^2$, $X^3$, $X^4$, and $X^5$ are not all H.
Compounds shown in formula I do not include the following compounds:
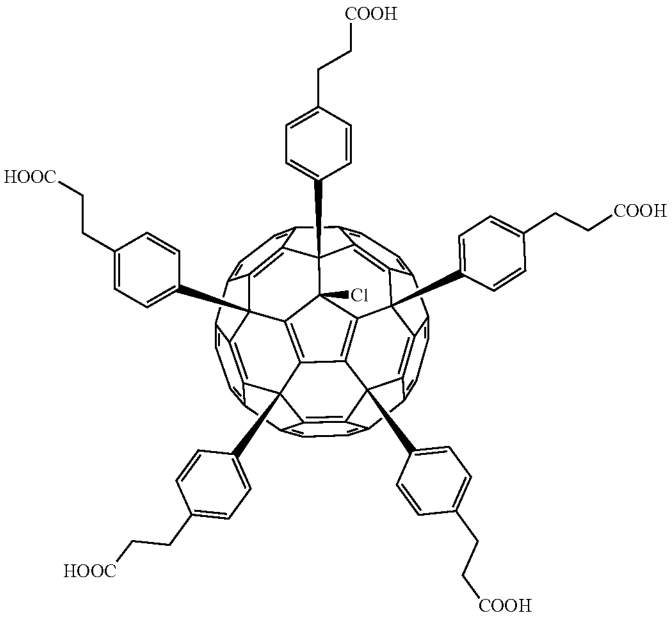
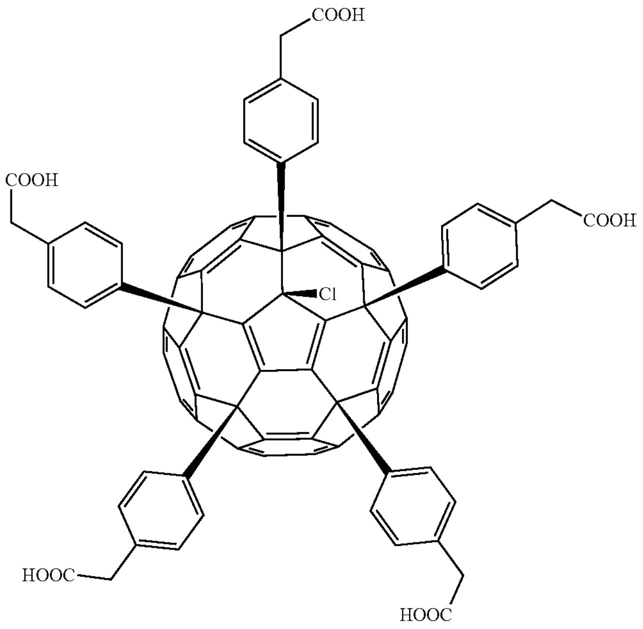

-continued
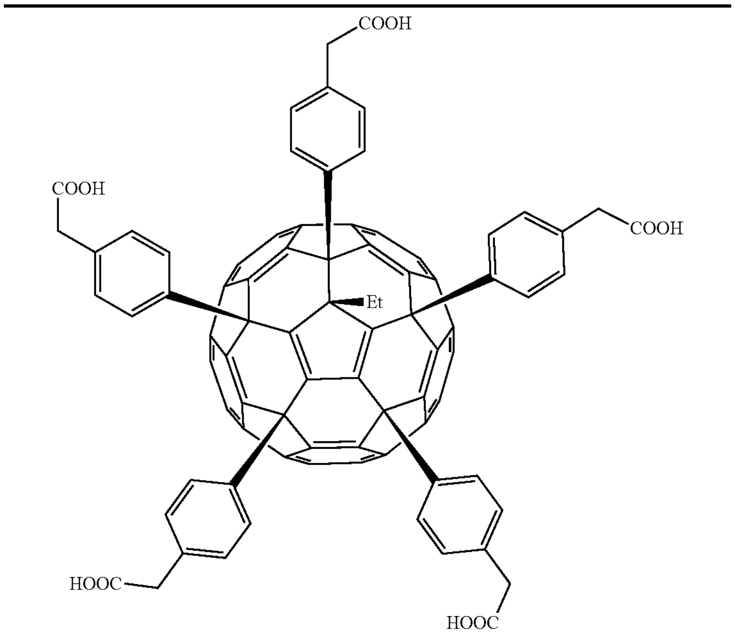
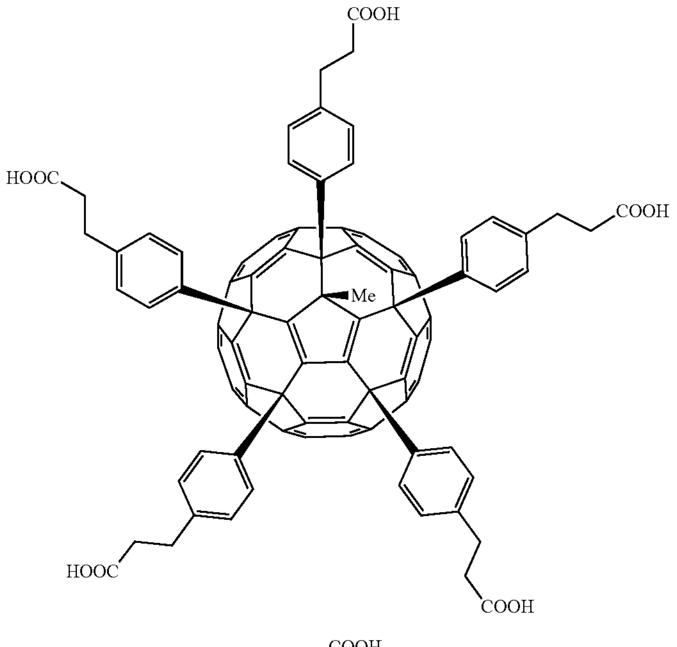
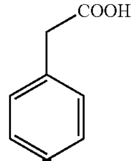

It should be noted that, in a compound shown in formula I, R, $R^1$, Rz, $R^3$, $R^4$, and $R^5$ are only present in half of the fullerene $C_{60}$ framework and are not present in the other half.

In some specific embodiments, in the definition of R, $X^1$, $X^2$, $X^3$, $X^4$, and $X^5$ each are independently selected from the group consisting of H and $C_1$-$C_6$ alkyl substituted with 1 carboxyl group, and $X^1$, $X^2$, $X^3$, $X^4$, and $X^5$ are not all H.

In some specific embodiments, in the definition of R, $X^1$, $X^2$, $X^3$, $X^4$, and $X^5$ each are independently selected from the group consisting of H and $C_2$-$C_6$ alkyl substituted with 1 carboxyl group, and $X^1$, $X^2$, $X^3$, $X^4$, and $X^5$ are not all H.

In some specific embodiments, in the definition of R, $X^1$, $X^2$, $X^3$, $X^4$, and $X^5$ each are independently selected from the group consisting of H and

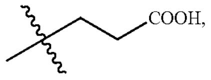 [SMILES: *CCC(=O)O]

and $X^1$, $X^2$, $X^3$, $X^4$, and $X^5$ are not all H.

In some specific embodiments, in the definition of R, $Z^1$, $Z^2$, $Z^3$, $Z^4$, and $Z^5$ each are independently selected from the group consisting of H and $C_1$-$C_6$ alkyl substituted with 1 carboxyl group, and $Z^1$, $Z^2$, $Z^3$, $Z^4$, and $Z^5$ are not all H.

In some embodiments, R is selected from the group consisting of the following:

(2) H, F, Cl, Br, I, $C_1$-$C_6$ alkyl, and $C_1$-$C_6$ alkoxy, preferably F, Cl, Br, I, and $C_1$-$C_4$ alkyl, more preferably Cl and methyl, and most preferably Cl; and (2)

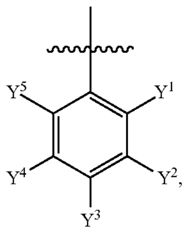

where $Y^1$, $Y^2$, $Y^3$, $Y^4$, and $Y^5$ are not all H and each are independently selected from the group consisting of the following:

1) H, and

2)

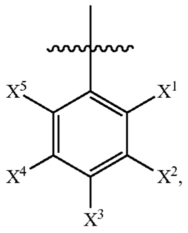

where $X^1$, $X^2$, $X^3$, $X^4$, and $X^5$ each are independently selected from the group consisting of H and $C_1$-$C_6$ alkyl substituted with 1, 2, or 3 carboxyl groups, and $X^1$, $X^2$, $X^3$, $X^4$, and $X^5$ are not all H.

In some specific embodiments, in the definition of R, $X^1$, $X^2$, $X^3$, $X^4$, and $X^5$ each are independently selected from the group consisting of H and $C_1$-$C_6$ alkyl substituted with 1 carboxyl group, and $X^1$, $X^2$, $X^3$, $X^4$, and $X^5$ are not all H.

In some specific embodiments, in the definition of R, $X^1$, $X^2$, $X^3$, $X^4$, and $X^5$ each are independently selected from the group consisting of H and $C_2$-$C_6$ alkyl substituted with 1 carboxyl group, and $X^1$, $X^2$, $X^3$, $X^4$, and $X^5$ are not all H.

In some specific embodiments, in the definition of R, $X^1$, $X^2$, $X^3$, $X^4$, and $X^5$ each are independently selected from the group consisting of H and

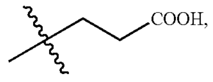 [SMILES: *CCC(=O)O]

and $X^1$, $X^2$, $X^3$, $X^4$, and $X^5$ are not all H.

In some specific embodiments, in the definitions of $R^1$, $R^2$, $R^3$, $R^4$, and $R^5$, $Z^1$, $Z^2$, $Z^3$, $Z^4$, and $Z^5$ each are independently selected from the group consisting of H and $C_1$-$C_6$ alkyl substituted with 1 carboxyl group, and $Z^1$, $Z^2$, $Z^3$, $Z^4$, and $Z^5$ are not all H.

In some specific embodiments, in the definitions of $R^1$, $R^2$, $R^3$, $R^4$, and $R^5$, $Z^1$, $Z^2$, $Z^3$, $Z^4$ and $Z^5$ each are independently selected from the group consisting of H,

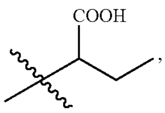
,
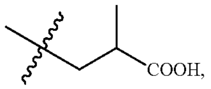

isopropyl substituted with 1 carboxyl, n-butyl substituted with 1 carboxyl, isobutyl substituted with 1 carboxyl, and tert-butyl substituted with 1 carboxyl, and $Z^1$, $Z^2$, $Z^3$, $Z^4$, and $Z^5$ are not all H.

In some specific embodiments, in the definitions of $R^1$, $R^2$, $R^3$, $R^4$, and $R^5$, $Z^1$, $Z^2$, $Z^3$, $Z^4$, and $Z^5$ each are independently selected from the group consisting of H,

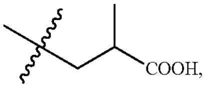
and
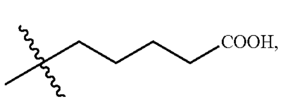

and $Z^1$, $Z^2$, $Z^3$, $Z^4$, and $Z^5$ are not all H.

In some specific embodiments, in the definitions of $R^1$, $R^2$, $R^3$, $R^4$, and $R^5$, $X^1$, $X^2$, $X^3$, $X^4$, and $X^5$ each are independently selected from the group consisting of H and $C_1$-$C_6$ alkyl substituted with 1 carboxyl, and $X^1$, $X^2$, $X^3$, $X^4$, and $X^5$ are not all H.

In some specific embodiments, in the definitions of $R^1$, $R^2$, $R^3$, $R^4$, and $R^5$, $X^1$, $X^2$, $X^3$, $X^4$, and $X^5$ each are independently selected from the group consisting of H and $C_2$-$C_6$ alkyl substituted with 1 carboxyl group, and $X^1$, $X^2$, $X^3$, $X^4$, and $X^5$ are not all H.

In some specific embodiments, in the definitions of $R^1$, $R^2$, $R^3$, $R^4$, and $R^5$, $X^1$, $X^2$, $X^3$, $X^4$, and $X^5$ each are independently selected from the group consisting of H and

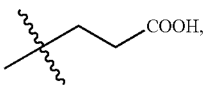 [SMILES: *CCC(=O)O]

and $X^1$, $X^2$, $X^3$, $X^4$, and $X^5$ are not all H.

In some embodiments, R is selected from the group consisting of the following:

(1) H, F, Cl, Br, I, $C_1$-$C_6$ alkyl, and $C_1$-$C_6$ alkoxy, preferably F, Cl, Br, I, and $C_1$-$C_4$ alkyl, more preferably Cl and methyl, and most preferably Cl; and (2)

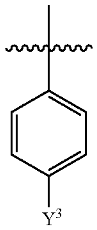

, where

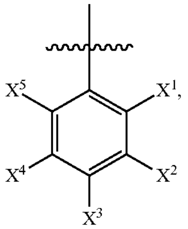

where $X^1$, $X^2$, $X^3$, $X^4$, and $X^5$ each are independently selected from the group consisting of H and $C_1$-$C_6$ alkyl substituted with 1, 2, or 3 carboxyl groups, and $X^1$, $X^2$, $X^3$, $X^4$, and $X^5$ are not all H.

In some specific embodiments, $X^1$, $X^2$, $X^3$, $X^4$, and $X^5$ each are independently selected from the group consisting of H and $C_1$-$C_6$ alkyl substituted with 1 carboxyl group, and $X^1$, $X^2$, $X^3$, $X^4$, and $X^5$ are not all H.

In some specific embodiments, $X^1$, $X^2$, $X^3$, $X^4$, and $X^5$ each are independently selected from the group consisting of H and $C_2$-$C_6$ alkyl substituted with 1 carboxyl group, and $X^1$, $X^2$, $X^3$, $X^4$, and $X^5$ are not all H.

In some specific embodiments $X^1$, $X^2$, $X^3$, $X^4$, and $X^5$ each are independently selected from the group consisting of H and

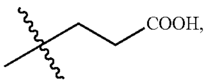 [SMILES: *CCC(=O)O]

and $X^1$, $X^2$, $X^3$, $X^4$, and $X^5$ are not all H.

In some specific embodiments, $Y^3$ is

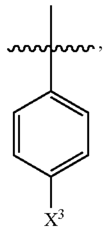

where $X^3$ is $C_1$-$C_6$ alkyl substituted with 1, 2, or 3 carboxyl groups. In some preferred specific embodiments, $X^3$ is $C_1$-$C_6$ alkyl substituted with 1 carboxyl group. In some preferred specific embodiments, $X^3$ is $C_2$-$C_6$ alkyl substituted with 1 carboxyl group. In some preferred specific embodiments, $X^3$ is

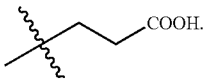 [SMILES: *CCC(=O)O]

In some embodiments, $R^1$, $R^2$, $R^3$, $R^4$, and $R^5$ each are independently selected from the group consisting of the following:

(1)

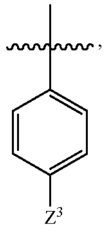

where $Z^3$ is independently $C_1$-$C_6$ alkyl substituted with 1, 2, or 3 carboxyl groups; and (2)

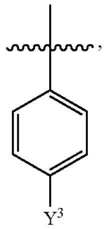

where $Y^3$ is

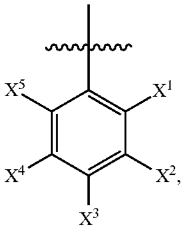

where $X^1$, $X^2$, $X^3$, $X^4$, and $X^5$ each are independently selected from the group consisting of H and $C_1$-$C_6$ alkyl substituted with 1, 2, or 3 carboxyl groups, and $X^1$, $X^2$, $X^3$, $X^4$, and $X^5$ are not all H.

In some specific embodiments, $Z^3$ is independently $C_1$-$C_6$ alkyl substituted with 1 carboxyl group.

Tn some specific embodiments, $Z^3$ is independently selected from the group consisting of

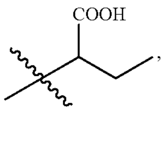

,

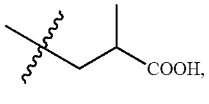

isopropyl substituted with 1 carboxyl group, n-butyl substituted with 1 carboxyl group, isobutyl substituted with 1 carboxyl group, and tert-butyl substituted with 1 carboxyl group.

In some specific embodiments $Z^3$ is independently selected from the group consisting of

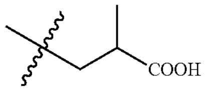 and 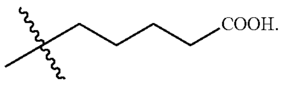

In some specific embodiments, $X^1$, $X^2$, $X^3$, $X^4$, and $X^5$ each are independently selected from the group consisting of H and $C_1$-$C_6$ alkyl substituted with 1 carboxyl group, and $X^1$, $X^2$, $X^3$, $X^4$, and $X^5$ are not all H.

In some specific embodiments, $X^1$, $X^2$, $X^3$, $X^4$, and $X^5$ each are independently selected from the group consisting of H and $C_2$-$C_6$ alkyl substituted with 1 carboxyl group, and $X^1$, $X^2$, $X^3$, $X^4$, and $X^5$ are not all H.

In some specific embodiments, $X^1$, $X^2$, $X^3$, $X^4$, and $X^5$ each are independently selected from the group consisting of H and

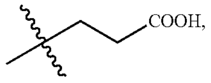 [SMILES: *CCC(=O)O]

$X^1$, $X^2$, $X^3$, $X^4$, and $X^5$ are not all H.

In some specific embodiments, $Y^3$ is

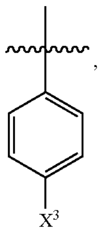

where $X^3$ is independently $C_1$-$C_6$ alkyl substituted with 1, 2, or 3 carboxyl groups. In some preferred specific embodiments, $X^3$ is independently $C_1$-$C_6$ alkyl substituted with 1 carboxyl group. In some preferred specific embodiments, $X^3$ is independently $C_2$-$C_6$ alkyl substituted with 1 carboxyl group. In some preferred specific embodiments, $X^3$ is

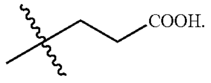 [SMILES: *CCC(=O)O]

In some embodiments, $R^1$, $R^2$, $R^3$, $R^4$, and $R^5$ each are:

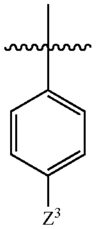 or 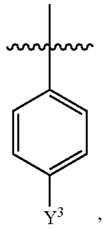 , where $Z^3$ is $C_1$-$C_6$ alkyl substituted with 1, 2, or 3 carboxyl groups; and $Y^3$ is

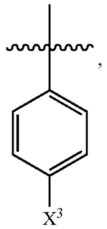

where $X^3$ is $C_1$-$C_6$ alkyl substituted with 1, 2, or 3 carboxyl groups.

In some specific embodiments, $Z^3$ is $C_1$-$C_6$ alkyl substituted with 1 carboxyl group.

In some specific embodiments, $Z^3$ is selected from the group consisting of

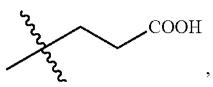 , 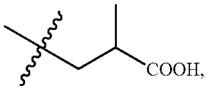

isopropyl substituted with 1 carboxyl group, n-butyl substituted with 1 carboxyl group, isobutyl substituted with 1 carboxyl group, and tert-butyl substituted with 1 carboxyl group.

In some specific embodiments, $Z^3$ is

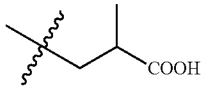 or 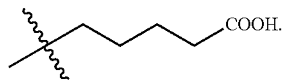

In some specific embodiments, $X^3$ is $C_1$-$C_6$ alkyl substituted with 1 carboxyl group.

In some specific embodiments, $X^3$ is $C_2$-$C_6$ alkyl substituted with 1 carboxyl group.

In some specific embodiments, $X^3$ is

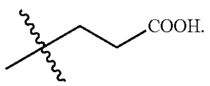 [SMILES: *CCC(=O)O]

In some embodiments, the compound is a compound selected from the group consisting of the following:

| Compound No. | Compound structure |
| --- | --- |
| 3 | 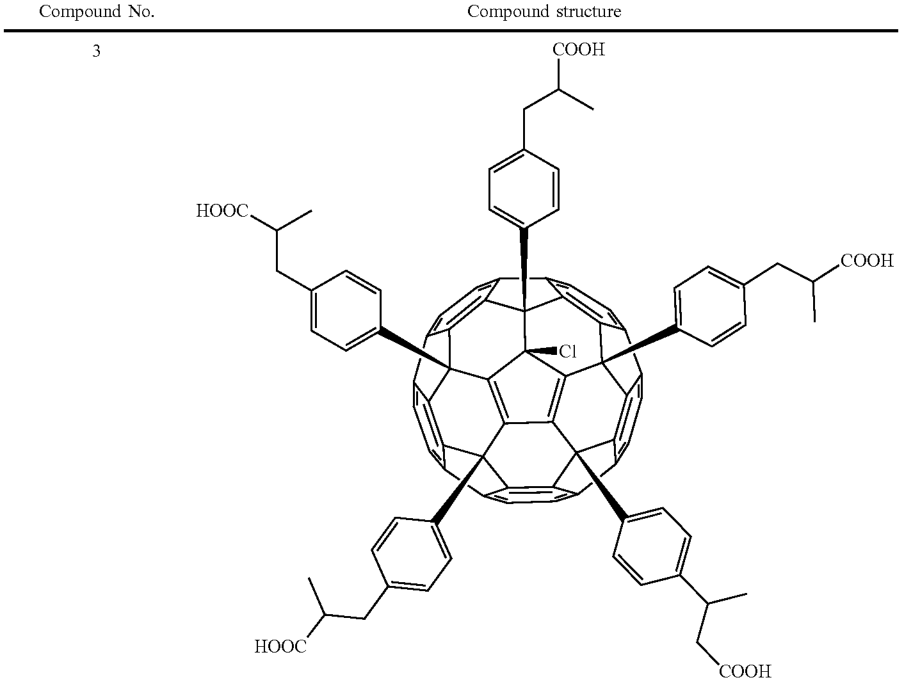 |
| 4 | 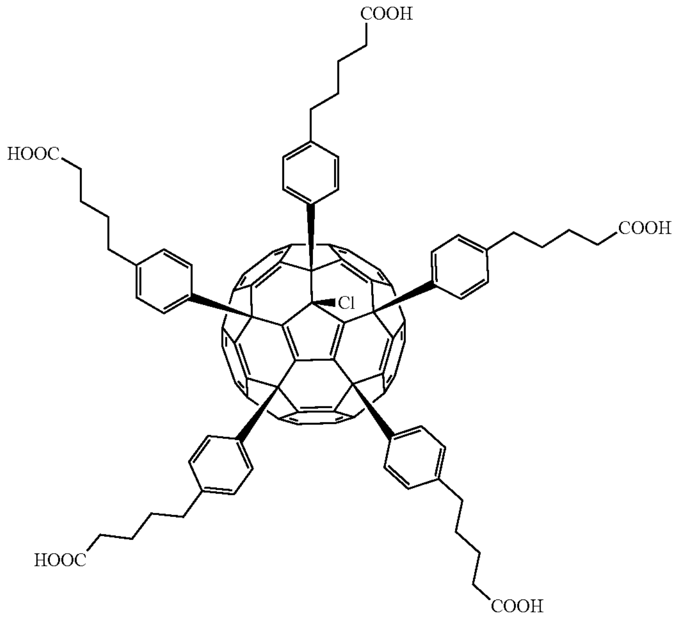 |
| 5 | 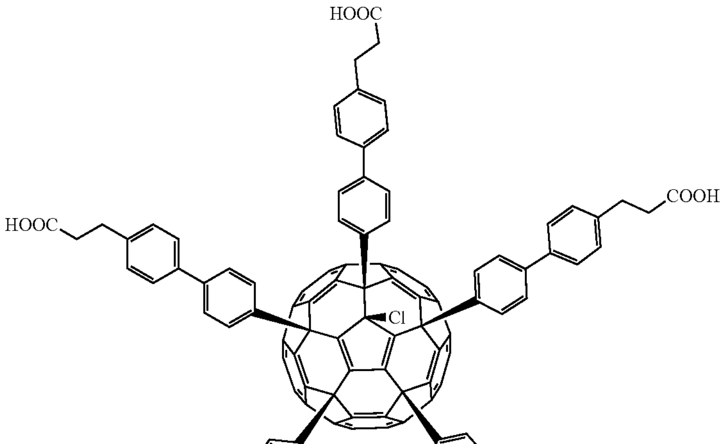 |

or a stereoisomer, prodrug, pharmaceutically acceptable salt, or pharmaceutically acceptable solvate of the compound.

In a second aspect of the present disclosure, the present disclosure provides a method for preparing the compound described above, including:

(1) subjecting $C_{60}Cl_6$ to a nucleophilic substitution reaction with α-methylhydrocinnamic acid, 5-phenylvaleric acid, or 3-(4-biphenyl)propionic acid to obtain the compound; or subjecting $C_{60}Cl_6$ to a nucleophilic substitution reaction with methyl 3-(4-biphenyl)propionate, and after the nucleophilic substitution reaction is complete, cooling the resulting reaction system to room temperature, and subjecting the product of the nucleophilic substitution reaction to a hydrolysis reaction to obtain the compound.

In some embodiments, a molar ratio of the α-methylhydrocinnamic acid, the 5-phenylvaleric acid, the methyl 3-(4-biphenyl)propionate, or the 3-(4-biphenyl)propionic acid to the $C_{60}Cl_6$ is (20-30):1 (such as 25:1).

In some embodiments, the nucleophilic substitution reaction is conducted in the presence of $SnCl_4$.

In some embodiments, the nucleophilic substitution reaction is conducted under water-free and oxygen-free conditions.

In some embodiments, a solvent for the nucleophilic substitution reaction is nitrobenzene.

In some embodiments, the nucleophilic substitution reaction is conducted at 60° C. to 100° C. (such as 80° C. or 90° C.) for 1 h to 3 h (such as 2 h).

In some embodiments, a solvent for the hydrolysis reaction is toluene.

In some embodiments, the hydrolysis reaction is conducted in the presence of acetic acid and hydrochloric acid.

In some embodiments, the hydrolysis reaction is conducted at 60° C. to 100° C. (such as 80° C.) for 60 h to 80 h (such as 70 h or 72 h).

In some embodiments, before the hydrolysis reaction, it further includes: subjecting the product of the nucleophilic substitution reaction to purification.

In some embodiments, the purification is conducted through column chromatography.

In some embodiments, a mobile phase for the column chromatography is toluene/methanol in a volume ratio of 85/15.

In some embodiments, the preparation method further includes:

(2) after the nucleophilic substitution reaction of the $C_{60}Cl_6$ with the α-methylhydrocinnamic acid, the 5-phenylvaleric acid, or the 3-(4-biphenyl)propionic acid in step (1) is complete, cooling the resulting reaction system to room temperature, adding acetonitrile to the reaction system for precipitation, and subjecting the resulting mixture to filtration (such as suction filtration) to obtain a first filter cake; or after the hydrolysis reaction in step (1) is complete, conducting extraction with toluene, rotary evaporation, adding acetonitrile to a reaction product obtained after the rotary evaporation for precipitation, and subjecting the resulting mixture to filtration (such as suction filtration) to obtain a first filter cake;

(3) dissolving the first filter cake with a potassium hydroxide solution, subjecting the resulting solution to filtration (such as suction filtration) to remove insoluble matters, and collecting a filtrate;

(4) adding hydrochloric acid dropwise to the filtrate for neutralization until the pH of the filtrate is 7.0, such that a precipitate is produced; and (5) subjecting the mixture obtained in step (4) to filtration (such as suction filtration) to obtain a second filter cake, which is the compound.

In some embodiments, after step (2) and before step (3), it further includes: washing (for example, washing with n-hexane three times) and drying the first filter cake.

In some embodiments, after step (5), it further includes: drying the second filter cake to obtain the compound.

In a third aspect of the present disclosure, the present disclosure provides a pharmaceutical composition including the compound described above or the stereoisomer, prodrug, pharmaceutically acceptable salt, or pharmaceutically acceptable solvate of the compound or or a compound prepared by the method described above, and an optional pharmaceutically acceptable carrier or excipient.

In some embodiments, the pharmaceutical composition is in a dosage form of a pill, a tablet, a capsule, an aqueous solution, or an aqueous suspension for oral administration, in a dosage form of a micronized suspension or solution for topical ocular administration, in a dosage form of a paste, an ointment, a lotion, a spray, or a cream for topical transdermal or mucosal administration, or in a dosage form of sterile injection water, an oil suspension, or a sterile injection solution for injection.

Some amphiphilic molecules, such as many naturally synthesized surfactants and phospholipids that cannot be simply associated into micelles, will spontaneously form a molecular ordered assembly with a closed bilayer structure when dispersed in water, and the assembly is called a vesicle. An important application of vesicles is to use vesicles as carriers for drugs. Compared with other microstructures, a vesicle has a peculiar structure including a hydrophobic microdomain and a hydrophobic microdomain, such that the vesicle can carry both a water-soluble drug and a water-insoluble drug. Since vesicles have a double-layer membrane structure and exhibit prominent compatibility with biological membranes, vesicles are ideal carriers for drugs in vivo. In addition, because it takes a long time for a molecule to enter and exit a vesicle, efforts have been made in recent years to use a vesicle as a sustained-release agent for achieving high efficacy.

The inventors have discovered that the compound shown in formula A or formula I or a pharmaceutically acceptable salt thereof is mostly present in a solution in the form of a vesicle (as shown in FIG. 1). Further, the inventors have discovered that the diameter of the vesicle of the present disclosure is comparable to the diameter of a coronavirus, and thus the inventors speculate that the vesicle may exert an antiviral effect to some extent by embedding a coronavirus.

In view of this, in a fourth aspect of the present disclosure, the present disclosure provides a vesicle with a diameter of 40 nm to 140 nm (such as 50 nm, 60 nm, 70 nm, 80 nm, 90 nm, 100 nm, 110 nm, 120 nm, or 130 nm), where the vesicle is produced using the compound or the pharmaceutically acceptable salt thereof described above. It should be noted that the diameter of the vesicle refers to an outer diameter, and the diameter of the vesicle is controllable.

In some embodiments, the vesicle is produced by the following method:

dissolving the compound or the pharmaceutically acceptable salt thereof described above in N,N-dimethylformamide (DMF) or acetonitrile to obtain a solution, and subjecting the solution to an ultrasonic treatment at 30° C. to 40° C. for 1 h to 2 h to obtain the vesicle. In some embodiments, a ratio of the mass of the compound or the pharmaceutically acceptable salt thereof to the volume of the DMF or the acetonitrile is 1 mg:1 mL.

In a fifth aspect of the present disclosure, the present disclosure provides a use of a compound shown in formula A or a stereoisomer, prodrug, pharmaceutically acceptable salt, or pharmaceutically acceptable solvate thereof in the preparation of a drug.

The drug is provided for preventing and/or treating a disease caused by a coronavirus (such as a novel coronavirus (SARS-CoV-2) or an rVSV-SARS2 pseudocoronavirus) infection, and preferably, the drug is provided for preventing and/or treating pneumonia caused by a coronavirus (such as a novel coronavirus (SARS-CoV-2) or an rVSV-SARS2 pseudocoronavirus) infection, such as pneumonia COVID-2019 caused by a SARS-CoV-2 infection (such as a respiratory disease, including, but not limited to, a simple infection such as fever, cough, and sore throat, pneumonia, an acute or severe acute respiratory infection, hypoxemic respiratory failure (HRF) and acute respiratory distress syndrome (ARDS), sepsis, and septic shock); or the drug is provided to serve as an inhibitor for a coronavirus (such as a novel coronavirus (SARS-CoV-2) or an rVSV-SARS2 pseudocoronavirus); or the drug is provided to inhibit the replication or reproduction of a coronavirus (such as a novel coronavirus (SARS-CoV-2) or an rVSV-SARS2 pseudocoronavirus) in a cell (such as a mammalian cell).

fullerene-$RR_1R_2R_3R_4R_5$ formula A where the fullerene is a cage-like all-carbon structure composed of a five-membered carbon ring and a six-membered carbon ring;

R is selected from the group consisting of the following:

(1) H, F, Cl, Br, I, $C_1$-$C_6$ alkyl, and $C_1$-$C_6$ alkoxy;

(2)

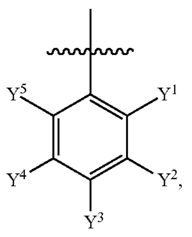

where $Y^1$, $Y^2$, $Y^3$, $Y^4$, and $Y^5$ are not all H and each are independently selected from the group consisting of the following:

1) H, and

2)

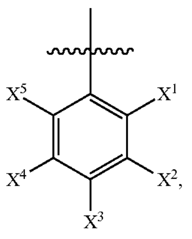

where $X^1$, $X^2$, $X^3$, $X^4$, and $X^5$ each are independently selected from the group consisting of H and $C_1$-$C_6$ alkyl substituted with 1, 2, or 3 carboxyl groups, and $X^1$, $X^2$, $X^3$, $X^4$, and $X^5$ are not all H; and (3)

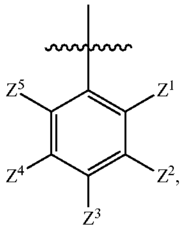

where $Z^1$, $Z^2$, $Z^3$, $Z^4$, and $Z^5$ each are independently selected from the group consisting of H and $C_1$-$C_6$ alkyl substituted with 1, 2, or 3 carboxyl groups, and $Z^1$, $Z^2$, $Z^3$, $Z^4$, and $Z^5$ are not all H; and $R^1$, $R^2$, $R^3$, $R^4$, and $R^5$ each are independently selected from the group consisting of the following:

(1)

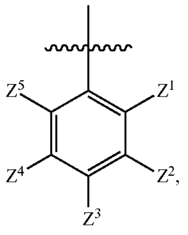

where $Z^1$, $Z^2$, $Z^3$, $Z^4$, and $Z^5$ each are independently selected from the group consisting of H and $C_1$-$C_6$ alkyl substituted with 1, 2, or 3 carboxyl groups, and $Z^1$, $Z^2$, $Z^3$, $Z^4$, and $Z^5$ are not all H; and (2)

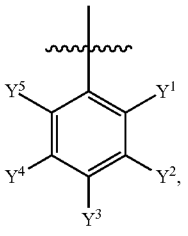

where $Y^1$, $Y^2$, $Y^3$, $Y^4$, and $Y^5$ are not all H and each are independently selected from the group consisting of the following:

1) H, and

2)

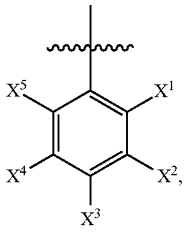

where $X^1$, $X^2$, $X^3$, $X^4$, and $X^5$ each are independently selected from the group consisting of H and $C_1$-$C_6$ alkyl substituted with 1, 2, or 3 carboxyl groups, and $X^1$, $X^2$, $X^3$, $X^4$, and $X^5$ are not all H.

In some embodiments, the fullerene further includes a seven-membered carbon ring and/or a four-membered carbon ring.

In some embodiments, the fullerene is selected from the group consisting of $C_{60}$, $C_{70}$, $C_{84}$, $C_{90}$, and $C_{100}$.

In some embodiments, the fullerene is a hollow cage-like structure or a metal or cluster-embedded structure.

In some embodiments, the fullerene is $C_{60}$, and the fullerene is a hollow cage-like structure.

In some embodiments, the compound is a compound of the following general formula:

formula I

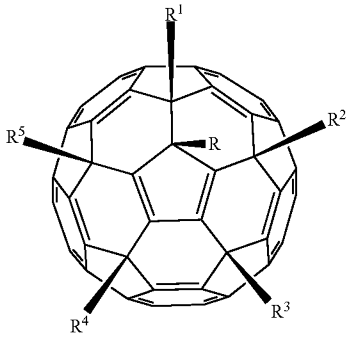

where

R is selected from the group consisting of the following:

(1) H, F, Cl, Br, I, $C_1$-$C_6$ alkyl, and $C_1$-$C_6$ alkoxy, preferably F, Cl, Br, I, and $C_1$-$C_4$ alkyl, and more preferably $C_1$ and methyl;

(2)

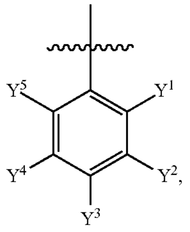

where $Y^1$, $Y^2$, $Y^3$, $Y^4$, and $Y^5$ are not all H and each are independently selected from the group consisting of the following:

1) H, and

2)

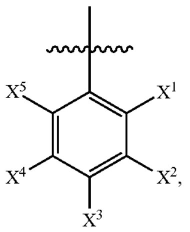

where $X^1$, $X^2$, $X^3$, $X^4$, and $X^5$ each are independently selected from the group consisting of H and $C_1$-$C_6$ alkyl substituted with 1, 2, or 3 carboxyl groups, and $X^1$, $X^2$, $X^3$, $X^4$, and $X^5$ are not all H; and (3)

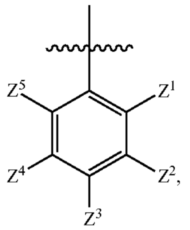

where $Z^1$, $Z^2$, $Z^3$, $Z^4$, and $Z^5$ each are independently selected from the group consisting of H and $C_1$-$C_6$ alkyl substituted with 1, 2, or 3 carboxyl groups, and $Z^1$, $Z^2$, $Z^3$, $Z^4$, and $Z^5$ are not all H; and $R^1$, $R^2$, $R^3$, $R^4$, and $R^5$ each are independently selected from the group consisting of the following:

(1)

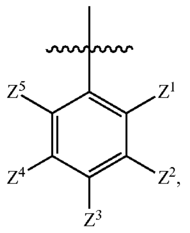

where $Z^1$, $Z^2$, $Z^3$, $Z^4$, and $Z^5$ each are independently selected from the group consisting of H and $C_1$-$C_6$ alkyl substituted with 1, 2, or 3 carboxyl groups, and $Z^1$, $Z^2$, $Z^3$, $Z^4$, and $Z^5$ are not all H; and (2),

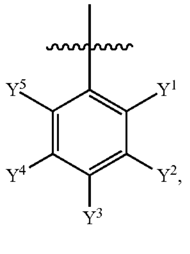

where $Y^1$, $Y^2$, $Y^3$, $Y^4$, and $Y^5$ are not all H and each are independently selected from the group consisting of the following:

1) H, and

2)

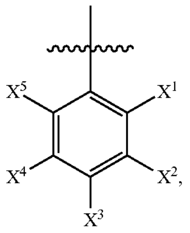

where $X^1$, $X^2$, $X^3$, $X^4$, and $X^5$ each are independently selected from the group consisting of H and $C_1$-$C_6$ alkyl substituted with 1, 2, or 3 carboxyl groups, and $X^1$, $X^2$, $X^3$, $X^4$, and $X^5$ are not all H.

In some specific embodiments, in the definition of R, $X^1$, $X^2$, $X^3$, $X^4$, and $X^5$ each are independently selected from the group consisting of H and $C_1$-$C_6$ alkyl substituted with 1 carboxyl group, and $X^1$, $X^2$, $X^3$, $X^4$, and $X^5$ are not all H.

In some specific embodiments, in the definition of R, $X^1$, $X^2$, $X^3$, $X^4$, and $X^5$ each are independently selected from the group consisting of H and

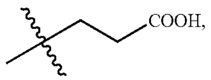

and $X^1$, $X^2$, $X^3$, $X^4$, and $X^5$ are not all H.

In some specific embodiments, in the definition of R, $Z^1$, $Z^2$, $Z^3$, $Z^4$, and $Z^5$ each are independently selected from the group consisting of H and $C_1$-$C_6$ alkyl substituted with 1 carboxyl group, and $Z^1$, $Z^2$, $Z^3$, $Z^4$, and $Z^5$ are not all H.

In some embodiments, R is selected from the group consisting of the following:

(1) H, F, Cl, Br, I, $C_1$-$C_6$ alkyl, and $C_1$-$C_6$ alkoxy, preferably F, Cl, Br, I, and $C_1$-$C_4$ alkyl, and more preferably Cl and methyl; and (2)

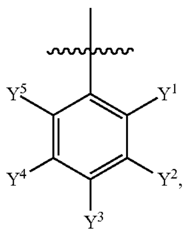

where $Y^1$, $Y^2$, $Y^3$, $Y^4$, and $Y^5$ are not all H and each are independently selected from the group consisting of the following:

1) H, and

2)

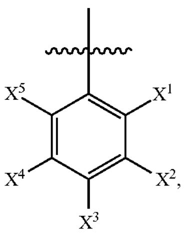

where $X^1$, $X^2$, $X^3$, $X^4$, and $X^5$ each are independently selected from the group consisting of H and $C_1$-$C_6$ alkyl substituted with 1, 2, or 3 carboxyl groups, and $X^1$, $X^2$, $X^3$, $X^4$, and $X^5$ are not all H.

In some specific embodiments, in the definition of R, $X^1$, $X^2$, $X^3$, $X^4$, and $X^5$ each are independently selected from the group consisting of H and $C_1$-$C_6$ alkyl substituted with 1 carboxyl group, and $X^1$, $X^2$, $X^3$, $X^4$, and $X^5$ are not all H.

In some specific embodiments, in the definition of R, $X^1$, $X^2$, $X^3$, $X^4$, and $X^5$ each are independently selected from the group consisting of H and

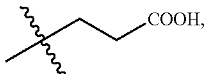 [SMILES: *CCC(=O)O]

and $X^1$, $X^2$, $X^3$, $X^4$, and $X^5$ are not all H.

In some specific embodiments, in the definitions of $R^1$, $R^2$, $R^3$, $R^4$, and $R^5$, $Z^1$, $Z^2$, $Z^3$, $Z^4$, and $Z^5$ each are independently selected from the group consisting of H and $C_1$-$C_6$ alkyl substituted with 1 carboxyl group, and $Z^1$, $Z^2$, $Z^3$, $Z^4$, and $Z^5$ are not all H.

In some specific embodiments, in the definitions of $R^1$, $R^2$, $R^3$, $R^4$, and $R^5$, $Z^1$, $Z^2$, $Z^3$, $Z^4$, and $Z^5$ each are independently selected from the group consisting of H,

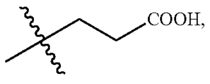 [SMILES: *CCC(=O)O] 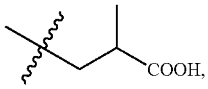 and

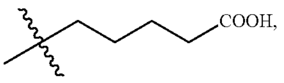

and $Z^5$ are not all H.

In some specific embodiments, in the definitions of $R^1$, $R^2$, $R^3$, $R^4$, and $R^5$, $X^1$, $X^2$, $X^3$, $X^4$, and $X^5$ each are independently selected from the group consisting of H and $C_1$-$C_6$ alkyl substituted with 1 carboxyl group, and $X^1$, $X^2$, $X^3$, $X^4$, and $X^5$ are not all H.

In some specific embodiments, in the definitions of $R^1$, $R^2$, $R^3$, $R^4$, and $R^5$, $X^1$, $X^2$, $X^3$, $X^4$, and $X^5$ each are independently selected from the group consisting of H and

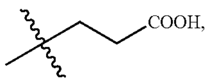

and $X^1$, $X^2$, $X^3$, $X^4$, and $X^5$ are not all H.

In some embodiments, R is selected from the group consisting of the following:

(1) H, F, Cl, Br, I, $C_1$-$C_6$ alkyl, and $C_1$-$C_6$ alkoxy, preferably F, Cl, Br, I, and $C_1$-$C_4$ alkyl, and more preferably Cl and methyl; and (2)

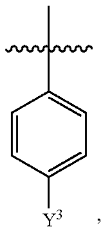

, where $Y^3$ is

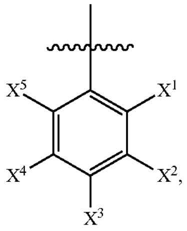

where $X^1$, $X^2$, $X^3$, $X^4$, and $X^5$ each are independently selected from the group consisting of H and $C_1$-$C_6$ alkyl substituted with 1, 2, or 3 carboxyl groups, and $X^1$, $X^2$, $X^3$, $X^4$, and $X^5$ are not all H.

In some specific embodiments, $X^1$, $X^2$, $X^3$, $X^4$, and $X^5$ each are independently selected from the group consisting of H and $C_1$-$C_6$ alkyl substituted with 1 carboxyl group, and $X^1$, $X^2$, $X^3$, $X^4$, and $X^5$ are not all H.

In some specific embodiments $X^1$, $X^2$, $X^3$, $X^4$, and $X^5$ each are independently selected from the group consisting of H and

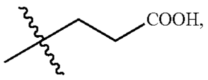 [SMILES: *CCC(=O)O]

$X^1$, $X^2$, $X^3$, $X^4$, and $X^5$ are not all H.

In some specific embodiments, $Y^3$ is

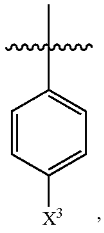

, where $X^3$ is $C_1$-$C_6$ alkyl substituted with 1, 2, or 3 carboxyl groups. In some preferred specific embodiments, $X^3$ is $C_1$-$C_6$ alkyl substituted with 1 carboxyl group. In some preferred specific embodiments, $X^3$ is

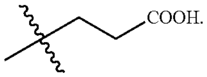

In some embodiments, $R^1$, $R^2$, $R^3$, $R^4$, and $R^5$ each are independently selected from the group consisting of the following:

(1)

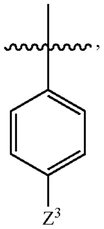

where $Z^3$ is independently $C_1$-$C_6$ alkyl substituted with 1, 2, or 3 carboxyl groups; and (2)

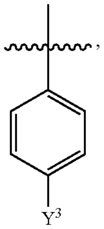

where $Y^3$ is

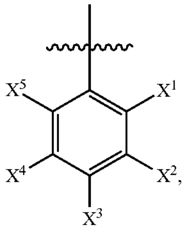

where $X^1$, $X^2$, $X^3$, $X^4$, and $X^5$ each are independently selected from the group consisting of H and $C_1$-$C_6$ alkyl substituted with 1, 2, or 3 carboxyl groups, and $X^1$, $X^2$, $X^3$, $X^4$, and $X^5$ are not all H.

In some specific embodiments, $Z^3$ is independently $C_1$-$C_6$ alkyl substituted with 1 carboxyl group.

Tn some specific embodiments, $Z^3$ is independently selected from the group consisting of

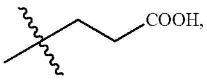 [SMILES: *CCC(=O)O]

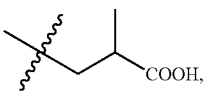

and

-continued

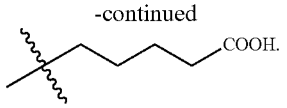

In some specific embodiments, $X^1$, $X^2$, $X^3$, $X^4$, and $X^5$ each are independently selected from the group consisting of H and $C_1$-$C_6$ alkyl substituted with 1 carboxyl group, and $X^1$, $X^2$, $X^3$, $X^4$, and $X^5$ are not all H.

In some specific embodiments, $X^1$, $X^2$, $X^3$, $X^4$, and $X^5$ each are independently selected from the group consisting of H and

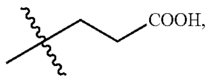 [SMILES: *CCC(=O)O]

and $X^1$, $X^2$, $X^3$, $X^4$, and $X^5$ are not all H.

In some specific embodiments, $Y^3$ is

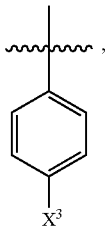

where $X^3$ is independently $C_1$-$C_6$ alkyl substituted with 1, 2, or 3 carboxyl groups. In some preferred specific embodiments, $X^3$ is independently $C_1$-$C_6$ alkyl substituted with 1 carboxyl group. In some preferred specific embodiments, $X^3$ is

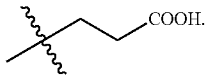 [SMILES: *CCC(=O)O]

In some embodiments, $R^1$, $R^2$, $R^3$, $R^4$, and $R^5$ each are:

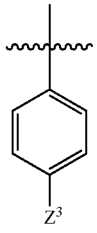

or

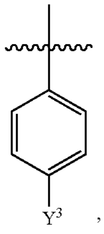

, where $Z^3$ is $C_{1-6}$ alkyl substituted with 1, 2, or 3 carboxyl groups; and $Y^3$ is

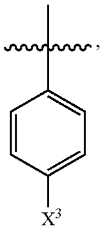

where $X^3$ is $C_1$-$C_6$ alkyl substituted with 1, 2, or 3 carboxyl groups.

In some specific embodiments, $Z^3$ is $C_1$-$C_6$ alkyl substituted with 1 carboxyl group.

In some specific embodiments, $Z^3$ is selected from the group consisting of

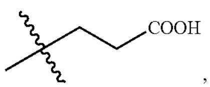

,

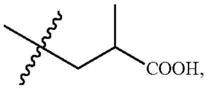

and

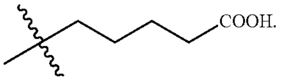

In some specific embodiments, $X^3$ is $C_1$-$C_6$ alkyl substituted with 1 carboxyl group.

In some specific embodiments, $X^3$ is

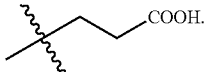 [SMILES: *CCC(=O)O]

In some embodiments, the compound shown in formula I is a compound selected from the group consisting of the following.

| Compound No. | Compound structure |
| --- | --- |
| 1 | 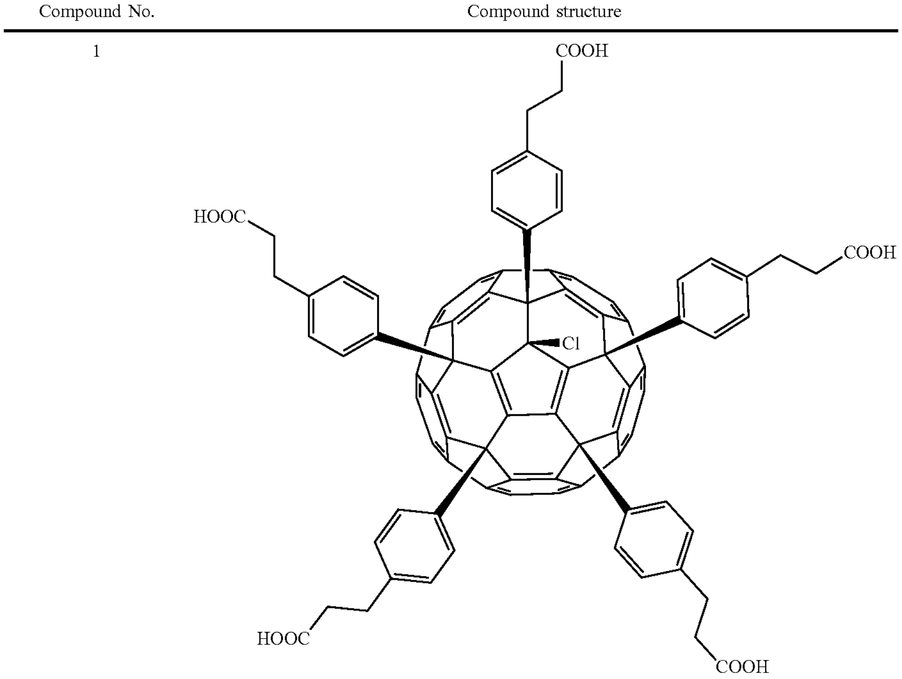 |
| 2 | 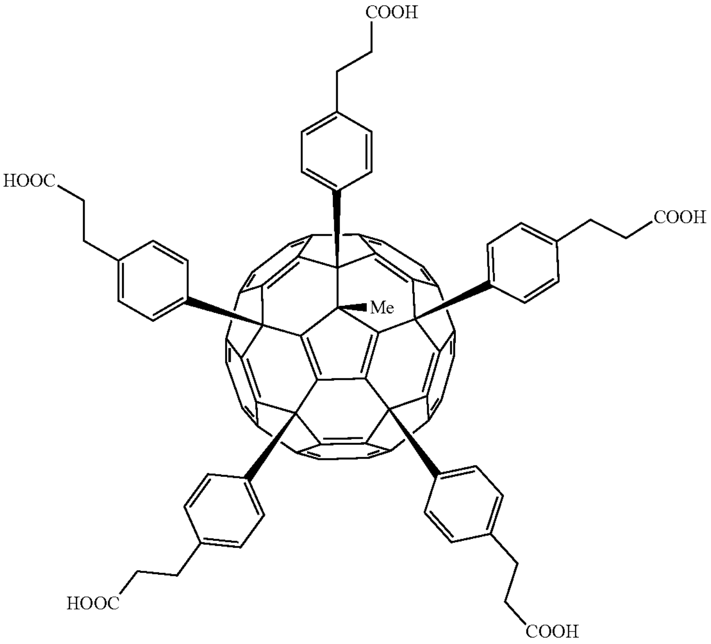 |
| 3 | 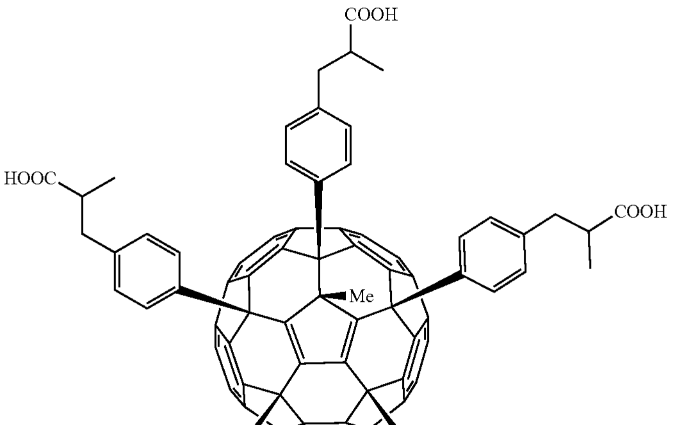 |

In a sixth aspect of the present disclosure, the present disclosure provides a use of a pharmaceutical composition or a vesicle in the preparation of a drug, where the pharmaceutical composition includes the compound shown in formula A or formula I or the stereoisomer, prodrug, pharmaceutically acceptable salt, or pharmaceutically acceptable solvate thereof described above or a compound prepared by the method described above and an optional pharmaceutically acceptable carrier or excipient; the vesicle has a diameter of 40 nm to 140 nm (such as 50 nm, 60 nm, or 70 nm) and is produced using the compound shown in formula A or formula I or the pharmaceutically acceptable salt thereof described above.

The drug is provided for preventing and/or treating a disease caused by a coronavirus (such as a novel coronavirus (SARS-CoV-2) or an rVSV-SARS2 pseudocoronavirus) infection, and preferably, the drug is provided for preventing and/or treating pneumonia caused by a coronavirus (such as a novel coronavirus (SARS-CoV-2) or an rVSV-SARS2 pseudocoronavirus) infection, such as pneumonia COVID-2019 caused by an SARS-CoV-2 infection (such as a respiratory disease, comprising, but not limited to, a simple infection such as fever, cough, and sore throat, pneumonia, an acute or severe acute respiratory infection, hypoxemic respiratory failure (HRF) and acute respiratory distress syndrome (ARDS), sepsis, and septic shock); or the drug is provided to serve as an inhibitor for a coronavirus (such as a novel coronavirus (SARS-CoV-2) or an rVSV-SARS2 pseudocoronavirus); or the drug is provided to inhibit the replication or reproduction of a coronavirus (such as a novel coronavirus (SARS-CoV-2) or an rVSV-SARS2 pseudocoronavirus) in a cell (such as a mammalian cell).

In some embodiments, the pharmaceutical composition is in a dosage form of a pill, a tablet, a capsule, an aqueous solution, or an aqueous suspension for oral administration, in a dosage form of a micronized suspension or solution for topical ocular administration, in a dosage form of a paste, an ointment, a lotion, a spray, or a cream for topical transdermal or mucosal administration, or in a dosage form of sterile injection water, an oil suspension, or a sterile injection solution for injection.

In some embodiments, the vesicle is produced by the following method: dissolving the compound shown in formula A or formula I or the pharmaceutically acceptable salt thereof described above in DMF or acetonitrile to obtain a solution, and subjecting the solution to an ultrasonic treatment at 30° C. to 40° C. for 1 h to 2 h to obtain the vesicle.

In some embodiments, a ratio of the mass of the compound shown in formula A or formula I or the pharmaceutically acceptable salt thereof to a volume of the DMF or the acetonitrile is 1 mg:1 mL.

In a seventh aspect of the present disclosure, the present disclosure provides a use of a compound shown in formula A or a stereoisomer, prodrug, pharmaceutically acceptable salt, or pharmaceutically acceptable solvate thereof for:

preventing and/or treating a disease caused by a coronavirus (such as a novel coronavirus (SARS-CoV-2) or an rVSV-SARS2 pseudocoronavirus) infection, and preferably, preventing and/or treating pneumonia caused by a coronavirus (such as a novel coronavirus (SARS-CoV-2) or an rVSV-SARS2 pseudocoronavirus) infection, such as pneumonia COVID-2019 caused by an SARS-CoV-2 infection (such as a respiratory disease, including, but not limited to, a simple infection such as fever, cough, and sore throat, pneumonia, an acute or severe acute respiratory infection, hypoxemic respiratory failure (HRF) and acute respiratory distress syndrome (ARDS), sepsis, and septic shock); or serving as an inhibitor for a coronavirus (such as a novel coronavirus (SARS-CoV-2) or an rVSV-SARS2 pseudocoronavirus); or inhibiting the replication or reproduction of a coronavirus (such as a novel coronavirus (SARS-CoV-2) or an rVSV-SARS2 pseudocoronavirus) in a cell (such as a mammalian cell), fullerene-$RR_1R_2R_3R_4R_5$ formula A where the fullerene is a cage-like all-carbon structure composed of a five-membered carbon ring and a six-membered carbon ring;

R is selected from the group consisting of the following:

(1) H, F, Cl, Br, I, $C_1$-$C_6$ alkyl, and $C_1$-$C_6$ alkoxy;

(2)

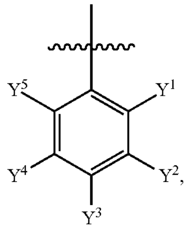

where $Y^1$, $Y^2$, $Y^3$, $Y^4$, and $Y^5$ are not all H and each are independently selected from the group consisting of the following:

1) H, and

2)

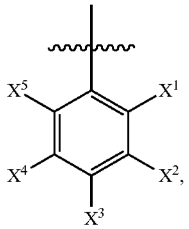

where $X^1$, $X^2$, $X^3$, $X^4$, and $X^5$ each are independently selected from the group consisting of H and $C_1$-$C_6$ alkyl substituted with 1, 2, or 3 carboxyl groups, and $X^1$, $X^2$, $X^3$, $X^4$, and $X^5$ are not all H; and (3)

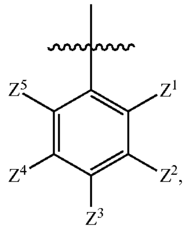

where $Z^1$, $Z^2$, $Z^3$, $Z^4$, and $Z^5$ each are independently selected from the group consisting of H and $C_1$-$C_6$ alkyl substituted with 1, 2, or 3 carboxyl groups, and $Z^1$, $Z^2$, $Z^3$, $Z^4$, and $Z^5$ are not all H; and $R^1$, $R^2$, $R^3$, $R^4$, and $R^5$ each are independently selected from the group consisting of the following (1)

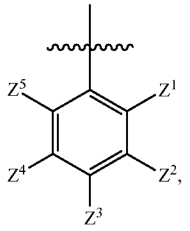

where $Z^1$, $Z^2$, $Z^3$, $Z^4$, and $Z^5$ each are independently selected from the group consisting of H and $C_1$-$C_6$ alkyl substituted with 1, 2, or 3 carboxyl groups, and $Z^1$, $Z^2$, $Z^3$, $Z^4$, and $Z^5$ are not all H; and (2)

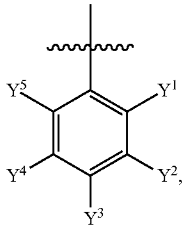

where $Y^1$, $Y^2$, $Y^3$, $Y^4$, and $Y^5$ are not all H and each are independently selected from the group consisting of the following:

1) H, and

2)

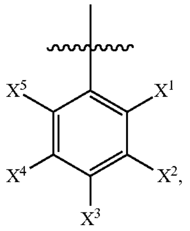

where $X^1$, $X^2$, $X^3$, $X^4$, and $X^5$ each are independently selected from the group consisting of H and $C_1$-$C_6$ alkyl substituted with 1, 2, or 3 carboxyl groups, and $X^1$, $X^2$, $X^3$, $X^4$, and $X^5$ are not all H.

In some embodiments, the fullerene further includes a seven-membered carbon ring and/or a four-membered carbon ring.

In some embodiments, the fullerene is selected from the group consisting of $C_{60}$, $C_{70}$, $C_{84}$, $C_{90}$, and $C_{100}$.

In some embodiments, the fullerene is a hollow cage-like structure or a metal or cluster-embedded structure.

In some embodiments, the fullerene is $C_{60}$, and the fullerene is a hollow cage-like structure.

In some embodiments the compound is a compound of the following general formula:

formula I

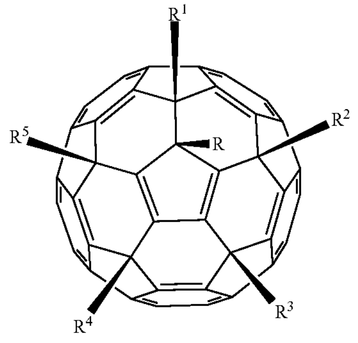

where

R is selected from the group consisting of the following:

(1) H, F, Cl, Br, I, $C_1$-$C_6$ alkyl, and $C_1$-$C_6$ alkoxy, preferably F, Cl, Br, I, and $C_1$-$C_4$ alkyl, and more preferably Cl and methyl;

(2)

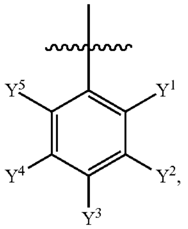

where $Y^1$, $Y^2$, $Y^3$, $Y^4$, and $Y^5$ are not all H and each are independently selected from the group consisting of the following:

1) H and

2)

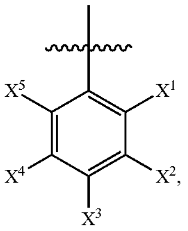

where $X^1$, $X^2$, $X^3$, $X^4$, and $X^5$ each are independently selected from the group consisting of H and $C_1$-$C_6$ alkyl substituted with 1, 2, or 3 carboxyl groups, and $X^1$, $X^2$, $X^3$, $X^4$, and $X^5$ are not all H; and (3)

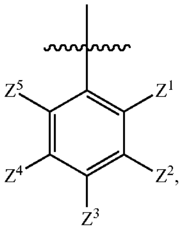

where $Z^1$, $Z^2$, $Z^3$, $Z^4$, and $Z^5$ each are independently selected from the group consisting of H and $C_1$-$C_6$ alkyl substituted with 1, 2, or 3 carboxyl groups, and $Z^1$, $Z^2$, $Z^3$, $Z^4$, and $Z^5$ are not all H; and $R^1$, $R^2$, $R^3$, $R^4$, and $R^5$ each are independently selected from the group consisting of the following:

(1)

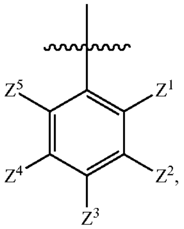

where $Z^1$, $Z^2$, $Z^3$, $Z^4$, and $Z^5$ each are independently selected from the group consisting of H and $C_1$-$C_6$ alkyl substituted with 1, 2, or 3 carboxyl groups, and $Z^1$, $Z^2$, $Z^3$, $Z^4$, and $Z^5$ are not all H; and (2)

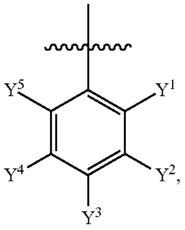

where $Y^1$, $Y^2$, $Y^3$, $Y^4$, and $Y^5$ are not all H and each are independently selected from the group consisting of the following:

1) H, and

2)

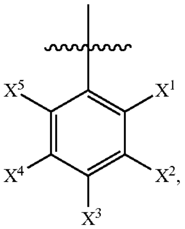

where $X^1$, $X^2$, $X^3$, $X^4$, and $X^5$ each are independently selected from the group consisting of H and $C_1$-$C_6$ alkyl substituted with 1, 2, or 3 carboxyl groups, and $X^1$, $X^2$, $X^3$, $X^4$, and $X^5$ are not all H.

In some specific embodiments, in the definition of R, $X^1$, $X^2$, $X^3$, $X^4$, and $X^5$ each are independently selected from the group consisting of H and $C_1$-$C_6$ alkyl substituted with 1 carboxyl group, and $X^1$, $X^2$, $X^3$, $X^4$, and $X^5$ are not all H.

In some specific embodiments, in the definition of R, $X^1$, $X^2$, $X^3$, $X^4$, and $X^5$ each are independently selected from the group consisting of H and

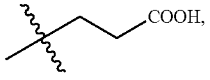 [SMILES: *CCC(=O)O]

and $X^1$, $X^2$, $X^3$, $X^4$, and $X^5$ are not all H.

In some specific embodiments, in the definition of R, $Z^1$, $Z^2$, $Z^3$, $Z^4$, and $Z^5$ each are independently selected from the group consisting of H and $C_1$-$C_6$ alkyl substituted with 1 carboxyl group, and $Z^1$, $Z^2$, $Z^3$, $Z^4$, and $Z^5$ are not all H.

In some embodiments, R is selected from the group consisting of the following:

(1) H, F, Cl, Br, I, $C_1$-$C_6$ alkyl, and $C_1$-$C_6$ alkoxy, preferably F, Cl, Br, I, and $C_1$-$C_4$ alkyl, and more preferably Cl and methyl; and (2)

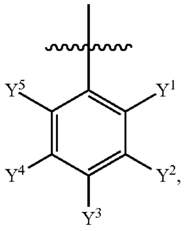

where $Y^1$, $Y^2$, $Y^3$, $Y^4$, and $Y^5$ are not all H and each are independently selected from the group consisting of the following:

1) H and

2)

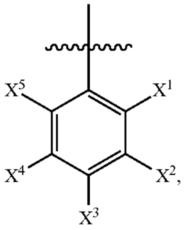

where $X^1$, $X^2$, $X^3$, $X^4$, and $X^5$ each are independently selected from the group consisting of H and $C_1$-$C_6$ alkyl substituted with 1, 2, or 3 carboxyl groups, and $X^1$, $X^2$, $X^3$, $X^4$, and $X^5$ are not all H.

In some specific embodiments, in the definition of R, $X^1$, $X^2$, $X^3$, $X^4$, and $X^5$ each are independently selected from the group consisting of H and $C_1$-$C_6$ alkyl substituted with 1 carboxyl, and $X^1$, $X^2$, $X^3$, $X^4$, and $X^5$ are not all H.

In some specific embodiments, in the definition of R $X^1$, $X^2$, $X^3$, $X^4$, and $X^5$ each are independently selected from the group consisting of H and

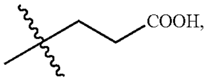

and $X^1$, $X^2$, $X^3$, $X^4$, and $X^5$ are not all H.

In some specific embodiments, in the definitions of $R^1$, $R^2$, $R^3$, $R^4$, and $R^5$, $Z^1$, $Z^2$, $Z^3$, $Z^4$, and $Z^5$ each are independently selected from the group consisting of H and $C_1$-$C_6$ alkyl substituted with 1 carboxyl group, and $Z^1$, $Z^2$, $Z^3$, $Z^4$, and $Z^5$ are not all H.

In some specific embodiments, in the definitions of $R^1$, $R^2$, $R^3$, $R^4$, and $R^5$, $Z^1$, $Z^2$, $Z^3$, $Z^4$ and $Z^5$ each are independently selected from the group consisting of H,

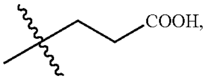 [SMILES: *CCC(=O)O]

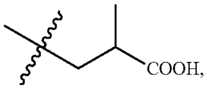

and

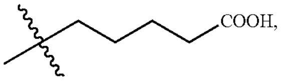

and $Z^1$, $Z^2$, $Z^3$, $Z^4$ and $Z^5$ are not all H.

In some specific embodiments, in the definitions of $R^1$, $R^2$, $R^3$, $R^4$, and $R^5$, $X^1$, $X^2$, $X^3$, $X^4$, and $X^5$ each are independently selected from the group consisting of H and $C_1$-$C_6$ alkyl substituted with 1 carboxyl group, and $X^1$, $X^2$, $X^3$, $X^4$, and $X^5$ are not all H.

In some specific embodiments, in the definitions of $R^1$, $R^2$, $R^3$, $R^4$, and $R^5$, $X^1$, $X^2$, $X^3$, $X^4$, and $X^5$ each are independently selected from the group consisting of H and

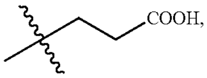 [SMILES: *CCC(=O)O]

and $X^1$, $X^2$, $X^3$, $X^4$, and $X^5$ are not all H.

In some embodiments, R is selected from the group consisting of the following:

(1) H, F, Cl, Br, I, $C_1$-$C_6$ alkyl, and $C_1$-$C_6$ alkoxy, preferably F, Cl, Br, I, and $C_1$-$C_4$ alkyl, and more preferably Cl and methyl; and (2)

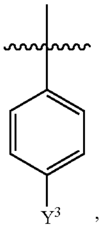

, where $Y^3$ is

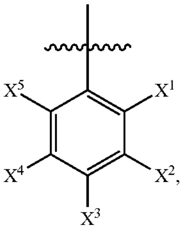

where $X^1$, $X^2$, $X^3$, $X^4$, and $X^5$ each are independently selected from the group consisting of H and $C_1$-$C_6$ alkyl substituted with 1, 2, or 3 carboxyl groups, and $X^1$, $X^2$, $X^3$, $X^4$, and $X^5$ are not all H.

In some specific embodiments, $X^1$, $X^2$, $X^3$, $X^4$, and $X^5$ each are independently selected from the group consisting of H and $C_1$-$C_6$ alkyl substituted with 1 carboxyl group, and $X^1$, $X^2$, $X^3$, $X^4$, and $X^5$ are not all H.

In some specific embodiments, $X^1$, $X^2$, $X^3$, $X^4$, and $X^5$ each are independently selected from the group consisting of H and

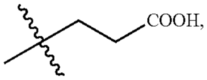 [SMILES: *CCC(=O)O]

and $X^1$, $X^2$, $X^3$, $X^4$, and $X^5$ are not all H.

In some specific embodiments, $Y^3$ is

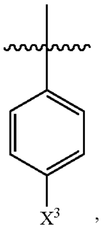

, where $X^3$ is $C_1$-$C_6$ alkyl substituted with 1, 2, or 3 carboxyl groups. In some preferred specific embodiments, $X^3$ is $C_1$-$C_6$ alkyl substituted with 1 carboxyl group. In some preferred specific embodiments, $X^3$ is

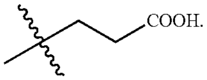 [SMILES: *CCC(=O)O]

In some embodiments, $R^1$, $R^2$, $R^3$, $R^4$, and $R^5$ each are independently selected from the group consisting of the following:

(1)

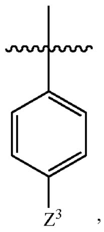
, where $Z^3$ is independently $C_1$-$C_6$ alkyl substituted with 1, 2, or 3 carboxyl groups; and (2)

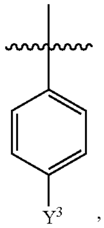
, where $Y^3$ is

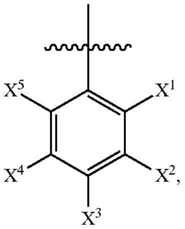

where $X^1$, $X^2$, $X^3$, $X^4$, and $X^5$ each are independently selected from the group consisting of H and $C_1$-$C_6$ alkyl substituted with 1, 2, or 3 carboxyl groups, and $X^1$, $X^2$, $X^3$, $X^4$, and $X^5$ are not all H.

In some specific embodiments, $Z^3$ is independently $C_1$-$C_6$ alkyl substituted with 1 carboxyl group.

In some specific embodiments $Z^3$ is independently selected from the group consisting of

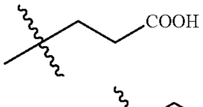
,
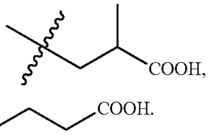
and
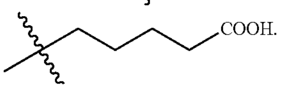

In some specific embodiments, $X^1$, $X^2$, $X^3$, $X^4$, and $X^5$ each are independently selected from the group consisting of H and $C_1$-$C_6$ alkyl substituted with 1 carboxyl group, and $X^1$, $X^2$, $X^3$, $X^4$, and $X^5$ are not all H.

In some specific embodiments $X^1$, $X^2$, $X^3$, $X^4$, and $X^5$ each are independently selected from the group consisting of H and

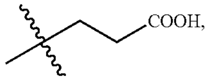

and $X^1$, $X^2$, $X^3$, $X^4$, and $X^5$ are not all H.

In some specific embodiments, $Y^3$ is

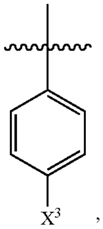
, where $X^3$ is independently $C_1$-$C_6$ alkyl substituted with 1, 2, or 3 carboxyl groups. In some preferred specific embodiments, $X^3$ is independently $C_1$-$C_6$ alkyl substituted with 1 carboxyl group. In some preferred specific embodiments, $X^3$ is

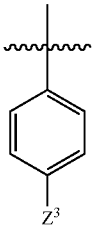
or
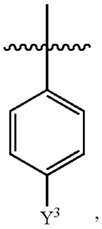
,

In some embodiments, $R^1$, $R^2$, $R^3$, $R^4$, and $R^5$ each are:

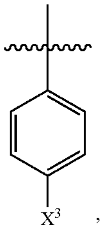
, where $Z^3$ is $C_1$-$C_6$ alkyl substituted with 1, 2, or 3 carboxyl groups; and $Y^3$ is

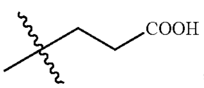
,
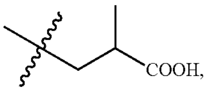
and
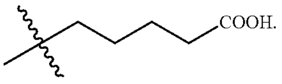

where $X^3$ is $C_1$-$C_6$ alkyl substituted with 1, 2, or 3 carboxyl groups.

In some specific embodiments, $Z^3$ is $C_1$-$C_6$ alkyl substituted with 1 carboxyl group.

In some specific embodiments, $Z^3$ is selected from the group consisting of
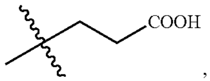 , 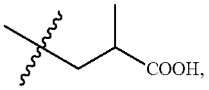 and
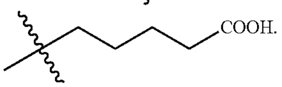
In some specific embodiments, $X^3$ is $C_1$-$C_6$ alkyl substituted with 1 carboxyl group.
In some specific embodiments, $X^3$ is
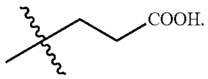 [SMILES: *CCC(=O)O]
In some embodiments, the compound shown in formula I is a compound selected from the group consisting of the following:
| Compound No. | Compound structure |
| --- | --- |
| 1 | 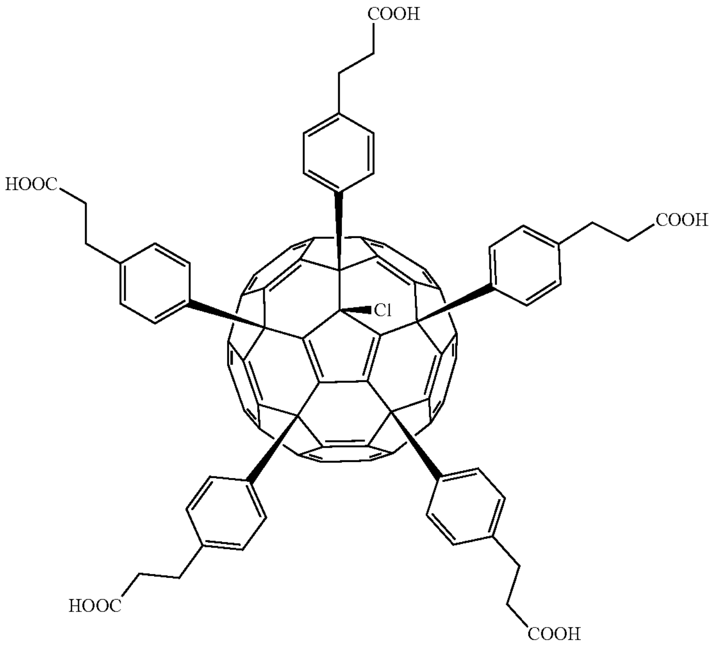 |

-continued
| Compound No. | Compound structure |
| --- | --- |
| 2 | 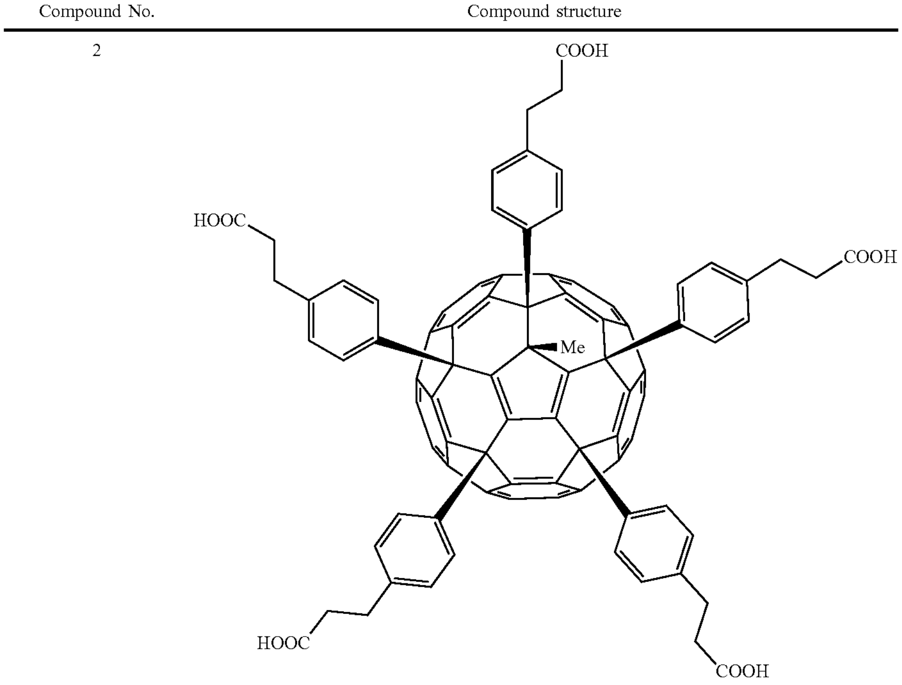 |
| 3 | 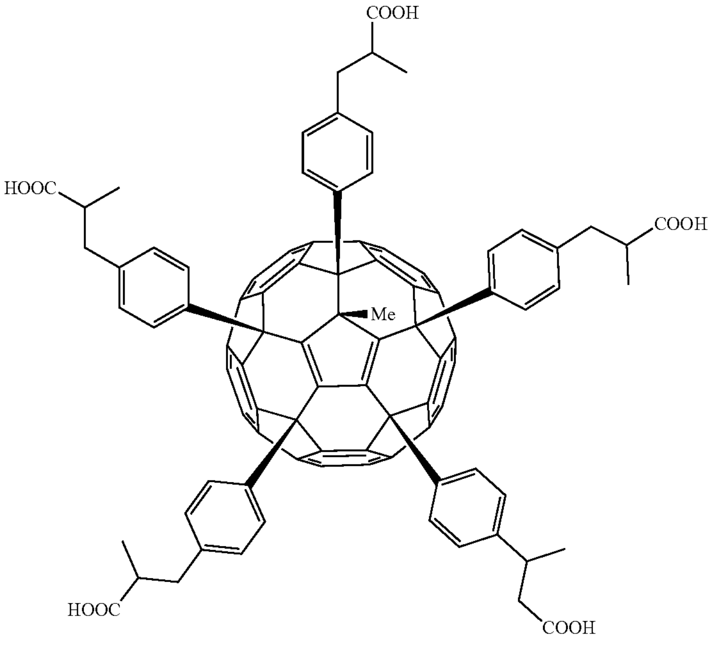 |
| 4 | 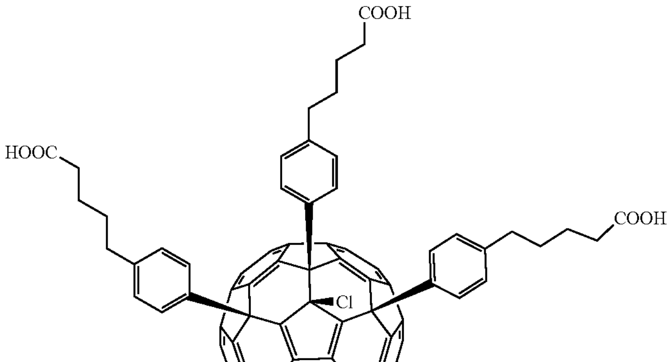 |

In an eighth aspect of the present disclosure, the present disclosure provides a pharmaceutical composition or vesicle, where the pharmaceutical composition includes the compound shown in formula A or formula I or the stereoisomer, prodrug, pharmaceutically acceptable salt, or pharmaceutically acceptable solvate thereof described above or a compound prepared by the method described above, and an optional pharmaceutically acceptable carrier or excipient; the vesicle has a diameter of 40 nm to 140 nm (such as 50 nm, 60 nm, or 70 nm) and is produced using the compound shown in formula A or formula I or the pharmaceutically acceptable salt thereof described above; and the pharmaceutical composition or vesicle is provided for preventing and/or treating a disease caused by a coronavirus (such as a novel coronavirus (SARS-CoV-2) or an rVSV-SARS2 pseudocoronavirus) infection, and preferably, preventing and/or treating pneumonia caused by a coronavirus (such as a novel coronavirus (SARS-CoV-2) or an rVSV-SARS2 pseudocoronavirus) infection, such as pneumonia COVID-2019 caused by an SARS-CoV-2 infection (such as a respiratory disease, including, but not limited to, a simple infection such as fever, cough, and sore throat, pneumonia, an acute or severe acute respiratory infection, hypoxemic respiratory failure (HRF) and acute respiratory distress syndrome (ARDS), sepsis, and septic shock); or serving as an inhibitor for a coronavirus (such as a novel coronavirus (SARS-CoV-2) or an rVSV-SARS2 pseudocoronavirus); or inhibiting the replication or reproduction of a coronavirus (such as a novel coronavirus (SARS-CoV-2) or an rVSV-SARS2 pseudocoronavirus) in a cell (such as a mammalian cell).

In some embodiments, the pharmaceutical composition is in a dosage form of a pill, a tablet, a capsule, an aqueous solution, or an aqueous suspension for oral administration, in a dosage form of a micronized suspension or solution for topical ocular administration, in a dosage form of a paste, an ointment, a lotion, a spray, or a cream for topical transdermal or mucosal administration, or in a dosage form of sterile injection water, an oil suspension, or a sterile injection solution for injection.

In some embodiments, the vesicle is produced by the following method: dissolving the compound shown in formula A or formula I or the pharmaceutically acceptable salt thereof described above in DMF or acetonitrile to obtain a solution, and subjecting the solution to an ultrasonic treatment at 30° C. to 40° C. for 1 h to 2 h to obtain the vesicle.

In some embodiments, a ratio of a mass of the compound shown in formula A or formula I or the pharmaceutically acceptable salt thereof to a volume of the DMF or the acetonitrile is 1 mg:1 mL.

In a ninth aspect of the present disclosure, the present disclosure provides a method for preventing and/or treating a disease or a method for inhibiting a virus, including: administering a preventively and/or therapeutically effective amount of a compound shown in formula A or a stereoisomer, prodrug, pharmaceutically acceptable salt, or pharmaceutically acceptable solvate thereof to a subject in need, where the disease is a disease caused by a coronavirus (such as a novel coronavirus (SARS-CoV-2) or an rVSV-SARS2 pseudocoronavirus) infection, and preferably, the disease is pneumonia caused by a coronavirus (such as a novel coronavirus (SARS-CoV-2) or an rVSV-SARS2 pseudocoronavirus) infection, such as pneumonia COVID-2019 caused by an SARS-CoV-2 infection (such as a respiratory disease, including, but not limited to, a simple infection such as fever, cough, and sore throat, pneumonia, an acute or severe acute respiratory infection, hypoxemic respiratory failure (HRF) and acute respiratory distress syndrome (ARDS), sepsis, and septic shock); and the inhibiting a virus refers to inhibiting a coronavirus (such as a novel coronavirus (SARS-CoV-2) or an rVSV-SARS2 pseudocoronavirus), and preferably, the inhibiting a virus refers to inhibiting the replication or reproduction of the virus, fullerene-$RR_1R_2R_3R_4R_5$ formula A where the fullerene is a cage-like all-carbon structure composed of a five-membered carbon ring and a six-membered carbon ring;

R is selected from the group consisting of the following:

(1) H, F, Cl, Br, I, $C_1$-$C_6$ alkyl, and $C_1$-$C_6$ alkoxy;

(2),

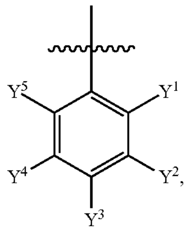

where $Y^1$, $Y^2$, $Y^3$, $Y^4$, and $Y^5$ are not all H and each are independently selected from the group consisting of the following:

1) H, and

2)

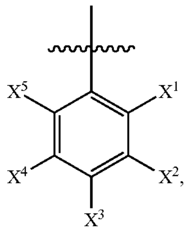

where $X^1$, $X^2$, $X^3$, $X^4$, and $X^5$ each are independently selected from the group consisting of H and $C_1$-$C_6$ alkyl substituted with 1, 2, or 3 carboxyl groups, and $X^1$, $X^2$, $X^3$, $X^4$, and $X^5$ are not all H; and (3)

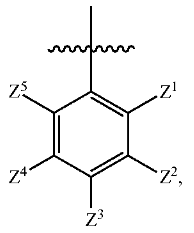

where $Z^1$, $Z^2$, $Z^3$, $Z^4$, and $Z^5$ each are independently selected from the group consisting of H and $C_1$-$C_6$ alkyl substituted with 1, 2, or 3 carboxyl groups, and $Z^1$, $Z^2$, $Z^3$, $Z^4$, and $Z^5$ are not all H; and $R^1$, $R^2$, $R^3$, $R^4$, and $R^5$ each are independently selected from the group consisting of the following:

(1)

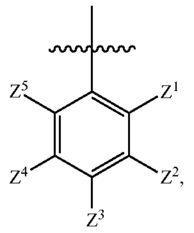

where $Z^1$, $Z^2$, $Z^3$, $Z^4$, and $Z^5$ each are independently selected from the group consisting of H and $C_1$-$C_6$ alkyl substituted with 1, 2, or 3 carboxyl groups, and $Z^1$, $Z^2$, $Z^3$, $Z^4$, and $Z^5$ are not all H; and (2)

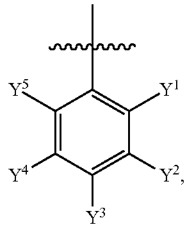

where $Y^1$, $Y^2$, $Y^3$, $Y^4$, and $Y^5$ are not all H and each are independently selected from the group consisting of the following:

1) H, and

2)

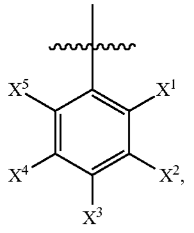

where $X^1$, $X^2$, $X^3$, $X^4$, and $X^5$ each are independently selected from the group consisting of H and $C_1$-$C_6$ alkyl substituted with 1, 2, or 3 carboxyl groups, and $X^1$, $X^2$, $X^3$, $X^4$, and $X^5$ are not all H.

In some embodiments, the fullerene further includes a seven-membered carbon ring and/or a four-membered carbon ring.

In some embodiments, the fullerene is selected from the group consisting of $C_{60}$, $C_{70}$, $C_{84}$, $C_{90}$, and $C_{100}$.

In some embodiments, the fullerene is a hollow cage-like structure or a metal or cluster-embedded structure.

In some embodiments, the fullerene is $C_{60}$, and the fullerene is a hollow cage-like structure.

In some embodiments, the compound is a compound of the following general formula:

formula I

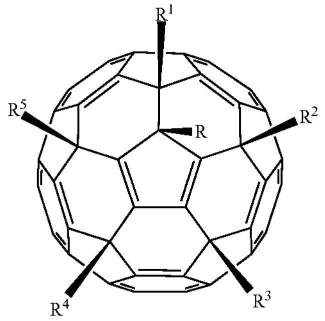

where

R is selected from the group consisting of the following:

(1) H, F, Cl, Br, I, $C_1$-$C_6$ alkyl, and $C_1$-$C_6$ alkoxy, preferably F, Cl, Br, I, and $C_1$-$C_4$ alkyl, and more preferably Cl and methyl;

(2)

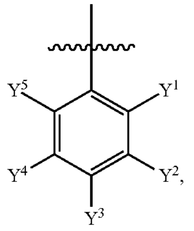

where $Y^1$, $Y^2$, $Y^3$, $Y^4$, and $Y^5$ are not all H and each are independently selected from the group consisting of the following:

1) H, and

2)

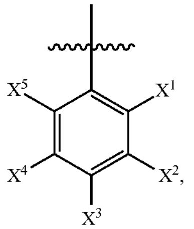

where $X^1$, $X^2$, $X^3$, $X^4$, and $X^5$ each are independently selected from the group consisting of H and $C_1$-$C_6$ alkyl substituted with 1, 2, or 3 carboxyl groups, and $X^1$, $X^2$, $X^3$, $X^4$, and $X^5$ are not all H; and (3)

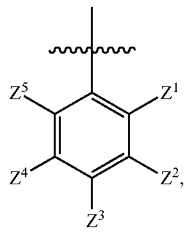

where $Z^1$, $Z^2$, $Z^3$, $Z^4$, and $Z^5$ each are independently selected from the group consisting of H and $C_1$-$C_6$ alkyl substituted with 1, 2, or 3 carboxyl groups, and $Z^1$, $Z^2$, $Z^3$, $Z^4$, and $Z^5$ are not all H; and $R^1$, $R^2$, $R^3$, $R^4$, and $R^5$ each are independently selected from the group consisting of the following:

(1)

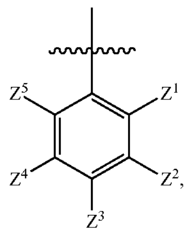

where $Z^1$, $Z^2$, $Z^3$, $Z^4$, and $Z^5$ each are independently selected from the group consisting of H and $C_1$-$C_6$ alkyl substituted with 1, 2, or 3 carboxyl groups, and $Z^1$, $Z^2$, $Z^3$, $Z^4$, and $Z^5$ are not all H; and (2)

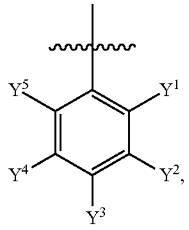

where $Y^1$, $Y^2$, $Y^3$, $Y^4$, and $Y^5$ are not all H and each are independently selected from the group consisting of the following:

1) H, and

2)

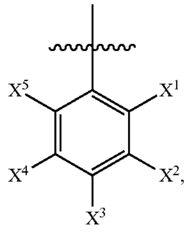

where $X^1$, $X^2$, $X^3$, $X^4$, and $X^5$ each are independently selected from the group consisting of H and $C_1$-$C_6$ alkyl substituted with 1, 2, or 3 carboxyl groups, and $X^1$, $X^2$, $X^3$, $X^4$, and $X^5$ are not all H.

In some specific embodiments, in the definition of R, $X^1$, $X^2$, $X^3$, $X^4$, and $X^5$ each are independently selected from the group consisting of H and $C_1$-$C_6$ alkyl substituted with 1 carboxyl, and $X^1$, $X^2$, $X^3$, $X^4$, and $X^5$ are not all H.

In some specific embodiments, in the definition of R $X^1$, $X^2$, $X^3$, $X^4$, and $X^5$ each are independently selected from the group consisting of H and

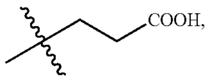 [SMILES: *CCC(=O)O]

and $X^1$, $X^2$, $X^3$, $X^4$, and $X^5$ are not all H.

In some specific embodiments, in the definition of R, $Z^1$, $Z^2$, $Z^3$, $Z^4$, and $Z^5$ each are independently selected from the group consisting of H and $C_1$-$C_6$ alkyl substituted with 1 carboxyl, and $Z^1$, $Z^2$, $Z^3$, $Z^4$, and $Z^5$ are not all H.

In some embodiments, R is selected from the group consisting of the following:

(1) H, F, Cl, Br, I, $C_1$-$C_6$ alkyl, and $C_1$-$C_6$ alkoxy, preferably F, Cl, Br, I, and $C_1$-$C_4$ alkyl, and more preferably Cl and methyl; and (2)

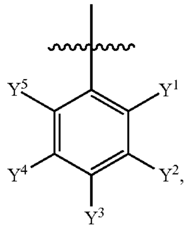

where $Y^1$, $Y^2$, $Y^3$, $Y^4$, and $Y^5$ are not all H and each are independently selected from the group consisting of the following:

1) H, and

2)

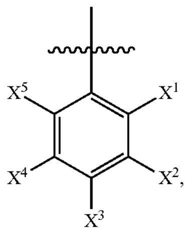

where $X^1$, $X^2$, $X^3$, $X^4$, and $X^5$ each are independently selected from the group consisting of H and $C_1$-$C_6$ alkyl substituted with 1, 2, or 3 carboxyl groups, and $X^1$, $X^2$, $X^3$, $X^4$, and $X^5$ are not all H.

In some specific embodiments, in the definition of R, $X^1$, $X^2$, $X^3$, $X^4$, and $X^5$ each are independently selected from the group consisting of H and $C_1$-$C_6$ alkyl substituted with 1 carboxyl group, and $X^1$, $X^2$, $X^3$, $X^4$, and $X^5$ are not all H.

In some specific embodiments, in the definition of R, $X^1$, $X^2$, $X^3$, $X^4$, and $X^5$ each are independently selected from the group consisting of H and

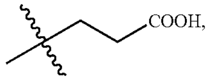 [SMILES: *CCC(=O)O]

and $X^1$, $X^2$, $X^3$, $X^4$, and $X^5$ are not all H.

In some specific embodiments, in the definitions of $R^1$, $R^2$, $R^3$, $R^4$, and $R^5$, $Z^1$, $Z^2$, $Z^3$, $Z^4$, and $Z^5$ each are independently selected from the group consisting of H and $C_1$-$C_6$ alkyl substituted with 1 carboxyl group, and $Z^1$, $Z^2$, $Z^3$, $Z^4$, and $Z^5$ are not all H.

In some specific embodiments, in the definitions of $R^1$, $R^2$, $R^3$, $R^4$, and $R^5$, $Z^1$, $Z^2$, $Z^3$, $Z^4$, and $Z^5$ each are independently selected from the group consisting of H,

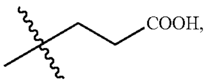 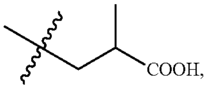 and

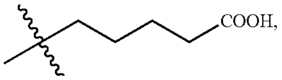

$Z^1$, $Z^2$, $Z^3$, $Z^4$, and $Z^5$ are not all H.

In some specific embodiments, in the definitions of $R^1$, $R^2$, $R^3$, $R^4$, and $R^5$, $X^1$, $X^2$, $X^3$, $X^4$, and $X^5$ each are independently selected from the group consisting of H and $C_1$-$C_6$ alkyl substituted with 1 carboxyl group, and $X^1$, $X^2$, $X^3$, $X^4$, and $X^5$ are not all H.

In some specific embodiments, in the definitions of $R^1$, $R^2$, $R^3$, $R^4$, and $R^5$, $X^1$, $X^2$, $X^3$, $X^4$, and $X^5$ each are independently selected from the group consisting of H and

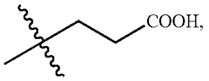 [SMILES: *CCC(=O)O]

and $X^1$, $X^2$, $X^3$, $X^4$, and $X^5$ are not all H.

In some embodiments, R is selected from the group consisting of the following:

(1) H, F, Cl, Br, I, $C_1$-$C_6$ alkyl, and $C_1$-$C_6$ alkoxy, preferably F, Cl, Br, I, and $C_1$-$C_4$ alkyl, and more preferably Cl and methyl; and (2)

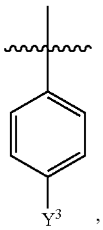, where $Y^3$ is

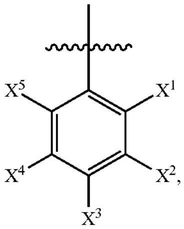

where $X^1$, $X^2$, $X^3$, $X^4$, and $X^5$ each are independently selected from the group consisting of H and $C_1$-$C_6$ alkyl substituted with 1, 2, or 3 carboxyl groups, and $X^1$, $X^2$, $X^3$, $X^4$, and $X^5$ are not all H.

In some specific embodiments, $X^1$, $X^2$, $X^3$, $X^4$, and $X^5$ each are independently selected from the group consisting of H and $C_1$-$C_6$ alkyl substituted with 1 carboxyl group, and $X^1$, $X^2$, $X^3$, $X^4$, and $X^5$ are not all H.

In some specific embodiments $X^1$, $X^2$, $X^3$, $X^4$, and $X^5$ each are independently selected from the group consisting of H and

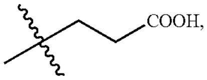 [SMILES: *CCC(=O)O]

and $X^1$, $X^2$, $X^3$, $X^4$, and $X^5$ are not all H.

In some specific embodiments, $Y^3$ is

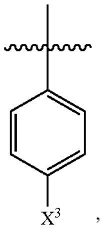, where $X^3$ is $C_1$-$C_6$ alkyl substituted with 1, 2, or 3 carboxyl groups. In some preferred specific embodiments, $X^3$ is $C_1$-$C_6$ alkyl substituted with 1 carboxyl group. In some preferred specific embodiments, $X^3$ is

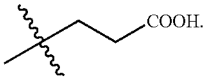 [SMILES: *CCC(=O)O]

In some embodiments, $R^1$, $R^2$, $R^3$, $R^4$, and $R^5$ each are independently selected from the group consisting of the following:

(1)

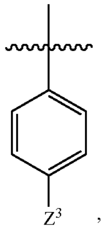
, where $Z^3$ is independently $C_1$-$C_6$ alkyl substituted with 1, 2, or 3 carboxyl groups; and (2)

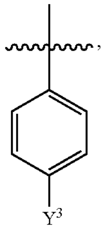

where $Y^3$ is

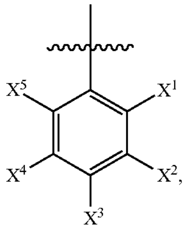

where $X^1$, $X^2$, $X^3$, $X^4$, and $X^5$ each are independently selected from the group consisting of H and $C_1$-$C_6$ alkyl substituted with 1, 2, or 3 carboxyl groups, and $X^1$, $X^2$, $X^3$, $X^4$, and $X^5$ are not all H.

In some specific embodiments, $Z^3$ is independently $C_1$-$C_6$ alkyl substituted with 1 carboxyl group.

In some specific embodiments, $Z^3$ is independently selected from the group consisting of

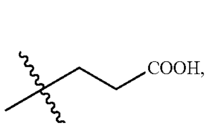
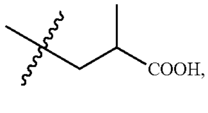
and
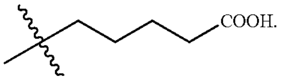

In some specific embodiments, $X^1$, $X^2$, $X^3$, $X^4$, and $X^5$ each are independently selected from the group consisting of H and $C_1$-$C_6$ alkyl substituted with 1 carboxyl group, and $X^1$, $X^2$, $X^3$, $X^4$, and $X^5$ are not all H.

In some specific embodiments, $X^1$, $X^2$, $X^3$, $X^4$, and $X^5$ each are independently selected from the group consisting of H and

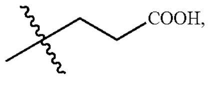 [SMILES: *CCC(=O)O]

and $X^1$, $X^2$, $X^3$, $X^4$, and $X^5$ are not all H.

In some specific embodiments, $Y^3$ is

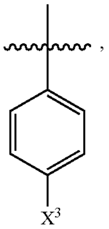

where $X^3$ is independently $C_1$-$C_6$ alkyl substituted with 1, 2, or 3 carboxyl groups. In some preferred specific embodiments, $X^3$ is independently $C_1$-$C_6$ alkyl substituted with 1 carboxyl group. In some preferred specific embodiments, $X^3$ is

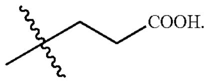 [SMILES: *CCC(=O)O]

In some embodiments, $R^1$, $R^2$, $R^3$, $R^4$, and $R^5$ each are:

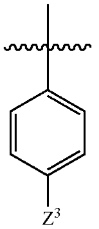
or
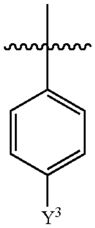
, where $Z^3$ is $C_1$-$C_6$ alkyl substituted with 1, 2, or 3 carboxyl groups; and $Y^3$ is

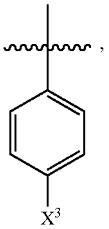

where $X^3$ is $C_1$-$C_6$ alkyl substituted with 1, 2, or 3 carboxyl groups.

In some specific embodiments, $Z^3$ is $C_1$-$C_6$ alkyl substituted with 1 carboxyl group.

In some specific embodiments $Z^3$ is selected from the group consisting of

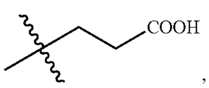, 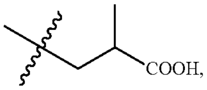 and
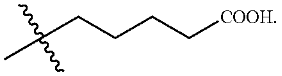
In some specific embodiments, $X^3$ is $C_1$-$C_6$ alkyl substituted with 1 carboxyl group.
In some specific embodiments, $X^3$ is
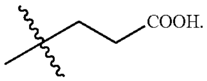 [SMILES: *CCC(=O)O]
In some embodiments, the compound shown in formula I is a compound selected from the group consisting of the following:
| Compound No. | Compound structure |
| --- | --- |
| 1 | 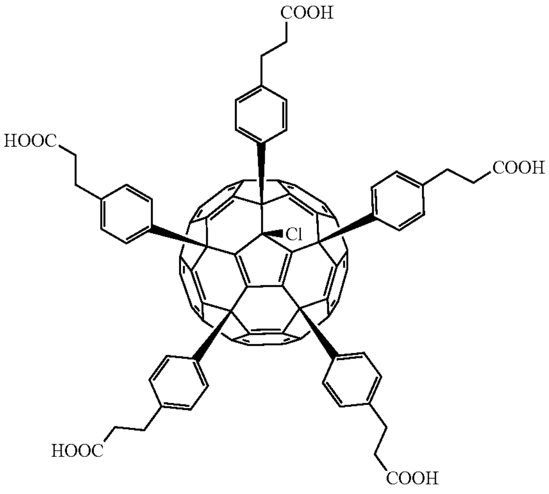 |
| 2 | 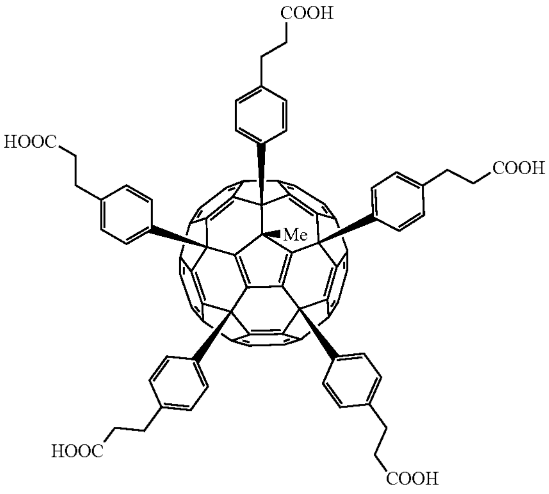 |

-continued
| Compound No. | Compound structure |
| --- | --- |
| 3 | 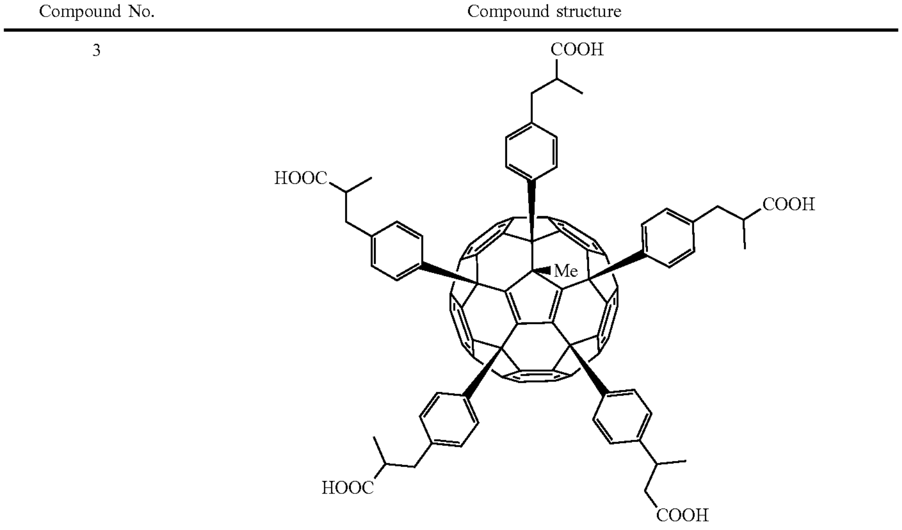 |
| 4 | 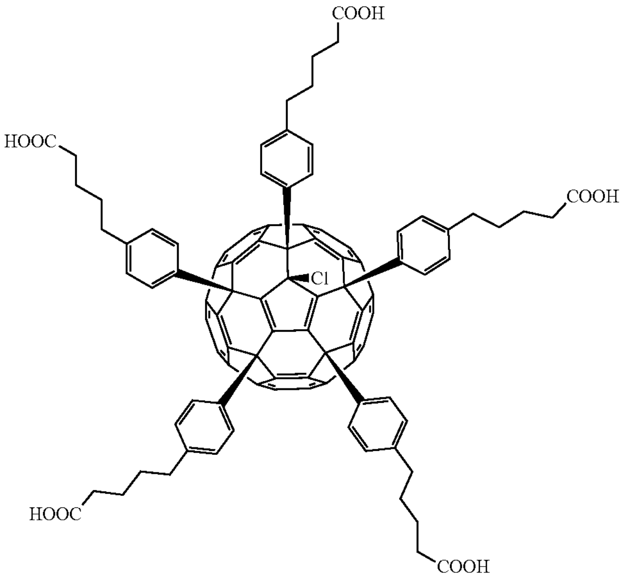 |
| 5 | 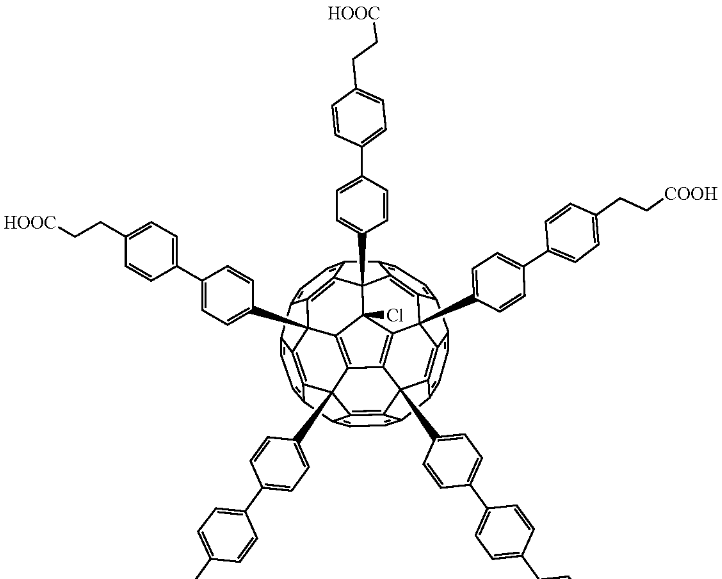 |

In a tenth aspect of the present disclosure, the present disclosure provides a method for preventing and/or treating a disease or a method for inhibiting a virus, including: administering a preventively and/or therapeutically effective amount of a pharmaceutical composition or vesicle to a subject in need, where the pharmaceutical composition includes the compound shown in formula A or formula I or the stereoisomer, prodrug, pharmaceutically acceptable salt, or pharmaceutically acceptable solvate thereof described above or a compound prepared by the method described above, and an optional pharmaceutically acceptable carrier or excipient; the vesicle has a diameter of 40 nm to 140 nm (such as 50 nm, 60 nm, or 70 nm) and is produced using the compound shown in formula A or formula I or the pharmaceutically acceptable salt thereof described above;

where the disease is a disease caused by a coronavirus (such as a novel coronavirus (SARS-CoV-2) or an rVSV-SARS2 pseudocoronavirus) infection, and preferably, the disease is pneumonia caused by a coronavirus (such as a novel coronavirus (SARS-CoV-2) or an rVSV-SARS2 pseudocoronavirus) infection, such as pneumonia COVID-2019 caused by an SARS-CoV-2 infection (such as a respiratory disease, including, but not limited to, a simple infection such as fever, cough, and sore throat, pneumonia, an acute or severe acute respiratory infection, hypoxemic respiratory failure (HRF) and acute respiratory distress syndrome (ARDS), sepsis, and septic shock); and the inhibiting a virus refers to inhibiting a coronavirus (such as a novel coronavirus (SARS-CoV-2) or an rVSV-SARS2 pseudocoronavirus), and preferably, the inhibiting a virus refers to inhibiting the replication or reproduction of the virus.

In some embodiments, the pharmaceutical composition is in a dosage form of a pill, a tablet, a capsule, an aqueous solution, or an aqueous suspension for oral administration, in a dosage form of a micronized suspension or solution for topical ocular administration, in a dosage form of a paste, an ointment, a lotion, a spray, or a cream for topical transdermal or mucosal administration, or in a dosage form of sterile injection water, an oil suspension, or a sterile injection solution for injection.

In some embodiments, the vesicle is produced by the following method: dissolving the compound shown in formula A or formula I or the pharmaceutically acceptable salt thereof described above in DMF or acetonitrile to obtain a solution, and subjecting the solution to an ultrasonic treatment at 30° C. to 40° C. for 1 h to 2 h to obtain the vesicle. In some embodiments, a ratio of a mass of the compound shown in formula A or formula I or the pharmaceutically acceptable salt thereof to a volume of the DMF or the acetonitrile is 1 mg:1 mL.

Unless otherwise specified, the above groups and substituents have common meanings in the field of pharmaceutical chemistry.

In each part of the present specification, a substituent of the compound disclosed in the present disclosure is disclosed according to a type or scope of a group. In particular, the present disclosure includes each independent subcombination of members of the type or scope of the group. For example, the term "$C_1$-$C_6$ alkyl" refers, in particular, to independently disclosed methyl, ethyl, $C_3$ alkyl, $C_4$ alkyl, $C_5$ alkyl, and $C_6$ alkyl.

In addition, it should be noted that, unless otherwise explicitly specified, the terms in the description such as " . . . each are independently"and " . . . each are independently selected from the group consisting of" used throughout the present application can be used interchangeably, and should be understood in a broad sense, which can mean that, in different groups, specific options expressed by the same or different symbols do not affect each other, or in the same group, specific options expressed by the same or different symbols do not affect each other.

For example, $R^1$, $R^2$, $R^3$, $R^4$, and $R^5$ each are independently

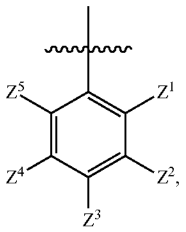

where $Z^1$, $Z^2$, $Z^3$, $Z^4$, and $Z^5$ each are independently selected from the group consisting of H and $C_1$-$C_6$ alkyl substituted with 1, 2 or 3 carboxyl groups. The expression "$R^1$, $R^2$, $R^3$, $R^4$, and $R^5$ each are independently

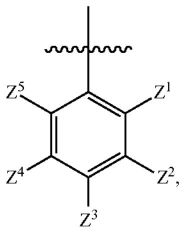

means that the specific options for the different groups $R^1$, $R^2$, $R^3$, $R^4$, and $R^5$ do not affect each other and may be the same or different. The expression "$Z^1$, $Z^2$, $Z^3$, $Z^4$, and $Z^5$ each are independently selected from the group consisting of H and $C_1$-$C_6$ alkyl substituted with 1, 2, or 3 carboxyl" means that, in the same group (such as $R^1$), the specific options for the different symbols $Z^1$, $Z^2$, $Z^3$, $Z^4$, and $Z^5$ do not affect each other and may be the same or different; and in the different groups $R^1$, $R^2$, $R^3$, $R^4$, and $R^5$, the specific options for the same symbol (such as $Z^1$) do not affect each other and may be the same or different.

Moreover, it should be noted that the phrase " . . . each are" or "each . . . is" means that, in different groups, the specific options for the same or different symbols are the same; or, in the same group, the specific options for the same or different symbols are the same.

For example, $R^1$, $R^2$, $R^3$, $R^4$, and $R^5$ each are

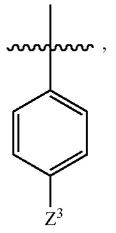

where $Z^3$ is $C_1$-$C_6$ alkyl substituted with 1, 2, or 3 carboxyl. The expression "$R^1$, $R^2$, $R^3$, $R^4$, and $R^5$ each are

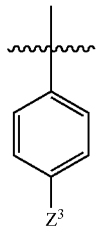, means that the specific options for the different groups $R^1$, $R^2$, $R^3$, $R^4$, and $R^5$ are the same. The expression "$Z^3$ is $C_1$-$C_6$ alkyl substituted with 1, 2, or 3 carboxyl" means that, in the different groups $R^1$, $R^2$, $R^3$, $R^4$, and $R^5$, the specific options for the same symbol $Z^3$ are the same and each are $C_1$-$C_6$ alkyl substituted with 1, 2, or 3 carboxyl, such as

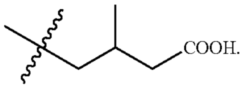 [SMILES: *CC(C)CC(=O)O]

The term "$C_1$-$C_6$ alkyl" refers to any linear or branched group with 1 to 6 carbon atoms, such as methyl, ethyl, n-propyl, isopropyl, n-butyl, isobutyl, tert-butyl, sec-butyl, n-pentyl, tert-pentyl, and n-hexyl.

The term "$C_2$-$C_6$ alkyl" refers to any linear or branched group with 2 to 6 carbon atoms, such as ethyl, n-propyl, isopropyl, n-butyl, isobutyl, tert-butyl, n-pentyl, tert-pentyl, and n-hexyl.

The term "$C_1$-$C_4$ alkyl" refers to any linear or branched group with 1 to 4 carbon atoms, such as methyl, ethyl, n-propyl, isopropyl, n-butyl, isobutyl, and tert-butyl.

The term "$C_1$-$C_6$ alkyl substituted with 1, 2, or 3 carboxyl groups" refers to a group obtained by substituting hydrogen atoms in a $C_1$-$C_6$ alkyl backbone with 1, 2, or 3 carboxyl groups, such as

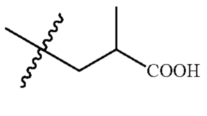 or 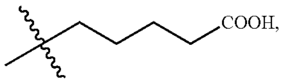, where the $C_1$-$C_6$ alkyl is as defined above and the carboxyl group is —COOH.

The term "alkoxy" refers to a group obtained by linking an oxygen atom (—O—) to the alkyl described above (such as $C_1$-$C_6$ alkyl and $C_1$-$C_4$ alkyl).

As used herein, unless otherwise stated, the term "prodrug" refers to a derivative that can undergo hydrolysis, oxidization, or another reaction under biological conditions (in vitro or in vivo) to produce the compound of the present disclosure. The prodrug becomes an active compound only through such a reaction under biological conditions, or the prodrug is active in the form in which the prodrug does not react. The prodrug can often be prepared using a well-known method, such as those described in Burger's Medicinal Chemistry and Drug Discovery (1995) 172-178, 949-982 (edited by Manfred E. Wolff, 5th edition).

As used herein, the term "pharmaceutically acceptable salt of a compound shown in formula A or formula (I)" refers to a salt produced through a reaction of the compound shown in formula A or formula (I) with an organic alkali or an inorganic alkali (such as sodium hydroxide, potassium hydroxide, potassium carbonate, calcium hydroxide, magnesium hydroxide, zinc hydroxide, and ammonia water). In some embodiments, the pharmaceutically acceptable salt of a compound shown in formula A or formula (I) refers to a potassium, sodium, magnesium, calcium, or zinc salt of the compound shown in formula A or formula (I). In some specific embodiments, the pharmaceutically acceptable salt of a compound shown in formula A or formula (I) refers to a potassium salt of the compound shown in formula A or formula (I).

The pharmaceutically acceptable salt may be obtained using a standard process well known in the art, for example, the pharmaceutically acceptable salt may be prepared through a reaction of a sufficient amount of an alkaline compound with a suitable acid to provide a pharmaceutically acceptable anion.

The term "treating" used herein generally refers to the acquisition of a desired pharmacological and/or physiological effect. The pharmacological and/or physiological effect can be preventive depending on the complete or partial prevention of a disease or symptoms thereof; and/or may be therapeutic depending on the partial or complete stabilization or cure of a disease and/or side effects caused by the disease. The term "treating" used herein covers any treatment of a disease of a patient, including: (a) prevention of a disease or symptoms thereof that occur in a patient who is susceptible to the disease or symptoms but has not yet been diagnosed; (b) inhibition of symptoms of a disease, that is, stopping the development of the disease; or (c) alleviation of symptoms of a disease, that is, causing the degeneration of the disease or symptoms thereof.

According to a specific technical solution of the present disclosure, for the compound and the stereoisomer, prodrug, pharmaceutically acceptable salt, or pharmaceutically acceptable solvate thereof, the compound refers to one of the compounds described in the following embodiments.

In addition, the present disclosure provides a pharmaceutical composition, including the compound or the stereoisomer, prodrug, pharmaceutically acceptable salt, or pharmaceutically acceptable solvate thereof described in any one of the above technical solutions, and a pharmaceutically acceptable carrier, diluent, or excipient.

A method for preparing a pharmaceutical composition with a specified amount of an active ingredient is known, or is apparent to those skilled in the art according to the disclosure of the present disclosure. As described in REMINGTON'S PHARMACEUTICAL SCIENCES, Martin, E. W., ed., Mack Publishing Company, 19th ed. (1995), the method for preparing the pharmaceutical composition includes the incorporation of an appropriate pharmaceutical excipient, carrier, diluent, or the like.

The pharmaceutical preparation of the present disclosure is prepared by a known method, including a conventional mixing, dissolving, or lyophilizing method. The compound of the present disclosure may be prepared into a pharmaceutical composition and administered to a patient in various ways suitable for the selected mode of administration, such as administering orally or parenterally (intravenously, intramuscularly, locally, or subcutaneously) or spraying on the skin, mucous membrane, and or the like.

Therefore, the compound of the present disclosure may be administered systemically in combination with a pharmaceutically acceptable carrier (such as an inert diluent or an assimilable edible carrier), such as, orally. The compound can be encapsulated in a hard or soft gelatin capsule and can be pressed into a tablet. For oral therapeutic administration, the active compound may be combined with one or more excipients and may be administered in the form of a swallowable tablet, a buccal tablet, a lozenge, a capsule, an elixir, a suspension, a syrup, a round tablet, or the like. Such a composition or formulation should include at least 0.1% of the active compound. The proportion of the active compound in such a composition or formulation can of course vary, and the weight of the active compound can be about 1% to about 99% of a weight of a given unit dosage form. In such a therapeutically effective composition, an amount of the active compound enables an effective dose level.

The tablet, lozenge, pill, capsule, or the like may further include: a binder, such as tragacanth gum, arabic gum, corn starch, or gelatin; an excipient, such as dicalcium phosphate (DCP); a disintegrant, such as corn starch, potato starch, or alginic acid; a lubricant, such as magnesium stearate; a sweetener, such as sucrose, fructose, lactose, or aspartame; or a flavoring agent, such as a peppermint, wintergreen oil, or a cherry flavor. When the unit dosage form is a capsule, in addition to the above substances, the capsule may further include a liquid carrier, such as vegetable oil or polyethylene glycol (PEG). Another substance may be added to provide a coating or change the physical form of a solid unit dosage form in another way. For example, the tablet, pill, or capsule can be coated with gelatin, wax, shellac, or sugar. The syrup or elixir may include the active compound, sucrose or fructose as a sweetener, methyl parahydroxybenzoate or propyl parahydroxybenzoate as a preservative, a dye, and a flavoring agent (such as cherry or orange flavors). Of course, any substance used to prepare any unit dosage form should be pharmaceutically acceptable and should be used at a substantially non-toxic amount. In addition, the active compound can be incorporated into a sustained-release preparation or a sustained-release device.

The active compound can also be administered intravenously or intraperitoneally through infusion or injection. The active compound or the salt thereof can be prepared into an aqueous solution, or the aqueous solution is optionally mixed with a non-toxic surfactant. The active compound or the salt thereof can also be dispersed into glycerol, liquid PEG, or glycerol triacetate, or a mixture thereof, or oil. Under normal storage and use conditions, these preparations include a preservative to prevent the growth of microorganisms.

A pharmaceutical dosage form suitable for injection or infusion may include a sterile injectable or infusionable aqueous solution, dispersion, or powder including the active ingredient (optionally encapsulated in a liposome) of an immediate formulation. In all cases, a final dosage form must be sterile, liquid, and stable under production and storage conditions. The liquid carrier may be a solvent or a liquid dispersion medium, including, for example, water, ethanol, a polyol (such as glycerol, propylene glycol (PG), and liquid PEG), vegetable oil, a non-toxic glyceride, and a suitable mixture thereof. Suitable fluidity can be maintained, for example, through the production of a liposome, by maintaining a desired particle size in the presence of a dispersant, or through the addition of a surfactant. A variety of antibacterial agents and antifungal agents (such as parahydroxybenzoate, chlorobutanol, phenol, sorbic acid, and thiomersal) can be used to provide a preventive effect for microorganisms. In many cases, an isotonic agent is preferably included, such as a sugar, a buffer, or sodium chloride. An absorption retardant (such as aluminum monostearate and gelatin) can be added to the composition to achieve the prolonged absorption of the injectable composition.

A desired amount of the active compound in a suitable solvent is mixed with the various other ingredients listed above as needed, and a resulting mixture is filtered for sterilization to obtain a sterile injectable solution. A sterile powder for the preparation of a sterile injection solution is preferably prepared through a vacuum drying or lyophilization technology, which makes a powder product include both an active ingredient and any additional desired component present in the previously sterile filtered solution.

A useful solid carrier includes a crushed solid (such as talc, clay, microcrystalline cellulose (MCC), silicon dioxide, and aluminum oxide). A useful liquid carrier includes water, ethanol, or ethylene glycol (EG), or a water-ethanol/EG mixture, and the compound of the present disclosure may be optionally dissolved or dispersed in the liquid carrier at an effective content with the help of a non-toxic surfactant. An adjuvant (such as a flavor) and an additional antimicrobial agent can be added to optimize the properties for a given use.

A thickening agent (such as synthetic polymers, fatty acids, fatty acid salts and esters, fatty alcohols, modified cellulose, or modified inorganic materials) may also be used with the liquid carrier to form a paste, gel, ointment, soap, or the like for coating, which can be directly applied to the skin of a user.

The above preparations may exist in a unit dosage form, which is a physically dispersible unit including a unit dose and is suitable for administration to humans and other mammalian bodies. The unit dosage form may be a capsule or a tablet, or many capsules or tablets. According to a specific treatment involved, a unit dose of the active ingredient can vary or can be adjusted in a range of about 0.1 mg to about 1,000 mg or more.

In addition, various new pharmaceutical dosage forms such as an emulsion liposome, a microsphere, and a nanosphere can be adopted, such as a pharmaceutical dosage form prepared with a microparticle dispersion system including a polymeric micelle, a nanoemulsion, a submicroemulsion, a microcapsule, a microsphere, a liposome, and a niosome (also known as a nonionic surfactant vesicle).

In the present disclosure, the term “subject” refers to a vertebrate. In some embodiments, the vertebrate refers to a mammal. The mammal includes, but is not limited to, livestock (such as cattle), pets (such as cats, dogs, and horses), primates, mice, and rats. In some embodiments, the mammal refers to a human.

In the present disclosure, the term “effective amount” refers to a necessary dose and an amount that can effectively achieve a desired therapeutic or preventive effect temporally. The therapeutically effective amount of a substance/molecule of the present disclosure may vary according to factors such as a disease state, age, sex, and body weight of an individual and an ability of the substance/molecule to elicit a desired response in an individual. The therapeutically effective amount also encompasses an amount at which a therapeutic beneficial effect of the substance/molecule outweighs any toxic or harmful consequences of the substance/molecule.

The term “preventively effective amount” refers to a necessary dose and an amount that can effectively achieve a desired preventive effect temporally. Because the preventively effective amount is administered to a subject before the onset of a disease or at an early stage of a disease, the preventively effective amount is often, but not necessarily, lower than the therapeutically effective amount.

DETAILED DESCRIPTION OF THE EMBODIMENTS

Figure 1:
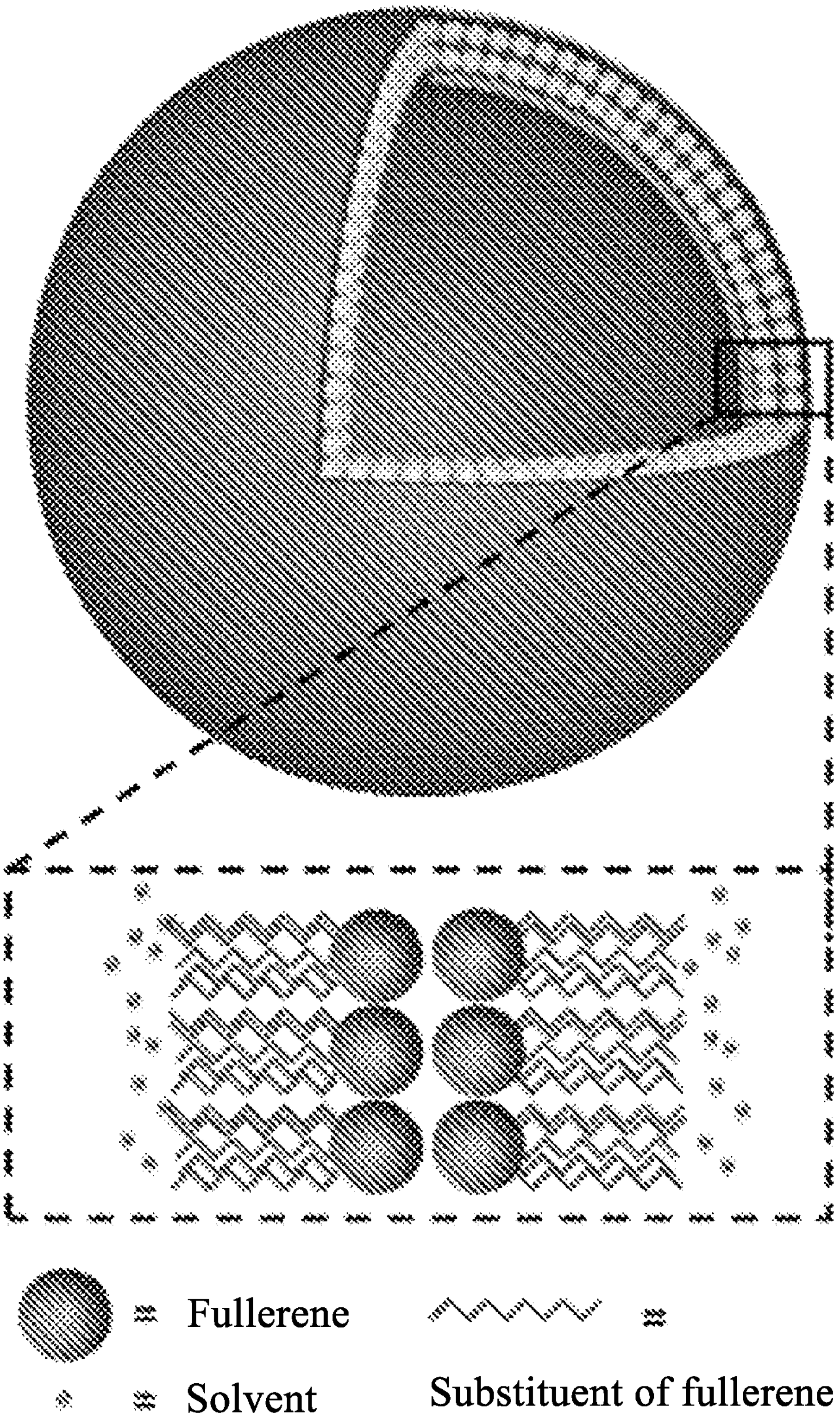
FIG. 1 is a schematic diagram illustrating the structure of the vesicle of the present disclosure.

The embodiments of the present disclosure are described in detail below through specific examples, but in any case, the examples should not be interpreted as limitations on the present disclosure.

An objective of the present disclosure is to provide a water-soluble polyaryl carboxylic fullerene derivative and a use thereof in the preparation of a drug for preventing or treating a coronavirus.

In particular, to solve the technical problem of the present disclosure, the following technical solution is adopted:

formula (O)

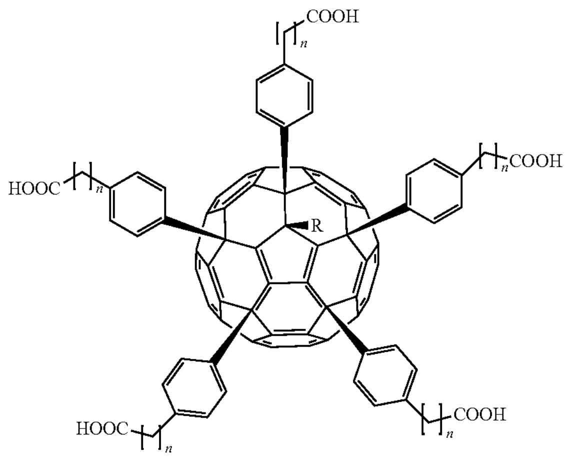

where n is any integer from 1 to 6.

In some embodiments, the coronavirus is not limited to the novel coronavirus (SARS-CoV-2).

In some embodiments, the drug is a drug with the water-soluble polyaryl carboxylic fullerene derivative shown in formula (O) as an active ingredient.

In some embodiments, the drug is a monomer compound with the water-soluble polyaryl carboxylic fullerene derivative shown in formula (O) as an active ingredient.

In some embodiments, the drug includes the water-soluble polyaryl carboxylic fullerene derivative shown in formula (O) and a pharmaceutically acceptable carrier or excipient.

In some embodiments, the drug has a dosage form of a pill, a tablet, a capsule, or an oral liquid.

The present disclosure is further explained below in conjunction with specific examples.

6 water-soluble polyaryl carboxylic fullerene derivatives (compounds 1 to 6) and potassium salts thereof are synthesized by the inventors, and a role of the potassium salts in the inhibition of a coronavirus in vitro is evaluated. A BHK21-hACE2 cell and an rVSV-SARS2 pseudocoronavirus were used to conduct an in vitro experiment, and an AGMK cell (Vero E6) and a novel coronavirus (SARS-CoV-2) were also used to conduct an in vitro experiment, such as to screen candidate compounds.

Example 1 Preparation of Compounds

Specific molecular structures of the 6 water-soluble polyaryl carboxylic fullerene derivatives (compounds 1 to 6) synthesized by the inventors were shown in Table 1 below.

Table 1 Compound Structures

| Compound No. | Compound structure |
| --- | --- |
| 1 | 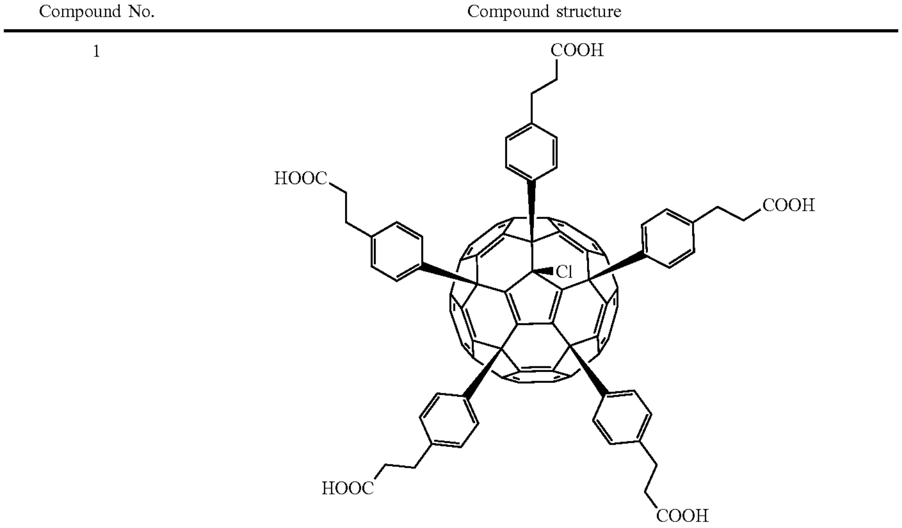 |
| 2 | 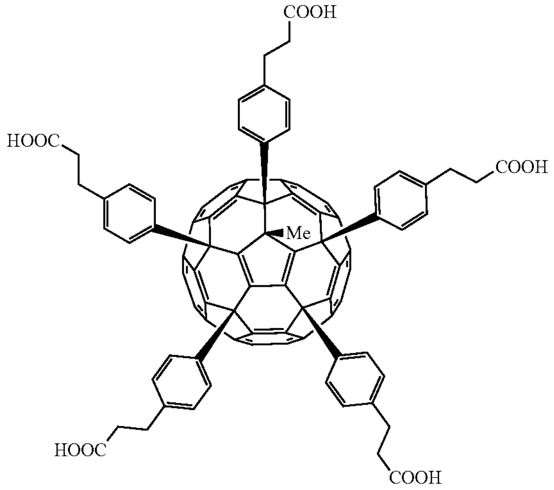 |
| 3 | 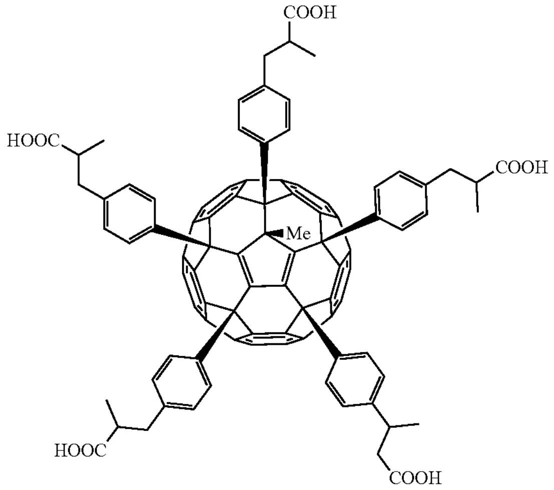 |
| 4 | 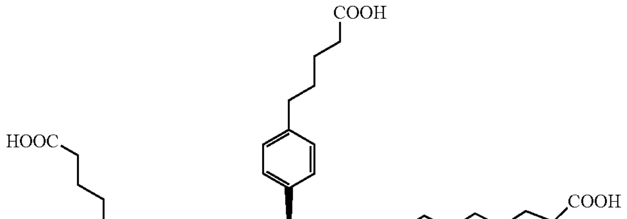 |

1. Preparation Methods Of Compounds 1 and 2 can be found in Org. Biomol. Chem., 2019, 17, 7155-7160.

2. a Preparation Method for Compound 3 is as Follows:

$C_{60}Cl_6$ (200 mg, 0.214 mmol, 1 equiv) and α-methylhydrocinnamic acid (878 mg, 5.36 mmol, 25 equiv) were dissolved in 50 mL of nitrobenzene under water-free and oxygen-free conditions, then 0.1 mL of $SnCl_4$ was added, and a reaction was conducted at 80° C. for 2 h. After the reaction was complete, the resulting system was cooled to room temperature, and 300 mL of acetonitrile was added for precipitation. The resulting precipitate was filtered out through suction filtration, washed with n-hexane three times, dried, and then dissolved with a potassium hydroxide solution. The resulting solution was filtered to remove insoluble matters, a filtrate was collected, and hydrochloric acid was added dropwise to the filtrate until a pH of the filtrate was 7.0, such that a red precipitate was produced. The red precipitate was filtered out through suction filtration and then dried to obtain a product 3 (compound 3).

Identification of compound 3:

$^1$H NMR (500 MHz, DMSO-d6, δ, ppm) 12.14 (br.s, 5H), 7.80 (m, 4H), 7.53 (m, 4H), 7.36-7.14 (m, 6H), 7.11-6.97 (m, 4H), 6.85-6.61 (m, 2H), 2.96 (m, 4H), 2.64 (m, 1H), 2.42-1.89 (m, 5H), 1.24 (m, 5H), 1.02 (m, 12H).

$^{13}$CNMR (126 MHz, DMSO-$d_6$, δ, ppm) 176.27, 148.81, 148.76, 148.68, 148.68, 148.49, 148.39, 148.31, 148.25, 148.08, 148.08, 147.95, 147.87, 147.64, 147.29, 144.54, 144.42, 144.41, 144.24, 144.14, 144.07, 144.04, 143.88, 143.69, 143.63, 139.58, 139.14, 139.02, 138.88, 138.86, 138.70, 138.54, 138.39, 138.07, 135.43, 135.20, 130.13, 129.96, 129.75, 129.47, 129.43, 129.38, 129.35, 129.28, 129.18, 129.18, 128.95, 128.90, 128.78, 128.69, 128.54, 128.43, 128.26, 128.20, 128.06, 128.03, 127.91, 127.83, 127.73, 127.52, 125.03, 77.27, 77.27, 77.22, 77.02, 76.76, 51.63, 41.28, 39.22, 32.21, 29.71, 29.33, 26.40, 23.43.

Molecular formula: $C_{110}H_{57}ClO_{10}$; and mass spectrometry (MS) (MALDI-TOF), m/z: 1571.7.

3. A Preparation Method for Compound 4 is as Follows:

$C_{60}Cl_6$ (200 mg, 0.214 mmol, 1 equiv) and 5-phenylvaleric acid (953 mg, 5.36 mmol, 25 equiv) were dissolved in 50 mL of nitrobenzene under water-free and oxygen-free conditions, then 0.1 mL of $SnCl_4$ was added, and a reaction was conducted at 80° C. for 2 h. After the reaction was complete, the resulting system was cooled to room temperature, and 300 mL of acetonitrile was added for precipitation. The resulting precipitate was filtered out through suction filtration, washed with n-hexane three times, dried, and then dissolved with a potassium hydroxide solution; the resulting solution was filtered to remove insoluble matters, a filtrate was collected, and hydrochloric acid was added dropwise to the filtrate until a pH of the filtrate was 7.0, such that a red precipitate was produced. The red precipitate was filtered out through suction filtration and then dried to obtain a product 4 (compound 4).

Identification of compound 4:

$^1$H NMR (500 MHz, DMSO-$d_6$, δ, ppm) 11.96 (br.s, 5H), 7.72 (m, 1H), 7.54 (m, 3H), 7.47-7.24 (m, 3H), 7.13 (m, 6H), 7.00 (m, 2H), 6.85 (m, 3H), 6.67 (m, 2H), 2.57 (m, 3H), 2.46 (m, 4H), 2.21 (m, 8H), 2.15 (m, 3H), 1.55 (m, 4H), 1.48 (m, 14H), 1.23 (m, 4H).

$^{13}$CNMR (126 MHz, DMSO-$d_6$, δ, ppm) δ 174.83, 174.78, 156.80, 156.66, 155.33, 154.68, 153.07, 151.92, 151.37, 150.95, 148.49, 148.43, 148.41, 148.37, 148.19, 148.03, 147.90, 147.88, 147.84, 147.68, 147.53, 147.36, 147.32, 147.18, 147.09, 147.03, 146.90, 146.90, 146.87, 146.82, 146.76, 146.73, 146.69, 146.58, 146.51, 146.40, 146.39, 146.15, 145.96, 145.93, 145.75, 137.28, 136.96, 136.83, 136.52, 129.86, 129.83, 129.72, 129.53, 129.38, 129.33, 129.22, 129.17, 129.05, 129.04, 128.79, 128.70, 128.51, 128.36, 128.17, 128.02, 127.65, 127.63, 127.63, 127.55, 127.38, 127.28, 127.04, 64.81, 61.06, 60.82, 58.69, 58.10, 57.04, 40.80, 40.52, 40.35, 40.19, 40.02, 39.85, 39.69, 39.52, 34.70, 34.01, 33.97, 30.68, 24.37, 24.32.

Molecular formula: $C_{115}H_{67}ClO_{10}$; and MS (MALDI-TOF), m/z: 1641.7.

4. A Preparation Method for Compound 5 is as Follows:

$C_{60}C_6$ (200 mg, 0.214 mmol, 1 equiv) and methyl 3-(4-biphenyl)propionate (1.286 g, 5.36 mmol, 25 equiv) were dissolved in 50 mL of nitrobenzene under water-free and oxygen-free conditions, then 0.1 mL of $SnCl_4$ was added, and a reaction was conducted at 90° C. for 2 h. After the reaction was complete, the resulting system was cooled to room temperature, and the reaction product was directly separated through column chromatography with toluene/methanol in a volume ratio of 85/15 as a mobile phase. The solvent was removed through rotary evaporation, then 30 mL of toluene, 30 mL of acetic acid, and 5 mL of hydrochloric acid were added, and the reaction was conducted at 80° C. for 72 h. After the reaction was complete, an organic phase was subjected to extraction with toluene, and the toluene was removed through rotary evaporation, and 300 mL of acetonitrile was added for precipitation. The resulting precipitate was filtered out through suction filtration, washed with n-hexane three times, dried, and then dissolved with a potassium hydroxide solution. The resulting solution was subjected to suction filtration, a filtrate was collected, and hydrochloric acid was added dropwise to the filtrate until a pH of the filtrate was 7.0, such that a red precipitate was produced. The red precipitate was filtered out through suction filtration and then dried to obtain a product 5 (compound 5).

Identification of Compound 5:

$^1$H NMR (500 MHz, DMSO) δ 12.05 (br.s, 5H), 8.04-7.37 (m 20H), 7.25 (m, 5H), 7.18 (m, 5H), 3.37 (m, 10H), 2.81 (m, 10H), 2.30 (m, 5H), 1.23 (m, 5H).

$^{13}$C NMR (126 MHz, DMSO) δ 174.13, 174.11, 150.68, 150.23, 149.75, 149.59, 149.03, 148.81, 148.67, 148.34, 148.07, 147.81, 147.53, 147.35, 147.21, 146.69, 146.23, 145.70, 145.55, 145.15, 144.74, 144.59, 144.15, 143.85, 143.52, 143.16, 142.84, 142.61, 142.52, 142.08, 141.55, 141.15, 140.92, 140.79, 140.70, 140.63, 140.53, 140.45, 140.28, 140.13, 140.06, 139.68, 139.46, 139.30, 138.96, 138.57, 137.89, 137.80, 137.50, 136.48, 133.43, 132.63, 132.17, 130.58, 129.48, 129.35, 129.26, 129.11, 129.03, 128.94, 128.79, 128.65, 127.21, 127.07, 127.01, 126.85, 126.75, 126.70, 125.95, 125.76, 40.52, 40.35, 40.18, 40.02, 39.85, 39.68, 39.52, 37.82, 35.50, 30.42, 29.49, 26.33, 22.70, 21.51, 20.90.

Molecular formula: $C_{135}H_{65}ClO_{10}$; and MS (MALDI-TOF), m/z: 1847.3

5. A Preparation Method for Compound 6 is as Follows:

$C_{60}Cl_6$ (200 mg, 0.214 mmol, 1 equiv) and 3-(4-biphenyl) propionic acid (1.211 g, 5.36 mmol, 25 equiv) were dissolved in 50 mL of nitrobenzene under water-free and oxygen-free conditions, then 0.1 mL of $SnCl_4$ was added, and a reaction was conducted at 90° C. for 2 h. After the reaction was complete, the resulting system was cooled to room temperature, and 300 mL of acetonitrile was added for precipitation. The resulting precipitate was filtered out through suction filtration, washed with n-hexane three times, dried, and then dissolved with a potassium hydroxide solution. The resulting solution was subjected to suction filtration, a filtrate was collected, and hydrochloric acid was added dropwise to the filtrate until a pH of the filtrate was 7.0, such that a red precipitate was produced. The red precipitate was filtered out through suction filtration and then dried to obtain a product 6 (compound 6).

Identification of Compound 6:

$^1$H NMR (500 MHz, DMSO) δ 12.08 (br.s, 6H), 8.14-7.47 (m 24H), 7.35-6.78 (m, 24H), 3.37 (m, 12H), 2.77 (m, 12H), 2.30-1.22 (m, 12H).

$^{13}$C NMR (126 MHz, DMSO) δ 174.14, 174.14, 174.12, 150.01, 149.36, 148.77, 148.51, 148.24, 147.58, 147.34, 147.24, 146.80, 146.13, 145.52, 145.05, 144.35, 144.03, 143.94, 143.61, 143.50, 142.84, 141.07, 140.99, 140.90, 140.77, 140.50, 140.48, 140.35, 140.23, 140.13, 139.98, 139.48, 138.46, 137.47, 137.35, 137.21, 137.02, 136.89, 136.79, 129.34, 129.25, 129.22, 129.14, 129.09, 129.06, 128.92, 127.98, 127.31, 127.17, 127.12, 127.07, 127.01, 126.94, 126.89, 126.83, 126.78, 126.73, 126.64, 126.49, 126.33, 126.16, 116.13, 40.48, 40.31, 40.14, 39.98, 39.81, 39.64, 39.48, 35.59, 35.49, 31.74, 30.38, 29.54, 29.48, 29.43, 29.32, 29.29, 29.04, 27.02.

Molecular formula: $C_{150}H_{78}O_{12}$; and MS (MALDI-TOF), m/z: 2072.3

6. A Preparation Method for Potassium Salts of Compounds 1 to 6 is as Follows:

The polyaryl carboxylic fullerene derivatives 1 to 6 (0.07 mmol, 1 equiv) each were added to distilled water (20 mL), anhydrous potassium carbonate (24.2 mg, 0.175 mmol, 2.5 eqiv) was added, and the resulting mixture was stirred until solids were completely dissolved. The resulting solution was then filtered through a PES syringe filter (with an average pore size of 0.45 m) and lyophilized for 8 h to finally obtain a powdered potassium salt.

Example 2 Toxicity Evaluation and Drug Activity Evaluation

1. Evaluation of Toxicity of the Water-Soluble Polyaryl Carboxylic Fullerene Derivative for Vero E6 Cells Method:

The potassium salt of the polyaryl carboxylic fullerene derivative 4 (namely, the potassium salt of compound 4) was completely dissolved in water to obtain an orange-red solution, and the orange-red solution was filtered to remove a small amount of an orange-red precipitate and then thoroughly shaken until the solution was clear. A monolayer of Vero E6 cells on a 96-well plate was washed once with phosphate-buffered saline (PBS), the resulting supernatant was discarded, and the potassium salt of the water-soluble polyaryl carboxylic fullerene derivative (namely, the potassium salt of compound 4) fold-diluted was added. In the normal cell group, an equal volume of a medium was added to each well. The cells were cultivated at 37° C. and 5% $CO_2$ for 4 d to 5 d. A cytopathic effect (CPE) was observed and recorded under a microscope, and an inhibition rate was calculated. The medium was 10% fetal bovine serum (FBS)-containing DMEM.

Figure 2:
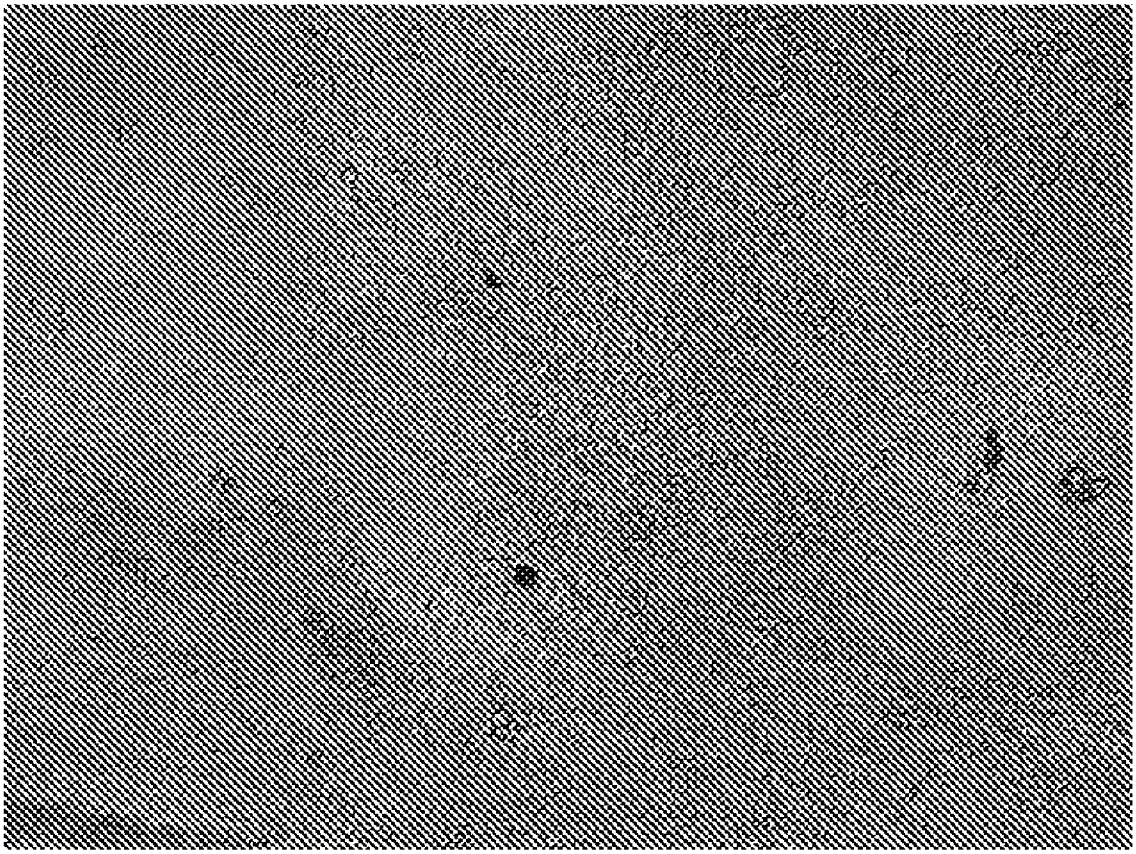
FIG. 2 shows the survival results of African green monkey kidney (AGMK) cells in the presence of a potassium salt of a polyaryl carboxylic fullerene derivative 4 (compound 4) in an embodiment of the present disclosure at a concentration of 109.2 μM.

Results:

The potassium salt of the polyaryl carboxylic fullerene derivative 4 (namely, the potassium salt of compound 4) exhibited no toxicity for AGMK cells (Vero E6) (as shown in FIG. 2) when at a concentration as high as 109.2 M.

2. Evaluation of Efficacy of the Water-Soluble Polyaryl Carboxylic Fullerene Derivative for a Novel Coronavirus (SARS-CoV-2)

Method:

Preventive Medication Model: CPE Reduction Assay

A monolayer of Vero E6 cells were washed once with PBS, the potassium salt of the polyaryl carboxylic fullerene derivative was added to each well at a specified concentration, and controls were set. The cells were incubated at 37° C. for 2 h, infected with a novel coronavirus (SARS-CoV-2) at a dose of about 100 TCID50, and incubated for 2 h. The used medium was replaced with a fresh medium, and the cells were further cultivated at 37° C. for 2 d.

A fresh medium treated with the potassium salt of the polyaryl carboxylic fullerene derivative at a specified concentration (maintaining the concentration of the polyaryl carboxylic fullerene derivative) was used to further cultivate the cells for 2 d to 3 d. CPE was observed and recorded under a microscope, and a median effective concentration ($IC_{50}$) was calculated by the Reed-Muench method.

Figure 3A:
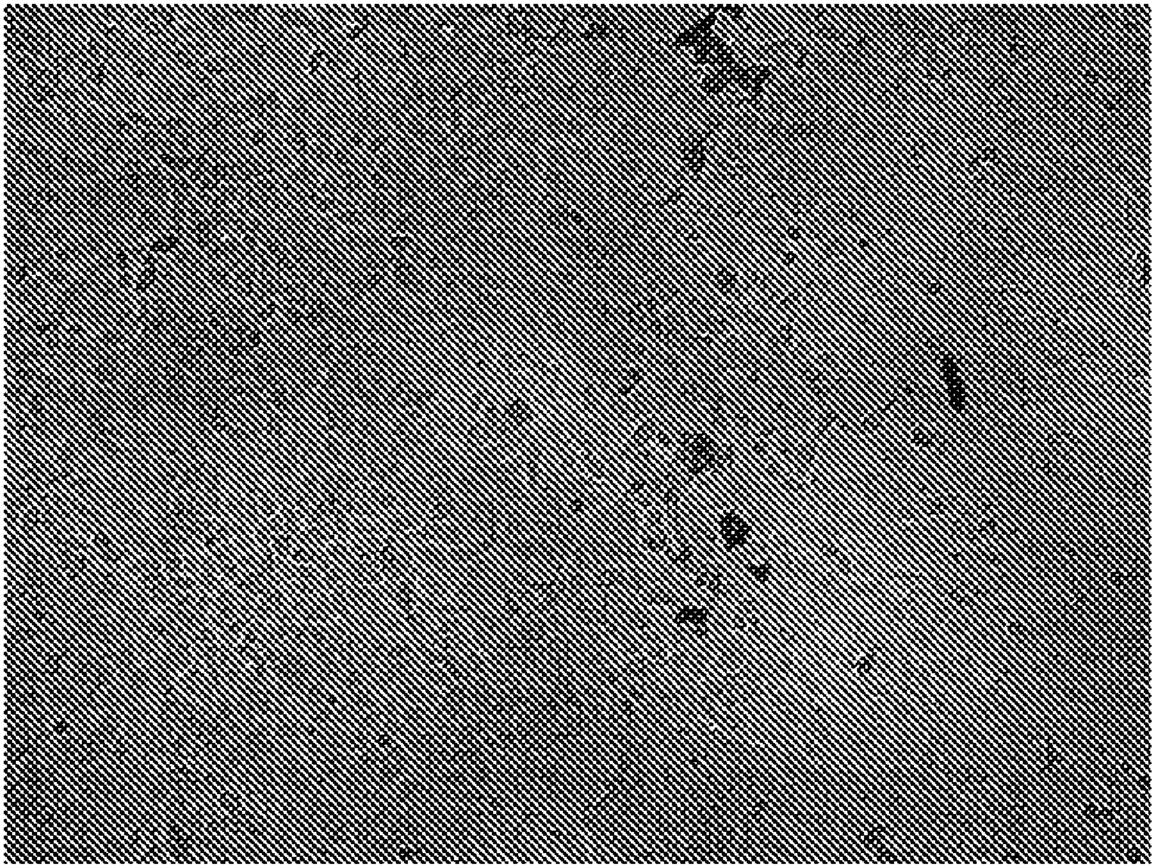
FIGS. 3A-3C show the inhibition results of a potassium salt of a polyaryl carboxylic fullerene derivative 4 (compound 4) in an embodiment of the present disclosure on a novel coronavirus (SARS-CoV-2) at a concentration of 54.6 μM (3 replicates)
Figure 3B:
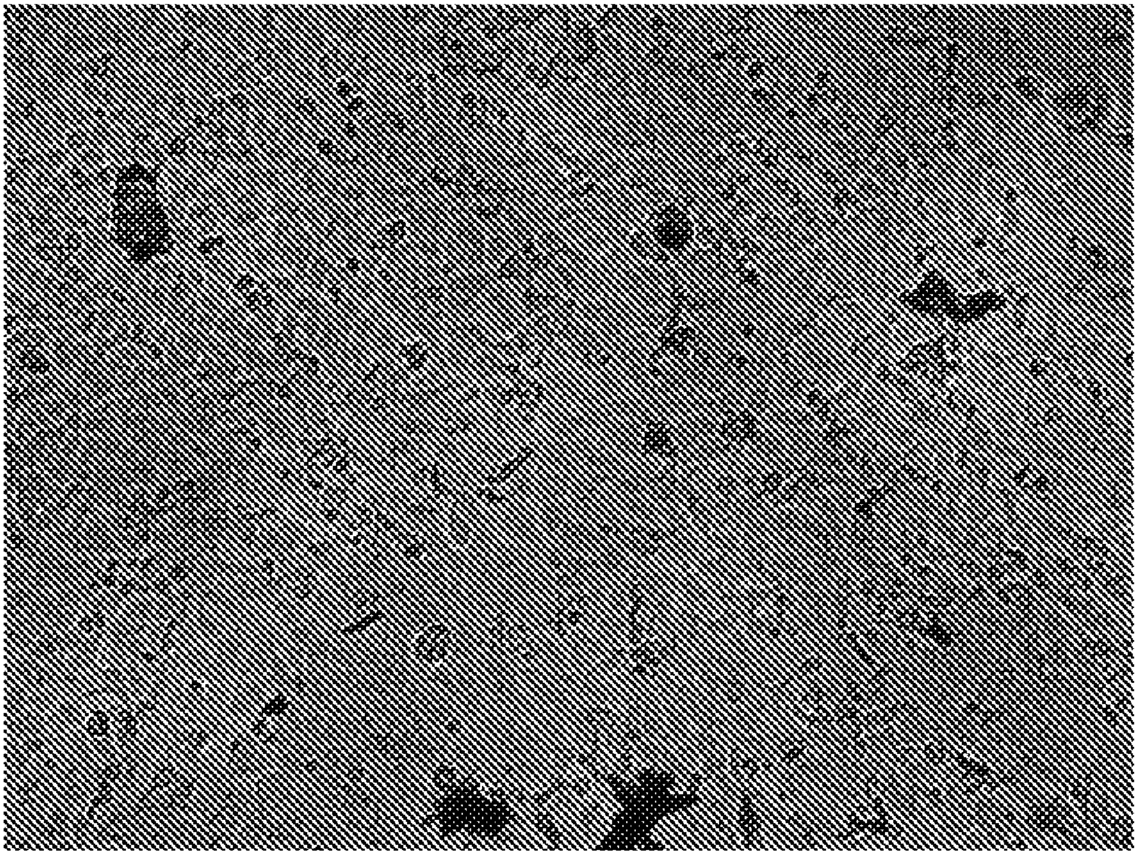
Figure 3C:
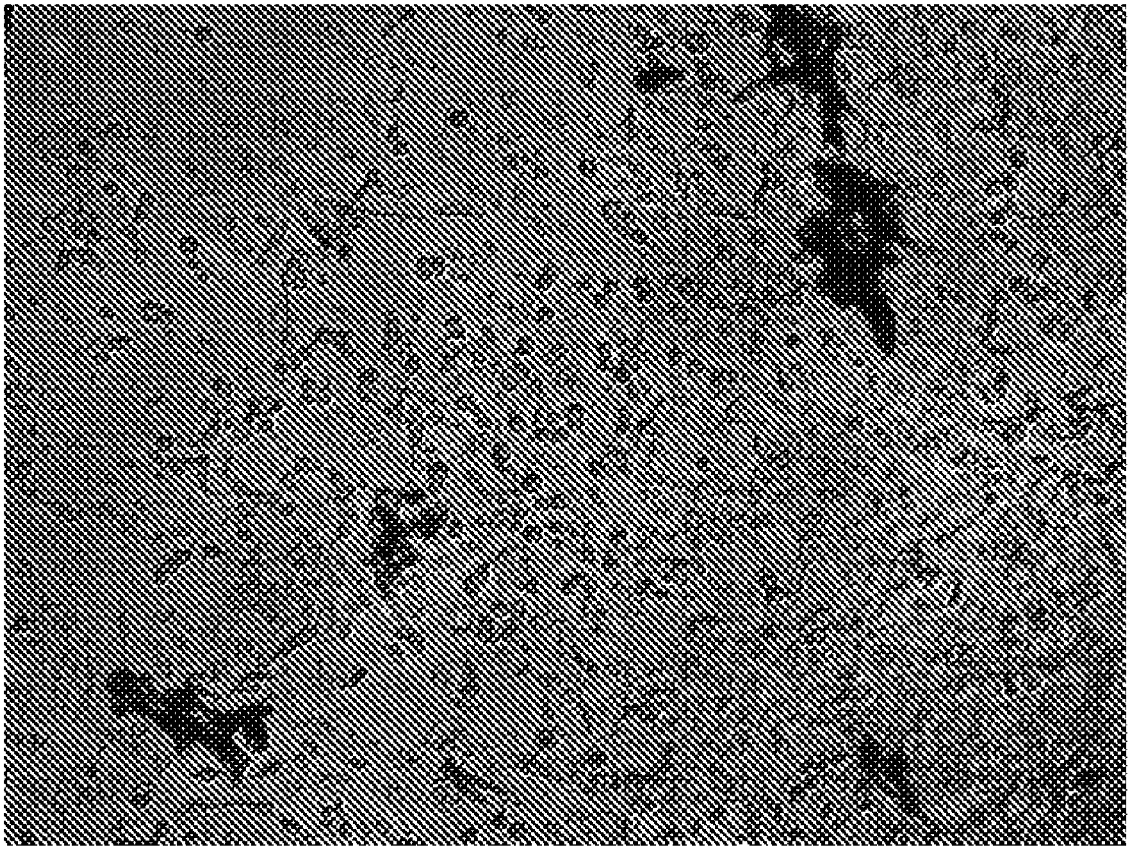
Figure 4:
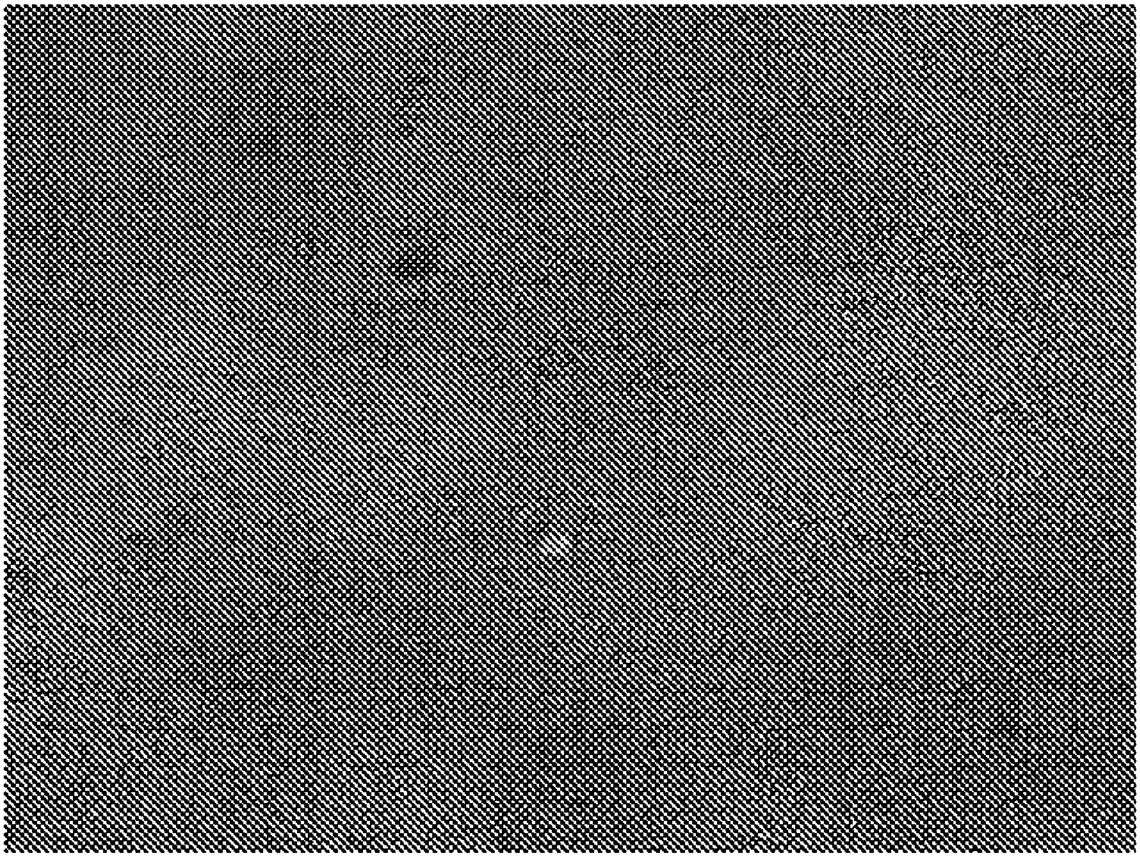
FIG. 4 shows the control results of AGMK cells in the absence of a viral infection and a polyaryl carboxylic fullerene derivative 4 (compound 4) according to an embodiment of the present disclosure.
Figure 5:
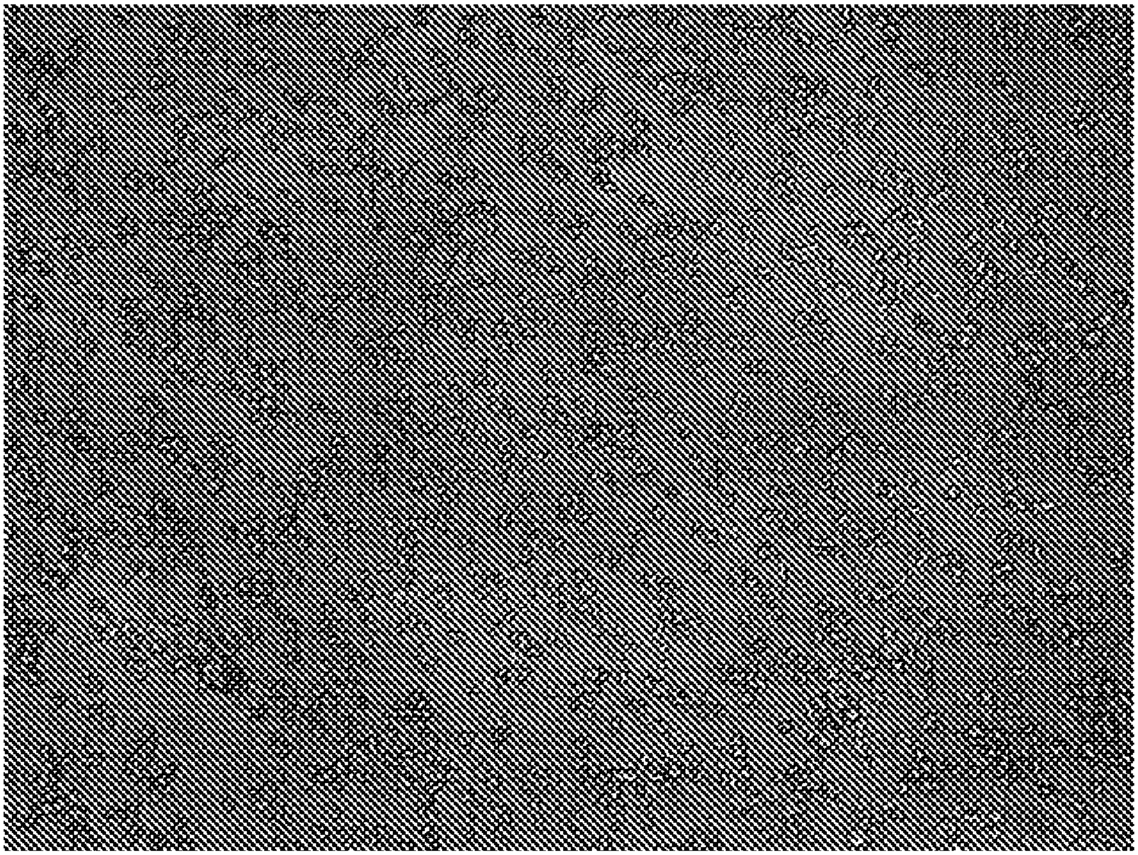
FIG. 5 shows the control results of novel coronavirus (SARS-CoV-2)-infected AGMK cells in the absence of a polyaryl carboxylic fullerene derivative 4 (compound 4) according to an embodiment of the present disclosure.

Results:

The efficacy of the potassium salt of the water-soluble polyaryl carboxylic fullerene derivative 4 (namely, the potassium salt of compound 4) was evaluated by an AGMK cell (Vero) CPE inhibition method, and the median effective concentration ($IC_{50}$) of the derivative for the novel coronavirus (SARS-CoV-2) was about 54.6 μM (inhibition results of 3 parallel experiments were shown in FIGS. 3A-3C, and experimental results of the controls were shown in FIG. 4 and FIG. 5).

3. Evaluation of Toxicity of the Water-Soluble Polyaryl Carboxylic Fullerene Derivative for BHK21-hACE2 Cells Method:

The potassium salts of all water-soluble polyaryl carboxylic fullerene derivatives (namely, potassium salts of compounds 1 to 6) each were diluted to 1,000 M. Diluted analytes were then prepared by a serial double dilution method. 80 L of a diluted fullerene compound solution was mixed with 20 L of an rVSV-SARS-2 pseudovirus, the resulting mixture was added to pre-cultivated BHK21-hACE2 cells (80 μL per well), and the cells were incubated for 12 h. The resulting supernatant was removed, then a mixture of 10 L of a cck-8 solution and 100 μL of a medium was added, and the cells were cultivated for 2 h; the absorbance at 450 nm was determined. A reduction rate (%) of the absorbance was used to indicate the cytotoxicity of the compound.

Results:

The cytotoxicity experiments showed that the potassium salts of the water-soluble polyaryl carboxylic fullerene derivatives (namely, the potassium salts of compounds 1 to 6) exhibited no toxicity for BHK21-hACE2 cells when at a concentration as high as 1,000 M.

4. Evaluation of Efficacy of the Water-Soluble Polyaryl Carboxylic Fullerene Derivative for an rVSV-SARS2 Pseudocoronavirus Method:

BHK21-hACE2 cells were plated on a 96-well plate at $2\times10^4$ cells/well, such that a cell density could reach 70% to 80% after the cells were cultivated for 12 h. The potassium salts of the water-soluble polyaryl carboxylic fullerene derivatives (namely, the potassium salts of compounds 1 to 6, 2 mM) each were diluted as follows: 10 μl of the potassium salt (2 mM) of the water-soluble polyaryl carboxylic fullerene derivative was mixed with 90 μl of DMEM to obtain a sample solution with a final concentration of 0.2 mM, 50 μl of the 0.2 mM sample solution was taken and mixed with 150 μl of DMEM to obtain a sample solution of gradient 1, 50 μl of the sample solution of gradient 1 was taken and mixed with 100 μl of DMEM to obtain a sample solution of gradient 2, and 3-fold dilution was conducted in turn to obtain 8 gradients in total. 80 μl of the potassium salt of the water-soluble polyaryl carboxylic fullerene derivative diluted at each gradient was taken and mixed with 20 μl of an rVSV-SARS-2 (3×10e5 pfu/mL), and the resulting mixture was thoroughly mixed and then incubated at 37° C. for 1 h. A culture supernatant of BHK21-hACE2 cells was removed, and 100 μl of a sample obtained after the incubation of 80 μl of the water-soluble polyaryl carboxylic fullerene derivative and 20 μl of rVSV-SARS-2 was added. 12 h later, the number of positive cells was recorded under a microscope, and CPE was recorded.

Results:

The efficacy of the potassium salts of the water-soluble polyaryl carboxylic fullerene derivatives was evaluated by a BHK21-hACE2 cell CPE inhibition method, and median effective concentrations ($IC_{50}$) of the derivatives for the pseudocoronavirus (rVSV-SARS-2) were 79.6 μM, 83.7 μM, 189.3 μM, 65.8 μM, 42.2 μM, and 8.5 μM, respectively (as shown in Table 2).

TABLE 2

Efficacy of the potassium salts of the water-soluble polyaryl carboxylic fullerene derivatives evaluated by the BHK21-hACE2 cell CPE inhibition method

| Compound | 1 | 2 | 3 | 4 | 5 | 6 |
|---|---|---|---|---|---|---|
| $IC_{50}$/rVSV-SARS-2 (μM) | 79.6 | 83.7 | 189.3 | 65.8 | 42.2 | 8.5 |

Example 3 Assembly of the Polyaryl Carboxylic Fullerene Derivatives in Solutions in the Form of Vesicles Method:

1 mg of a polyaryl carboxylic fullerene derivative powdery sample was weighed and added to 1 mL of a solvent (compounds 1 to 3 each were added to DMF, and compound 4 was added to acetonitrile), and the resulting mixture was subjected to an ultrasonic treatment at 30° C. to 40° C. for 1 h to 2 h to obtain a solution in which the polyaryl carboxylic fullerene derivative powdery sample was dissolved; the solution was then added dropwise to a silicon wafer, and after the solvent was evaporated, a layer of platinum of about 10 nm was sprayed onto the surface of the sample, and then the sample was observed under a scanning electron microscope.

Figure 6A:
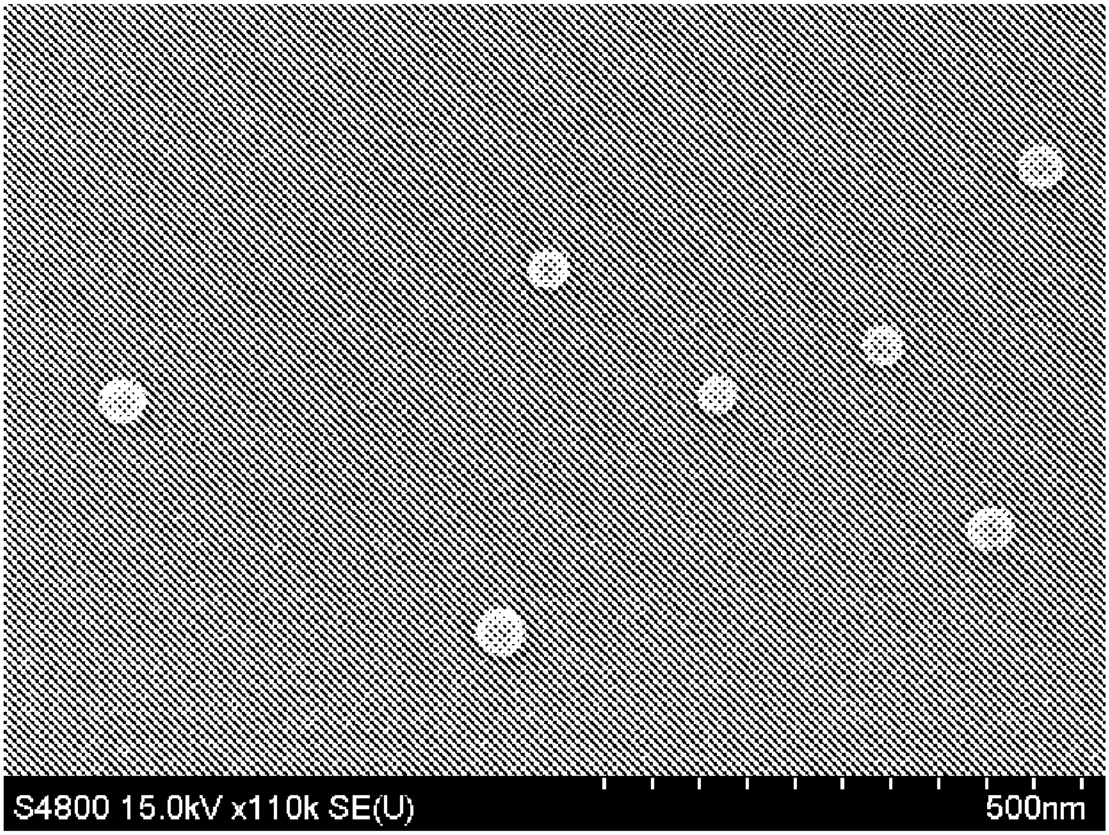
FIGS. 6A-6B show scanning electron microscopy (SEM) images of a vesicle according to an embodiment of the present disclosure.
Figure 6B:
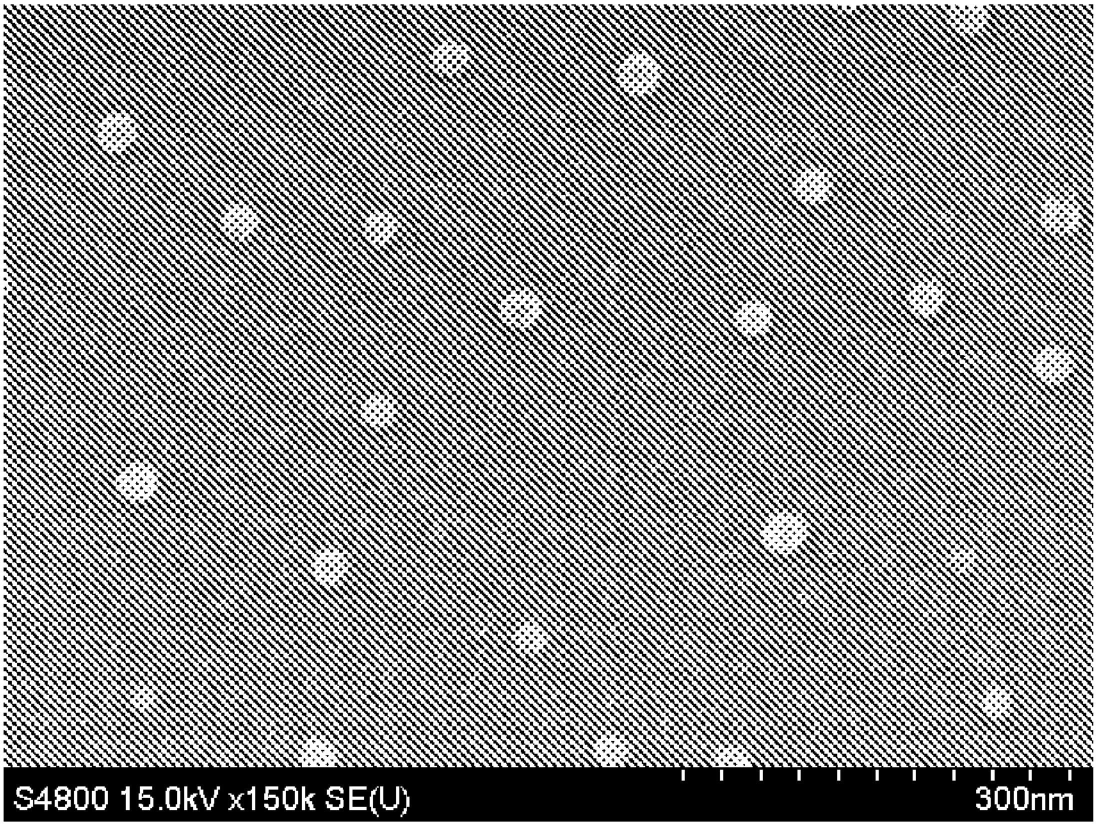
Figure 7A:
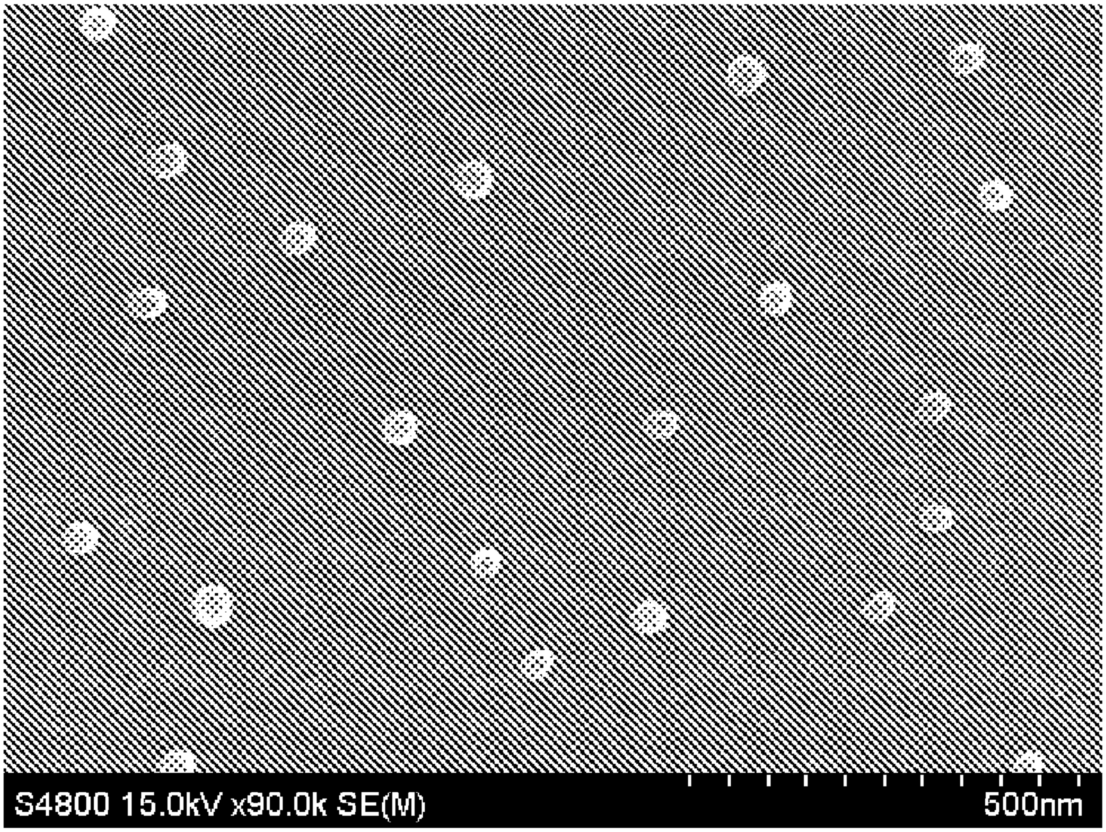
FIGS. 7A-7B show SEM images of a vesicle according to another embodiment of the present disclosure.
Figure 7B:
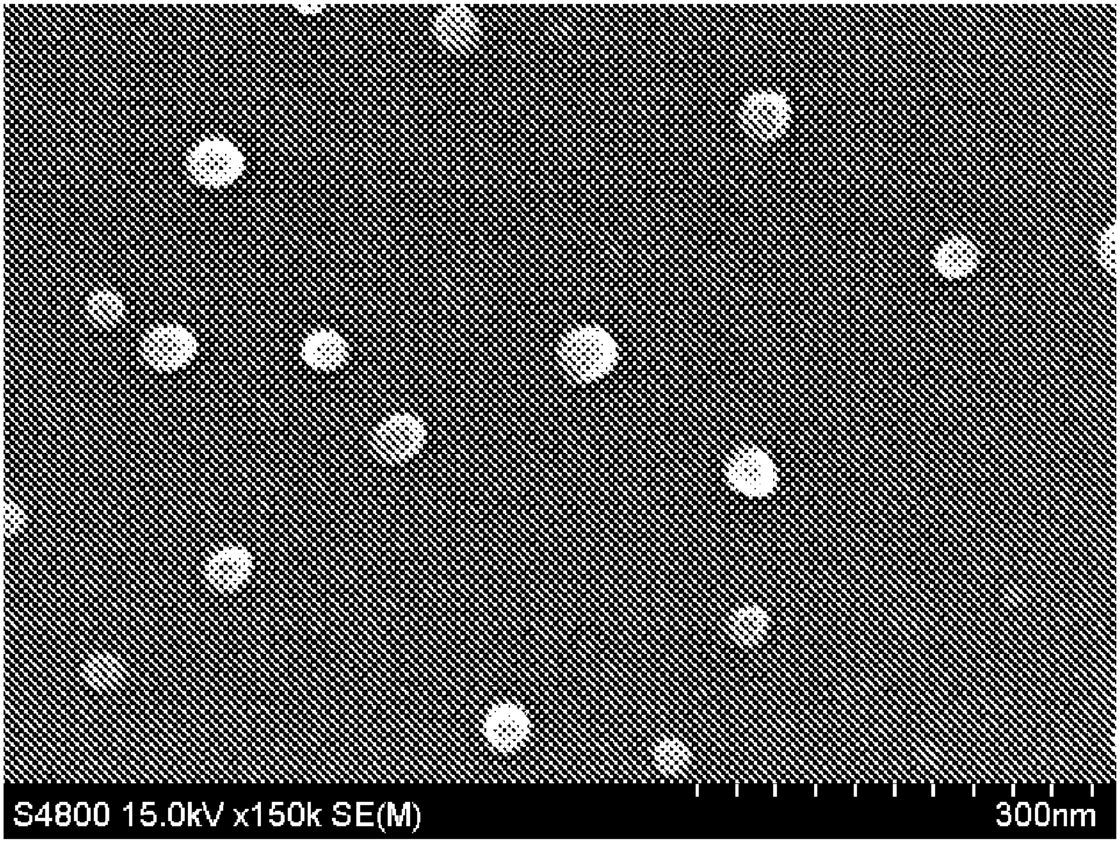
Figure 8A:
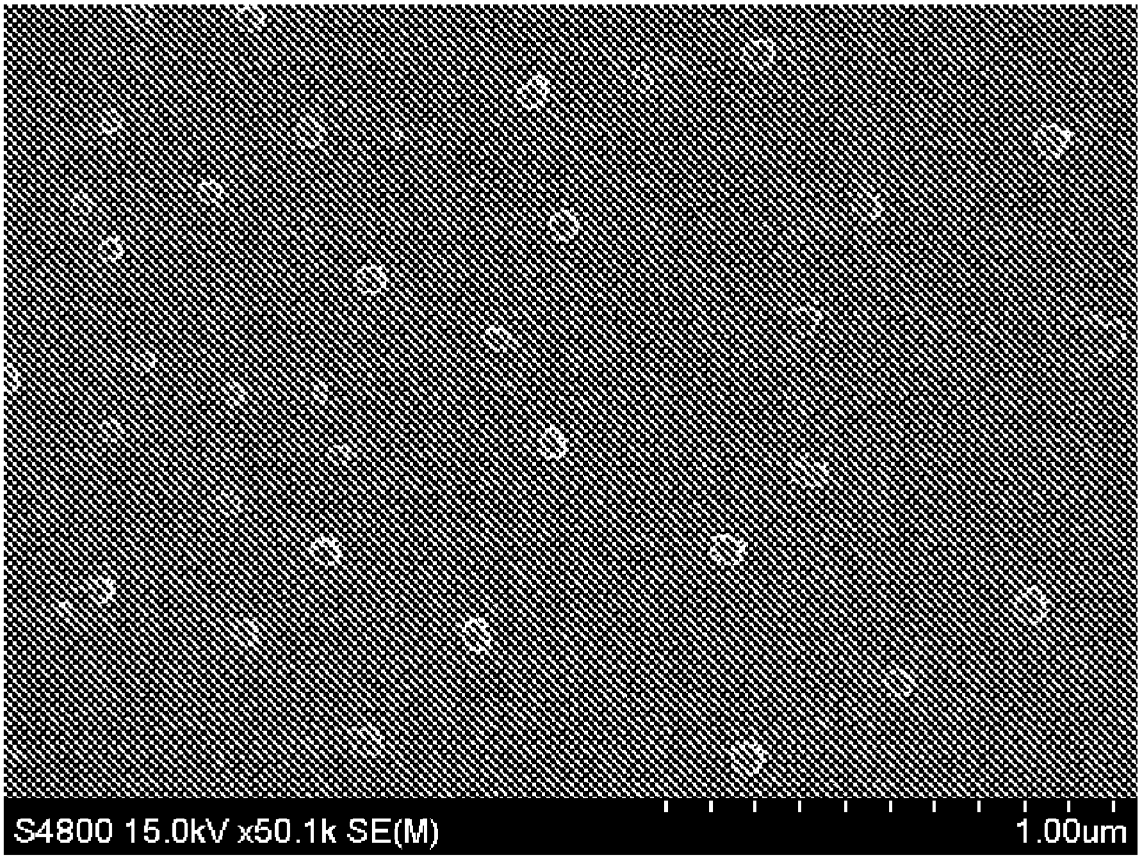
FIGS. 8A-8B show SEM images of a vesicle according to another embodiment of the present disclosure.
Figure 8B:
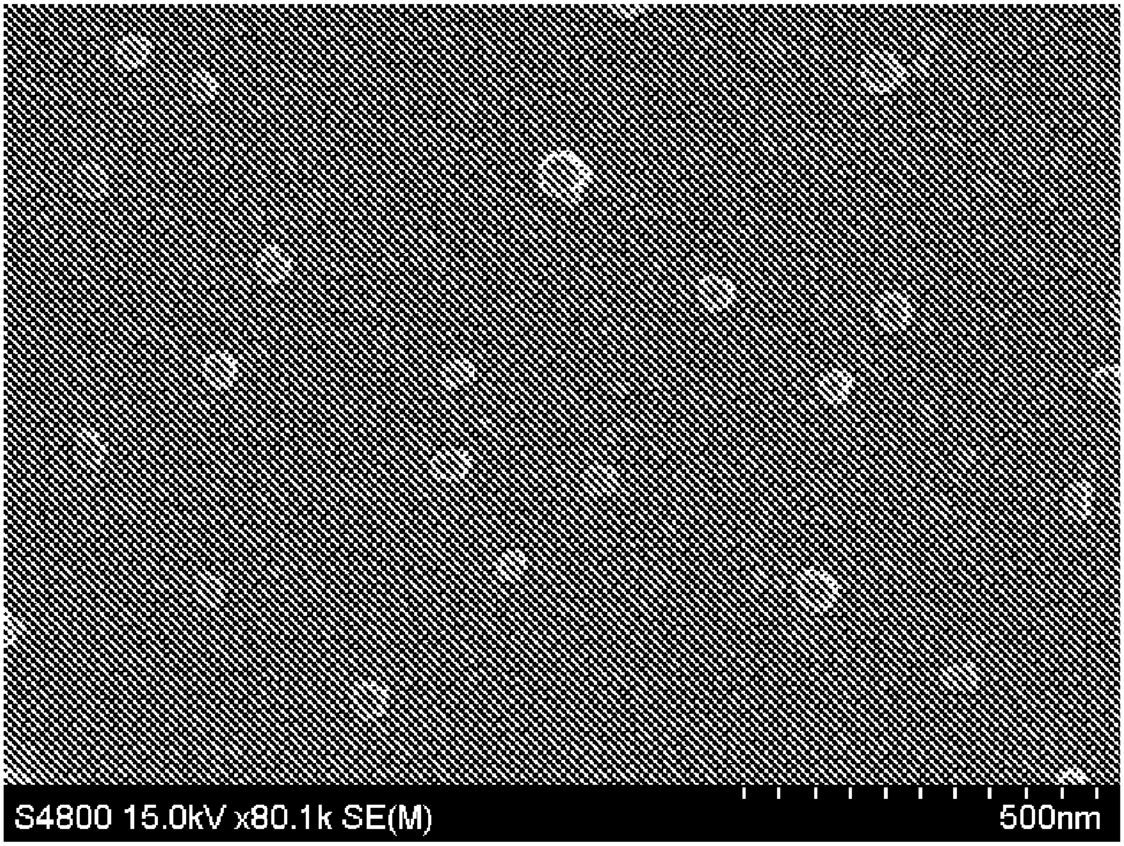

Results:

A Tyndall phenomenon could be observed after the polyaryl carboxylic fullerene derivatives 1 to 6 each were dissolved in the respective solvent. SEM results showed that vesicles formed by compound 1 had a particle size of 60 nm to 70 nm (as shown in FIGS. 6A-6B); vesicles formed by compound 3 had a particle size of 40 nm to 50 nm (as shown in FIGS. 7A-7B); and vesicles formed by compound 4 had a particle size of about 40 nm (as shown in FIGS. 8A-8B), indicating that such compounds each assembled in the form of vesicles in a specified solution.

What is claimed is:

1. A compound of a general formula shown in formula A:

fullerene-$RR_1R_2R_3R_4R_5$ formula A or a stereoisomer, prodrug, pharmaceutically acceptable salt, or pharmaceutically acceptable solvate of the compound, wherein fullerene in the formula A is a cage-like all-carbon structure comprising a five-membered carbon ring, a six-membered carbon ring, and/or a seven-membered carbon ring and/or a four-membered carbon ring, or the fullerene is a metal or cluster-embedded structure;

the fullerene is selected from the group consisting of $C_{60}$, $C_{70}$, $C_{84}$, $C_{90}$, and $C_{100}$;

wherein

R is selected from the group consisting of the following:

(1) H, F, Cl, Br, I, $C_1$-$C_6$ alkyl, and $C_1$-$C_6$ alkoxy;

(2)

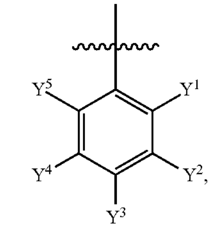

wherein $Y^1$, $Y^2$, $Y^3$, $Y^4$, and $Y^5$ are not all H and each are independently selected from the group consisting of the following:

1) H, and

2)

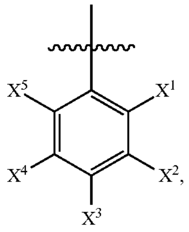

wherein $X^1$, $X^2$, $X^3$, $X^4$, and $X^5$ each are independently selected from the group consisting of H and $C_1$-$C_6$ alkyl substituted with 1, 2, or 3 carboxyl groups, and $X^1$, $X^2$, $X^3$, $X^4$, and $X^5$ are not all H;

and (3)

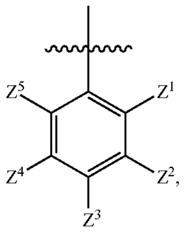

wherein $Z^1$, $Z^2$, $Z^3$, $Z^4$, and $Z^5$ each are independently selected from the group consisting of H and $C_1$-$C_6$ alkyl substituted with 1, 2, or 3 carboxyl groups, and $Z^1$, $Z^2$, $Z^3$, $Z^4$, and $Z^5$ are not all H;

$R^1$, $R^2$, $R^3$, $R^4$, and $R^5$ each are independently selected from the group consisting of the following:

(1),

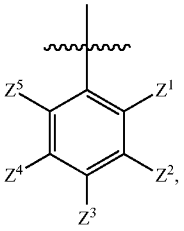

wherein $Z^1$, $Z^2$, $Z^3$, $Z^4$, and $Z^5$ each are independently selected from the group consisting of H and $C_1$-$C_6$ alkyl substituted with 1, 2, or 3 carboxyl groups, and $Z^1$, $Z^2$, $Z^3$, $Z^4$, and $Z^5$ are not all H; and (2)

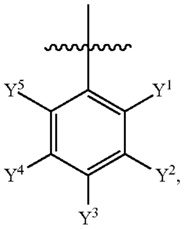

wherein $Y^1$, $Y^2$, $Y^3$, $Y^4$, and $Y^5$ are not all H and each are independently selected from the group consisting of the following:

1) H, and

2)

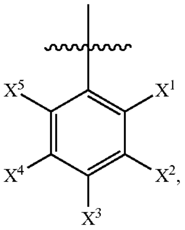

wherein $X^1$, $X^2$, $X^3$, $X^4$, and $X^5$ each are independently selected from the group consisting of H and $C_1$-$C_6$ alkyl substituted with 1, 2, or 3 carboxyl groups, and $X^1$, $X^2$, $X^3$, $X^4$, and $X^5$ are not all H;

the compound shown in formula A does not comprise the following compounds:

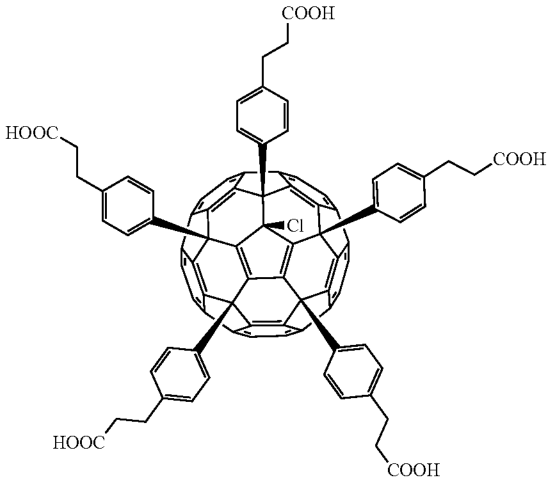

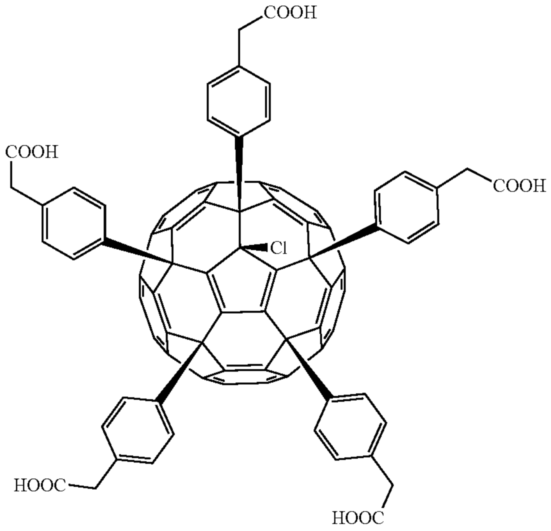

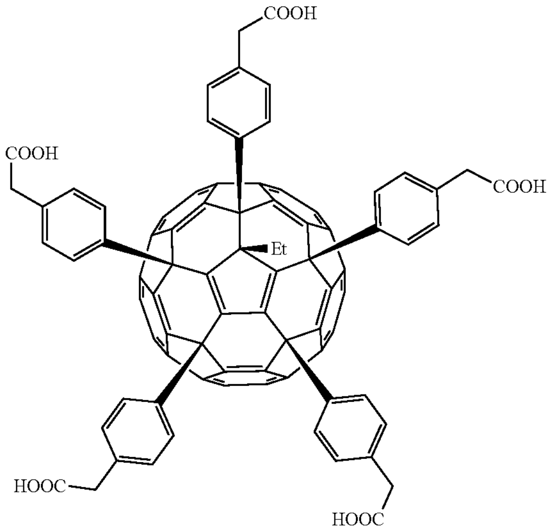

-continued
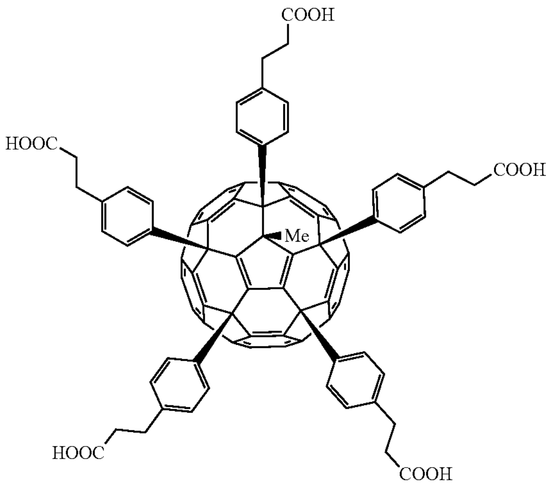
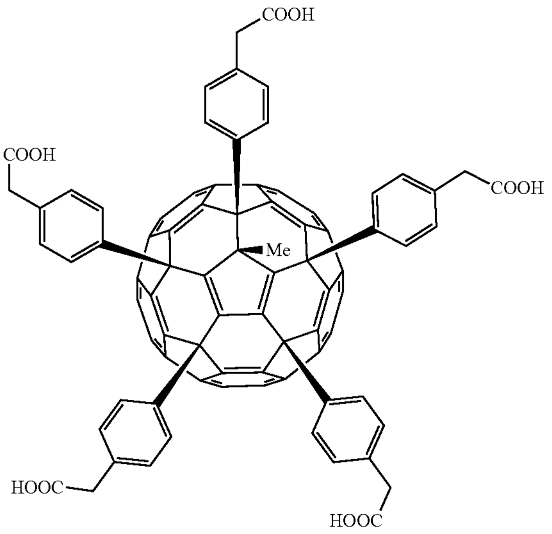
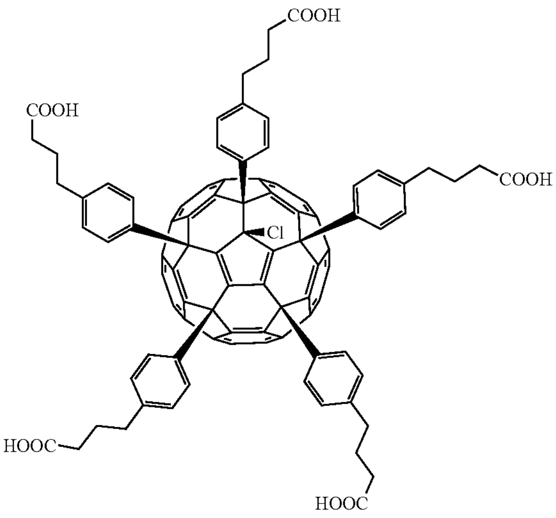
-continued
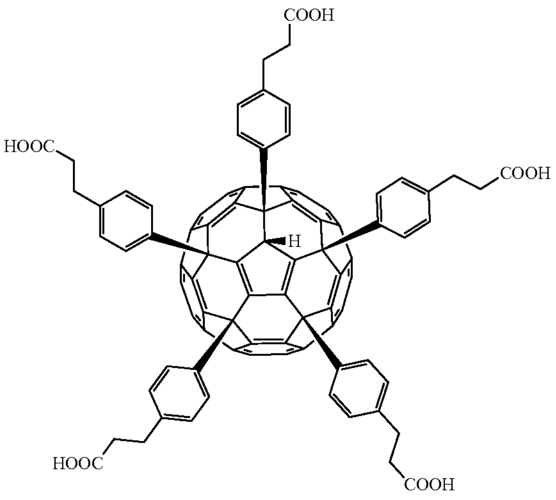
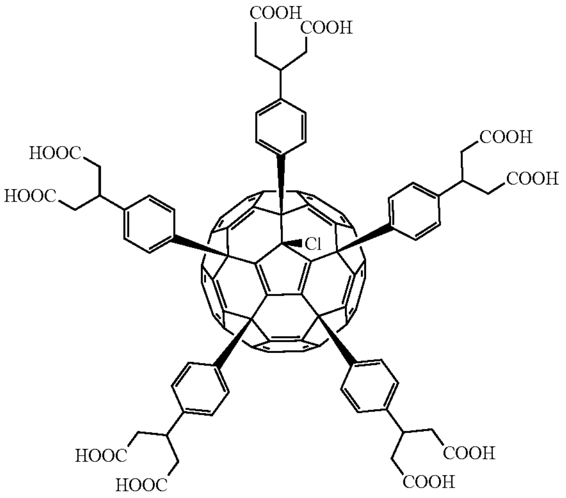
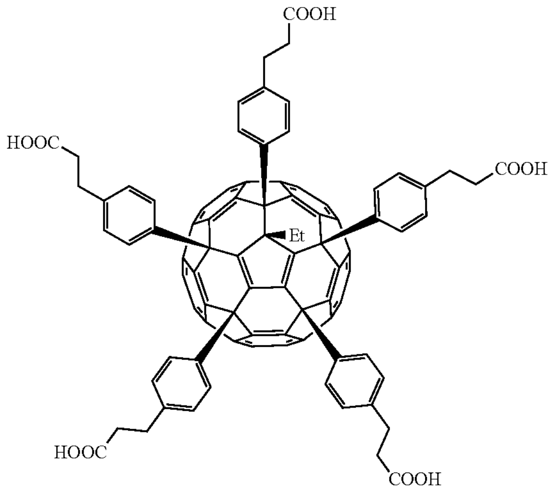

-continued
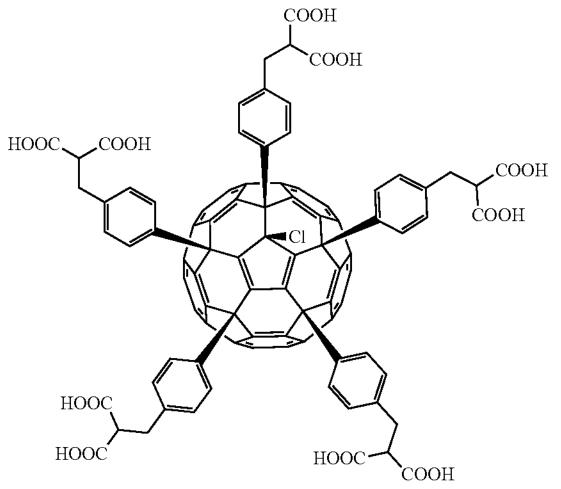
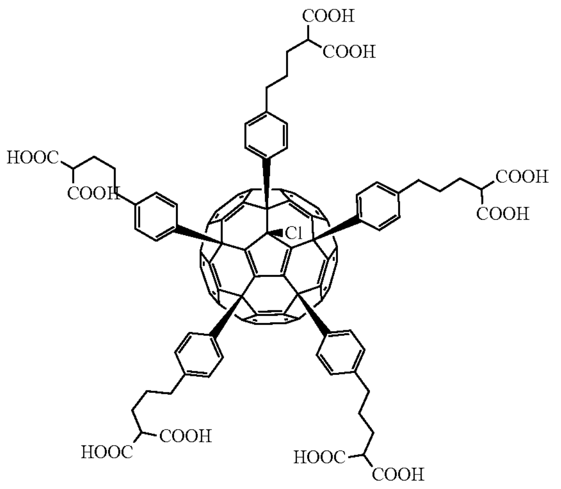
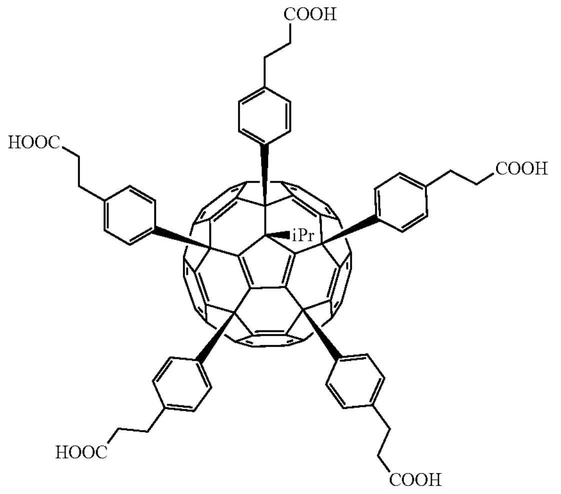
-continued
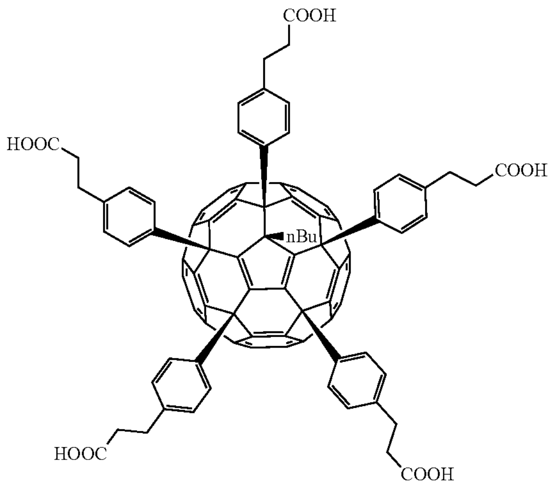
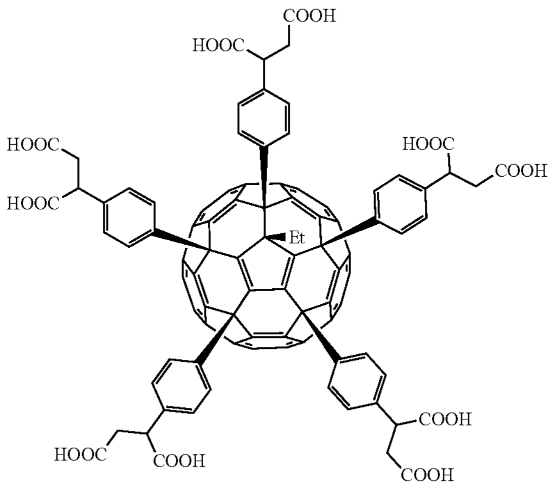
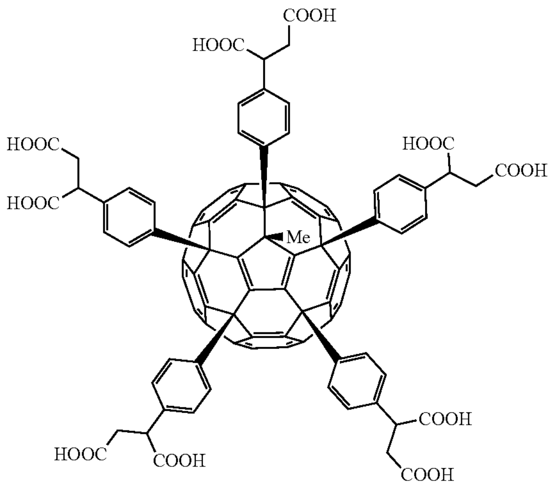

-continued
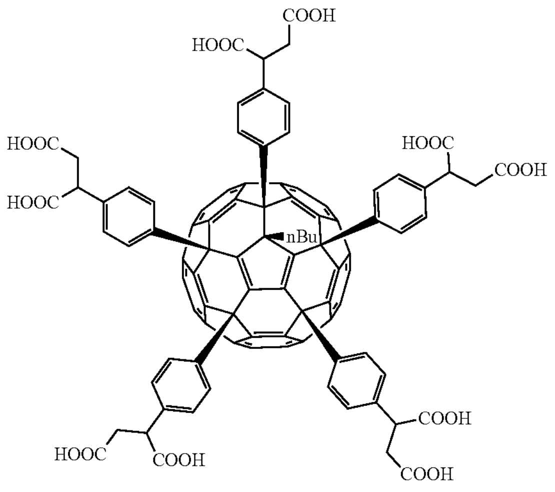
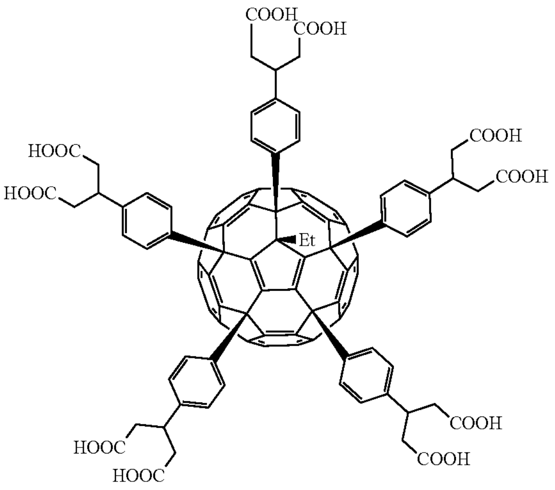
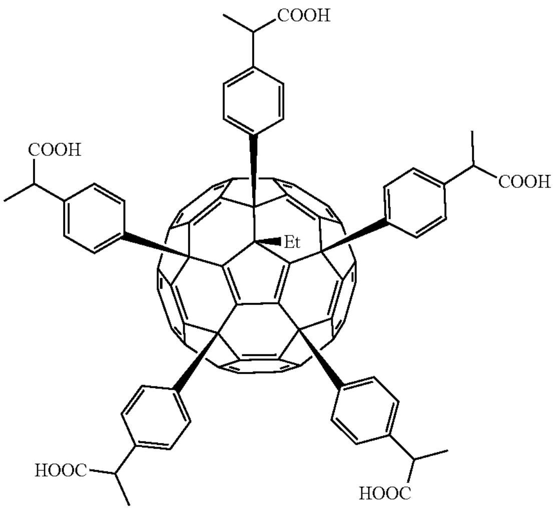
-continued
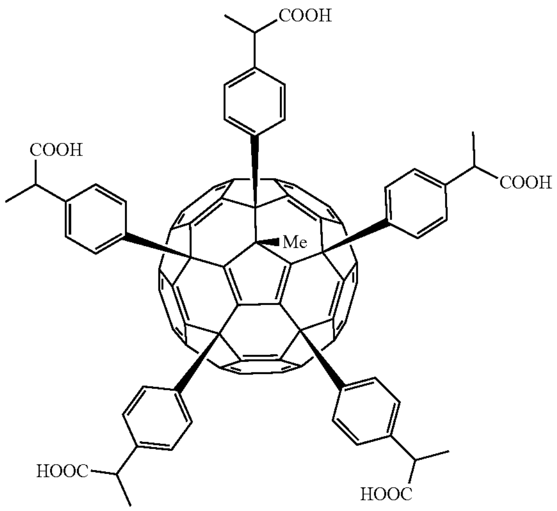
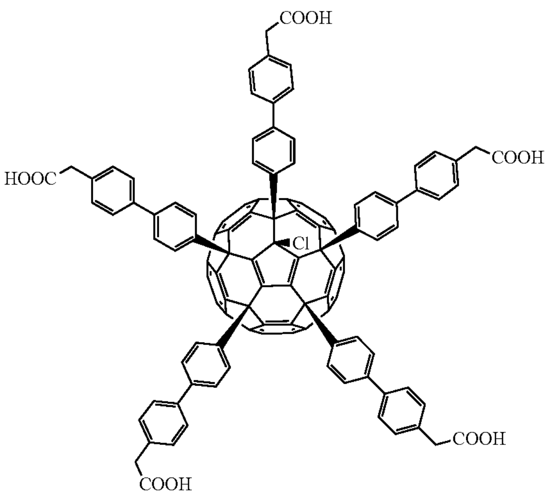
.
2. The compound according to claim 1, wherein R is selected from the group consisting of the following: (1) H, F, Cl, Br, I, $C_1$-$C_6$ alkyl, and $C_1$-$C_6$ alkoxy; and (2)
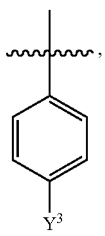
wherein
$Y^3$ is

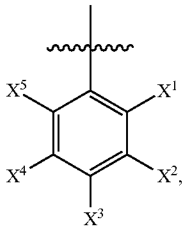

wherein $X^1$, $X^2$, $X^3$, $X^4$, and $X^5$ each are independently selected from the group consisting of H and $C_1$-$C_6$ alkyl substituted with 1, 2, or 3 carboxyl groups, and $X^1$, $X^2$, $X^3$, $X^4$, and $X^5$ are not all H;

or, $Y^3$ is

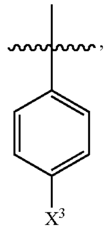

wherein $X^3$ is $C_1$-$C_6$ alkyl substituted with 1, 2, or 3 carboxyl groups; or $R^1$, $R^2$, $R^3$, $R^4$, and $R^5$ each are independently selected from the group consisting of the following:

(1)

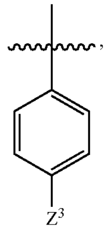

wherein $Z^3$ is independently $C_1$-$C_6$ alkyl substituted with 1, 2, or 3 carboxyl groups; and (2)

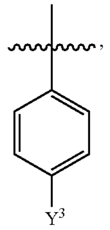

wherein $Y^3$ is

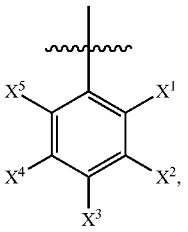

wherein $X^1$, $X^2$, $X^3$, $X^4$, and $X^5$ each are independently selected from the group consisting of H and $C_1$-$C_6$ alkyl substituted with 1, 2, or 3 carboxyl groups, and $X^1$, $X^2$, $X^3$, $X^4$, and $X^5$ are not all H;

or, $Y^3$ is

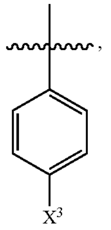

wherein $X^3$ is independently $C_1$-$C_6$ alkyl substituted with 1, 2, or 3 carboxyl groups.

3. The compound according to claim 1, wherein the compound is a compound selected from the group consisting of the following:

| compound No. | compound structure |
| --- | --- |
| 3 | 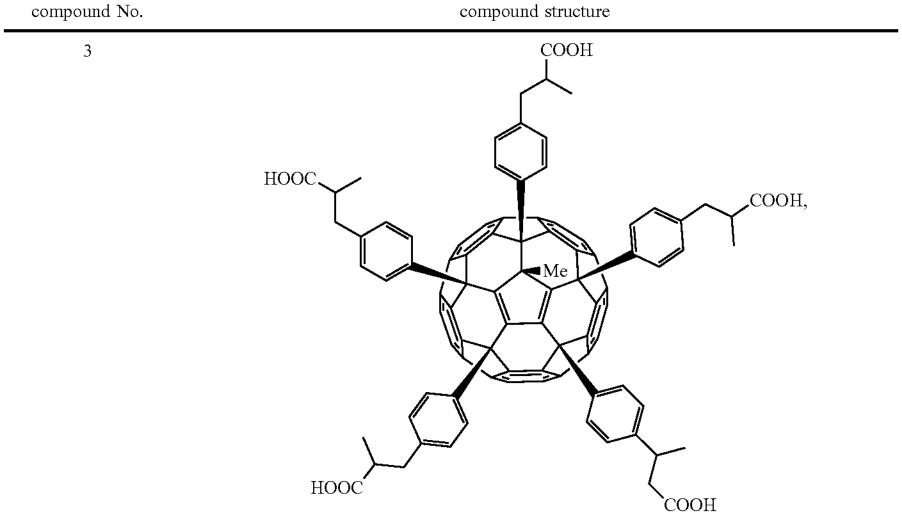 |
| 4 | 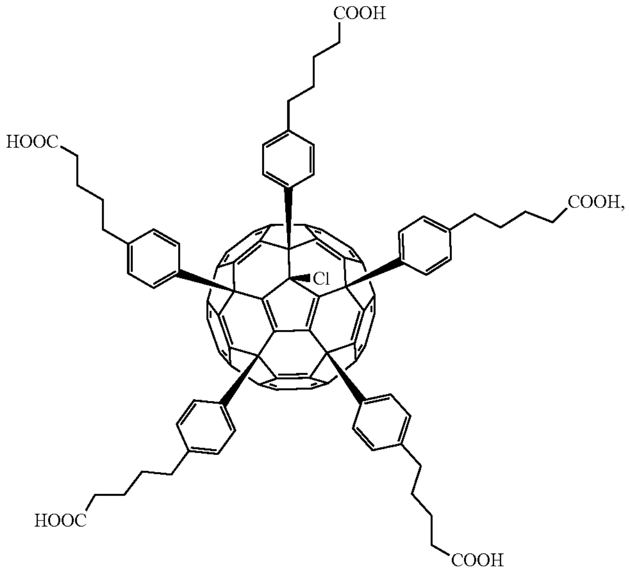 |
| 5 | 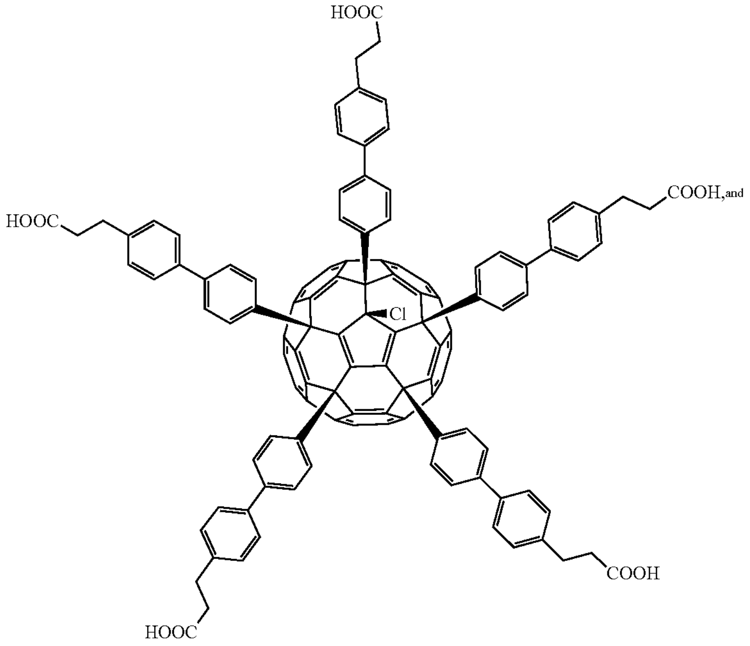 and |

or a stereoisomer, prodrug, pharmaceutically acceptable salt, or pharmaceutically acceptable solvate of the compound 3, the compound 4, the compound 5, or the compound 6.

4. A method for preparing the compound according to claim 3, comprising:

(1) subjecting $C_{60}Cl_6$ to a nucleophilic substitution reaction with α-methylhydrocinnamic acid, 5-phenylvaleric acid, or 3-(4-biphenyl)propionic acid to obtain the compound; or subjecting $C_{60}Cl_6$ to a nucleophilic substitution reaction with methyl 3-(4-biphenyl)propionate to obtain a first resulting reaction system, and after the nucleophilic substitution reaction is complete, cooling the first resulting reaction system to room temperature, and subjecting a product of the nucleophilic substitution reaction to a hydrolysis reaction to obtain the compound, wherein a molar ratio of the α-methylhydrocinnamic acid, the 5-phenylvaleric acid, the methyl 3-(4-biphenyl) propionate, or the 3-(4-biphenyl)propionic acid to the $C_{60}Cl_6$ is (20-30):1;

the nucleophilic substitution reaction is conducted in the presence of $SnCl_4$;

the nucleophilic substitution reaction is conducted under water-free and oxygen-free conditions;

a solvent for the nucleophilic substitution reaction is nitrobenzene;

the nucleophilic substitution reaction is conducted at 60° C. to 100° C. for 1 h to 3 h;

a solvent for the hydrolysis reaction is toluene;

the hydrolysis reaction is conducted in the presence of acetic acid and hydrochloric acid;

the hydrolysis reaction is conducted at 60° C. to 100° C. for 60 h to 80 h;

before the hydrolysis reaction, the method further comprises: subjecting the product of the nucleophilic substitution reaction to purification, wherein the purification is conducted through column chromatography and a mobile phase for the column chromatography is toluene/methanol in a volume ratio of 85/15; and (2) after the nucleophilic substitution reaction of the $C_{60}Cl_6$ with the α-methylhydrocinnamic acid, the 5-phenylvaleric acid, or the 3-(4-biphenyl)propionic acid in step (1) is complete, cooling a second resulting reaction system to room temperature, adding acetonitrile to the second resulting reaction system for precipitation to obtain a resulting mixture, and subjecting the resulting mixture to filtration to obtain a first filter cake; or after the hydrolysis reaction in step (1) is complete, conducting extraction with toluene, rotary evaporation, adding acetonitrile to a reaction product obtained after the rotary evaporation for precipitation to obtain a resulting mixture, and subjecting the resulting mixture to filtration to obtain a first filter cake;

(3) dissolving the first filter cake with a potassium hydroxide solution to obtain a resulting solution, subjecting the resulting solution to filtration to remove insoluble matters, and collecting a filtrate;

(4) adding hydrochloric acid dropwise to the filtrate for neutralization until a pH of the filtrate is 7.0, such that a precipitate is produced; and (5) subjecting a mixture obtained in step (4) to filtration to obtain a second filter cake, wherein the second filter cake is the compound.

5. A pharmaceutical composition comprising the compound or the stereoisomer, prodrug, pharmaceutically acceptable salt, or pharmaceutically acceptable solvate of the compound according to claim 1 and an optional pharmaceutically acceptable carrier or excipient, wherein the pharmaceutical composition is in a dosage form of a pill, a tablet, a capsule, an aqueous solution, or an aqueous suspension for an oral administration, in a dosage form of a micronized suspension or solution for a topical ocular administration, in a dosage form of a paste, an ointment, a lotion, a spray, or a cream for a topical transdermal or mucosal administration, or in a dosage form of sterile injection water, an oil suspension, or a sterile injection solution for an injection.

6. A vesicle with a diameter of 40 nm to 140 nm, wherein the vesicle is produced using the compound or the pharmaceutically acceptable salt of the compound according to claim 1; and the vesicle is produced by a method comprising:

dissolving the compound or the pharmaceutically acceptable salt of the compound in N,N-dimethylformamide (DMF) or acetonitrile to obtain a solution, and subjecting the solution to an ultrasonic treatment at 30° C. to 40° C. for 1 h to 2 h to obtain the vesicle, wherein a ratio of a mass of the compound or the pharmaceutically acceptable salt of the compound to a volume of the DMF or the acetonitrile is 1 mg:1 mL.

7. A method of preventing and/or treating a disease caused by a coronavirus infection comprising a step of administering a compound shown in formula A or a stereoisomer, prodrug, pharmaceutically acceptable salt, or pharmaceutically acceptable solvate of the compound to a subject in need, wherein the disease is a respiratory disease comprising a simple infection, pneumonia, an acute or severe acute respiratory infection, hypoxemic respiratory failure (HRF) and acute respiratory distress syndrome (ARDS), sepsis, and septic shock, pneumonia, the pneumonia is pneumonia COVID-2019, the simple infection comprises fever, cough, and sore throat; or the drug is provided to serve as an inhibitor for a coronavirus; or the drug is provided to inhibit a replication or a reproduction of a coronavirus in a cell, $$\text{fullerene-}RR_1R_2R_3R_4R_5 \quad \text{formula A}$$

wherein fullerene in the formula A is a cage-like all-carbon structure comprising a five-membered carbon ring, a six-membered carbon ring, and/or a seven-membered carbon ring and/or a four-membered carbon ring, or the fullerene is a metal or cluster-embedded structure;

the fullerene is selected from the group consisting of $C_{60}$, $C_{70}$, $C_{84}$, $C_{90}$, and $C_{100}$;

wherein

R is selected from the group consisting of the following:

(1) H, F, Cl, Br, I, $C_1$-$C_6$ alkyl, and $C_1$-$C_6$ alkoxy;

(2)

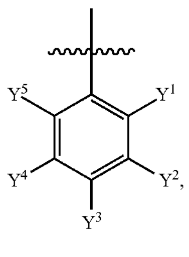

wherein $Y^1$, $Y^2$, $Y^3$, $Y^4$, and $Y^5$ are not all H and each are independently selected from the group consisting of the following:

1) H, and

2)

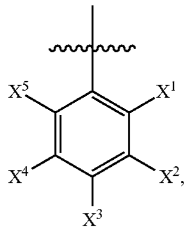

wherein $X^1$, $X^2$, $X^3$, $X^4$, and $X^5$ each are independently selected from the group consisting of H and $C_1$-$C_6$ alkyl substituted with 1, 2, or 3 carboxyl groups, and $X^1$, $X^2$, $X^3$, $X^4$, and $X^5$ are not all H; and (3)

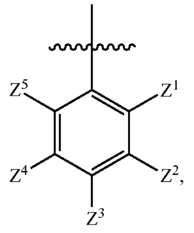

wherein $Z^1$, $Z^2$, $Z^3$, $Z^4$, and $Z^5$ each are independently selected from the group consisting of H and $C_1$-$C_6$ alkyl substituted with 1, 2, or 3 carboxyl groups, and $Z^1$, $Z^2$, $Z^3$, $Z^4$, and $Z^5$ are not all H;

$R^1$, $R^2$, $R^3$, $R^4$, and $R^5$ each are independently selected from the group consisting of the following:

(1)

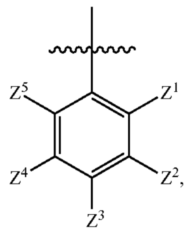

wherein $Z^1$, $Z^2$, $Z^3$, $Z^4$, and $Z^5$ each are independently selected from the group consisting of H and $C_1$-$C_6$ alkyl substituted with 1, 2, or 3 carboxyl groups, and $Z^1$, $Z^2$, $Z^3$, $Z^4$, and $Z^5$ are not all H; and (2)

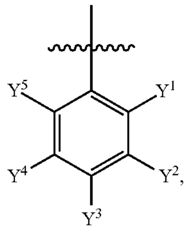

wherein $Y^1$, $Y^2$, $Y^3$, $Y^4$, and $Y^5$ are not all H and each are independently selected from the group consisting of the following:

1) H, and

2)

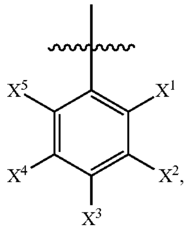

wherein $X^1$, $X^2$, $X^3$, $X^4$, and $X^5$ each are independently selected from the group consisting of H and $C_1$-$C_6$ alkyl substituted with 1, 2, or 3 carboxyl groups, and $X^1$, $X^2$, $X^3$, $X^4$, and $X^5$ are not all H.

8. The method of the use according to claim 7, wherein R is selected from the group consisting of the following:

(1) H, F, Cl, Br, I, $C_1$-$C_6$ alkyl, and $C_1$-$C_6$ alkoxy; and (2)

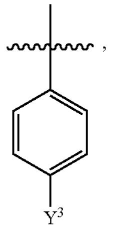

wherein $Y^3$ is

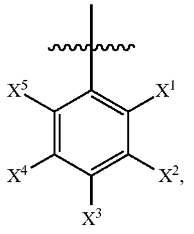

wherein $X^1$, $X^2$, $X^3$, $X^4$, and $X^5$ each are independently selected from the group consisting of H and $C_1$-$C_6$ alkyl substituted with 1, 2, or 3 carboxyl groups, and $X^1$, $X^2$, $X^3$, $X^4$, and $X^5$ are not all H;

or, $Y^3$ is

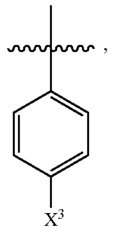

wherein $X^3$ is $C_1$-$C_6$ alkyl substituted with 1, 2, or 3 carboxyl groups; or $R^1$, $R^2$, $R^3$, $R^4$, and $R^5$ each are independently selected from the group consisting of the following:

(1)

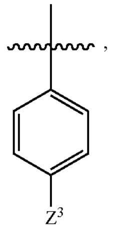

wherein $Z^3$ is independently $C_1$-$C_6$ alkyl substituted with 1, 2, or 3 carboxyl groups; and (2)

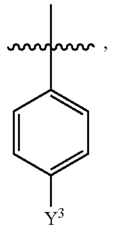

wherein $Y^3$ is

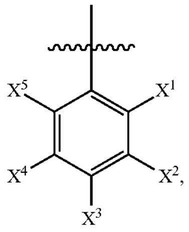

wherein $X^1$, $X^2$, $X^3$, $X^4$, and $X^5$ each are independently selected from the group consisting of H and $C_1$-$C_6$ alkyl substituted with 1, 2, or 3 carboxyl groups, and $X^1$, $X^2$, $X^3$, $X^4$, and $X^5$ are not all H;

or, $Y^3$ is

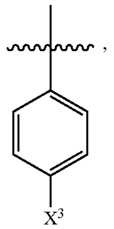

wherein $X^3$ is independently $C_1$-$C_6$ alkyl substituted with 1, 2, or 3 carboxyl groups.

9. The method of the use according to claim 7, wherein the compound shown in formula A is selected from the group consisting of the following:

| compound No. | compound structure |
|---|---|
| 1 | 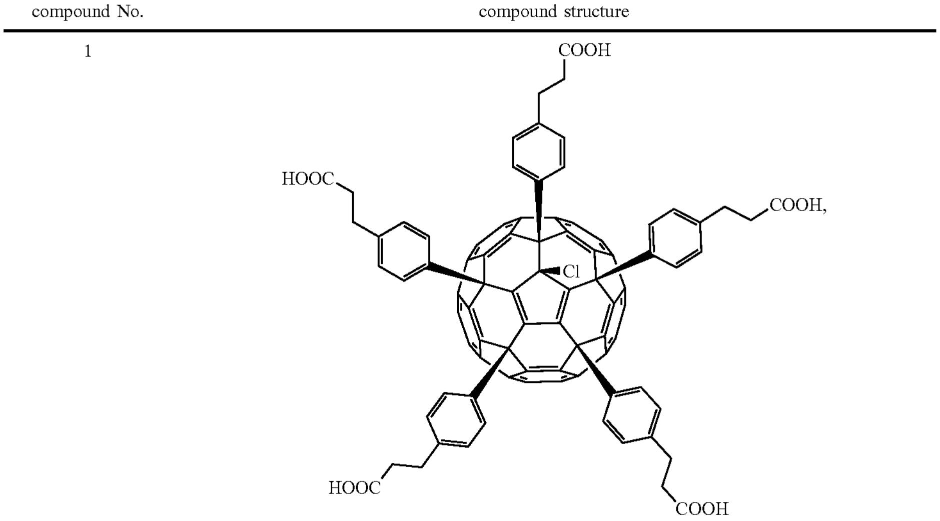, |
| 2 | 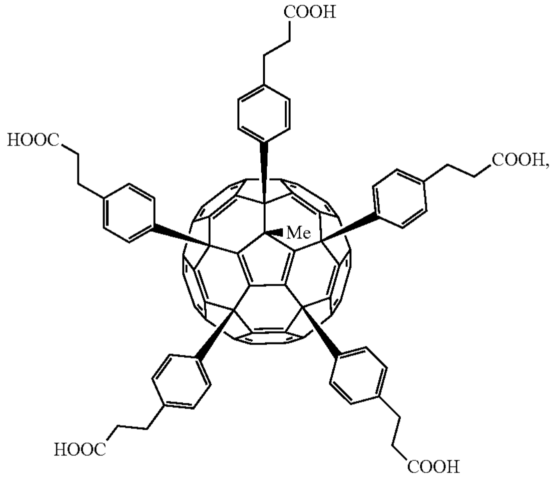, |
| 3 | 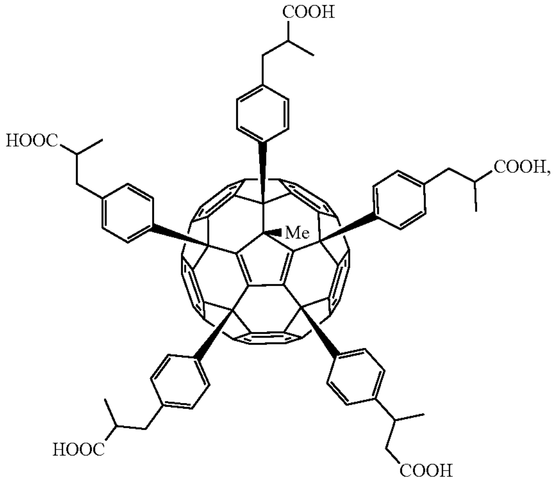, |
| 4 | 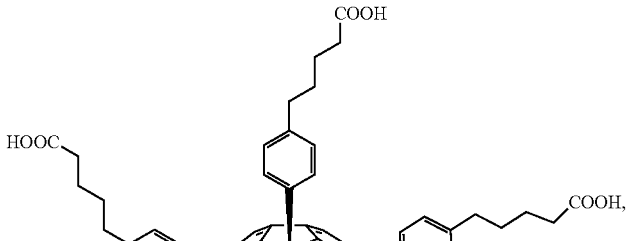, |

10. A method of a use of a pharmaceutical composition or a vesicle in a preparation of a drug, wherein the pharmaceutical composition comprises the compound shown in formula A or the stereoisomer, prodrug, pharmaceutically acceptable salt, or pharmaceutically acceptable solvate of the compound according to claim 7 and an optional pharmaceutically acceptable carrier or excipient; the vesicle has a diameter of 40 nm to 140 nm and is produced using the compound shown in formula A or the pharmaceutically acceptable salt of the compound;

the drug is provided for preventing and/or treating a disease caused by a coronavirus infection, the disease is a respiratory disease comprising a simple infection, pneumonia, an acute or severe acute respiratory infection, hypoxemic respiratory failure (RF) and acute respiratory distress syndrome (ARDS), sepsis, and septic shock, the pneumonia is pneumonia COVID-2019 the simple infection comprises fever, cough, and sore throat; or the drug is provided to serve as an inhibitor for a coronavirus; or the drug is provided to inhibit a replication or a reproduction of a coronavirus in a cell;

the pharmaceutical composition is in a dosage form of a pill, a tablet, a capsule, an aqueous solution, or an aqueous suspension for an oral administration, in a dosage form of a micronized suspension or solution for a topical ocular administration, in a dosage form of a paste, an ointment, a lotion, a spray, or a cream for a topical transdermal or mucosal administration, or in a dosage form of sterile injection water, an oil suspension, or a sterile injection solution for an injection; and the vesicle is produced by a method comprising: dissolving the compound shown in formula A or the pharmaceutically acceptable salt of the compound in DMF or acetonitrile to obtain a solution, and subjecting the solution to an ultrasonic treatment at 30° C. to 40° C. for 1 h to 2 h to obtain the vesicle, wherein a ratio of a mass of the compound shown in formula A or the pharmaceutically acceptable salt of the compound to a volume of the DMF or the acetonitrile is 1 mg:1 mL.

11. The compound according to claim 1, wherein the fullerene is $C_{60}$ having a general formula shown in formula I, and the fullerene is a hollow cage-like structure;

formula I

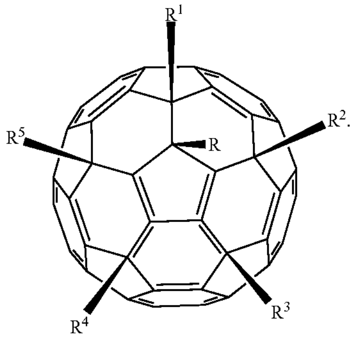

12. The compound according to claim 1, wherein R is selected from the group consisting of the following:

(1) H, F, Cl, Br, I, $C_1$-$C_6$ alkyl, and $C_1$-$C_6$ alkoxy; and (2)

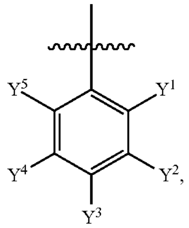

wherein $Y^1$, $Y^2$, $Y^3$, $Y^4$, and $Y^5$ are not all H and each are independently selected from the group consisting of the following:

1) H, and

2)

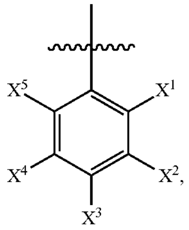

wherein $X^1$, $X^2$, $X^3$, $X^4$, and $X^5$ each are independently selected from the group consisting of H and $C_1$-$C_6$ alkyl substituted with 1, 2, or 3 carboxyl groups, and $X^1$, $X^2$, $X^3$, $X^4$, and $X^5$ are not all H.

13. The compound according to claim 2, wherein the compound is a compound selected from the group consisting of the following:

| compound No. | compound structure |
|---|---|
| 3 | 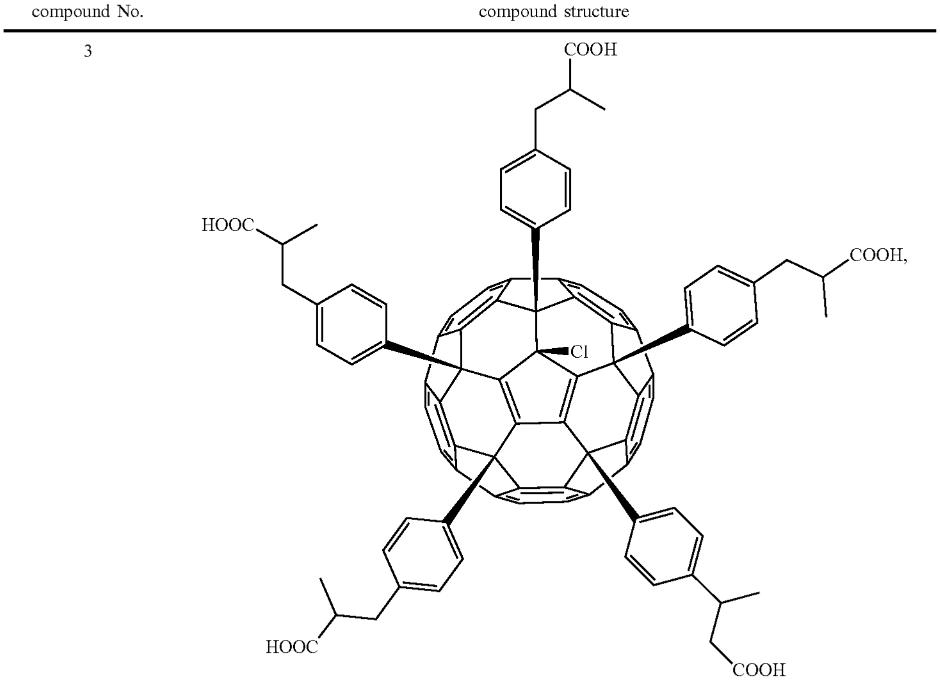, |
| 4 | 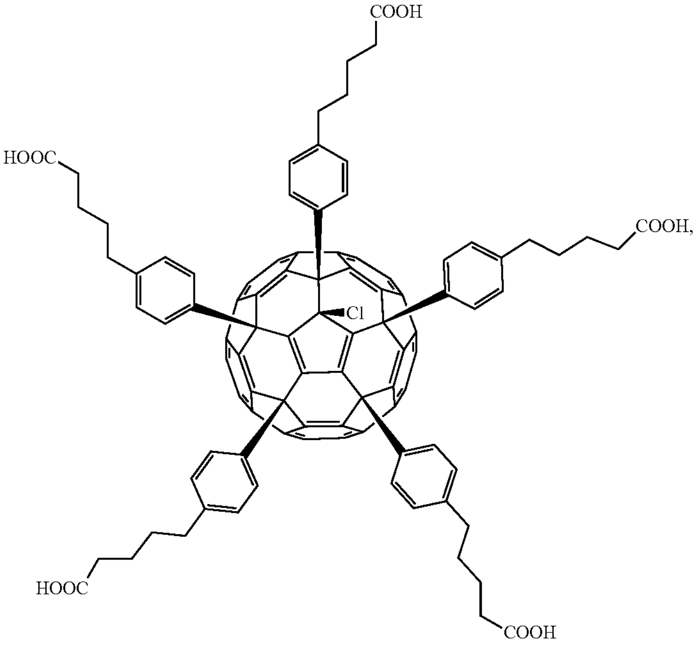, |
| 5 | 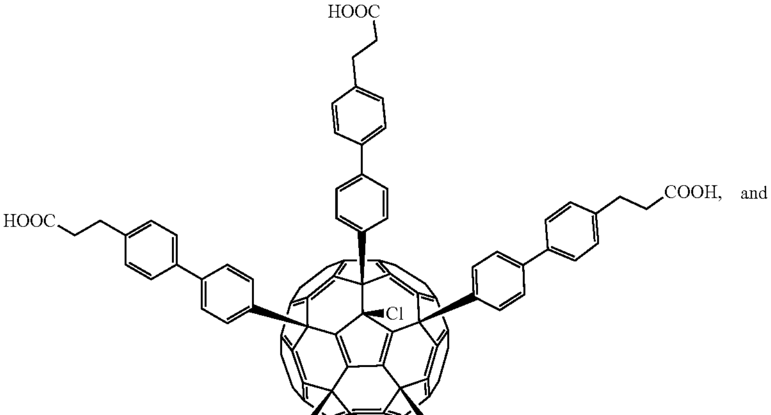, and |

or a stereoisomer, prodrug, pharmaceutically acceptable salt, or pharmaceutically acceptable solvate of the compound 3, the compound 4, the compound 5, or the compound 6.

14. The method according to claim 4, wherein after step (2) and before step (3), the method further comprises: washing and drying the first filter cake; and after step (5), the method further comprises: drying the second filter cake to obtain the compound.

15. The pharmaceutical composition according to claim 5, wherein in the compound, R is selected from the group consisting of the following:

(1) H, F, Cl, Br, I, $C_1$-$C_6$ alkyl, and $C_1$-$C_6$ alkoxy; and (2)

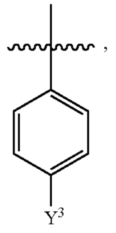

wherein $Y^3$ is

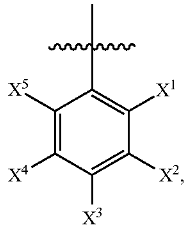

wherein $X^1$, $X^2$, $X^3$, $X^4$, and $X^5$ each are independently selected from the group consisting of H and $C_1$-$C_6$ alkyl substituted with 1, 2, or 3 carboxyl groups, and $X^1$, $X^2$, $X^3$, $X^4$, and $X^5$ are not all H;

or, $Y^3$ is

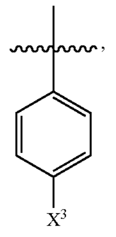

wherein $X^3$ is $C_1$-$C_6$ alkyl substituted with 1, 2, or 3 carboxyl groups; or $R^1$, $R^2$, $R^3$, $R^4$, and $R^5$ each are independently selected from the group consisting of the following:

(1)

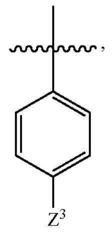

wherein $Z^3$ is independently $C_1$-$C_6$ alkyl substituted with 1, 2, or 3 carboxyl groups; and (2)

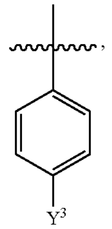

wherein $Y^3$ is

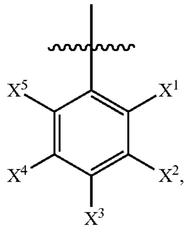

wherein $X^1$, $X^2$, $X^3$, $X^4$, and $X^5$ each are independently selected from the group consisting of H and $C_1$-$C_6$ alkyl substituted with 1, 2, or 3 carboxyl groups, and $X^1$, $X^2$, $X^3$, $X^4$, and $X^5$ are not all H;

or, $Y^3$ is

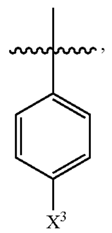

wherein $X^3$ is independently $C_1$-$C_6$ alkyl substituted with 1, 2, or 3 carboxyl groups.

16. The pharmaceutical composition according to claim 5, wherein the compound is a compound selected from the group consisting of the following:

| compound No. | compound structure |
| --- | --- |
| 3 | 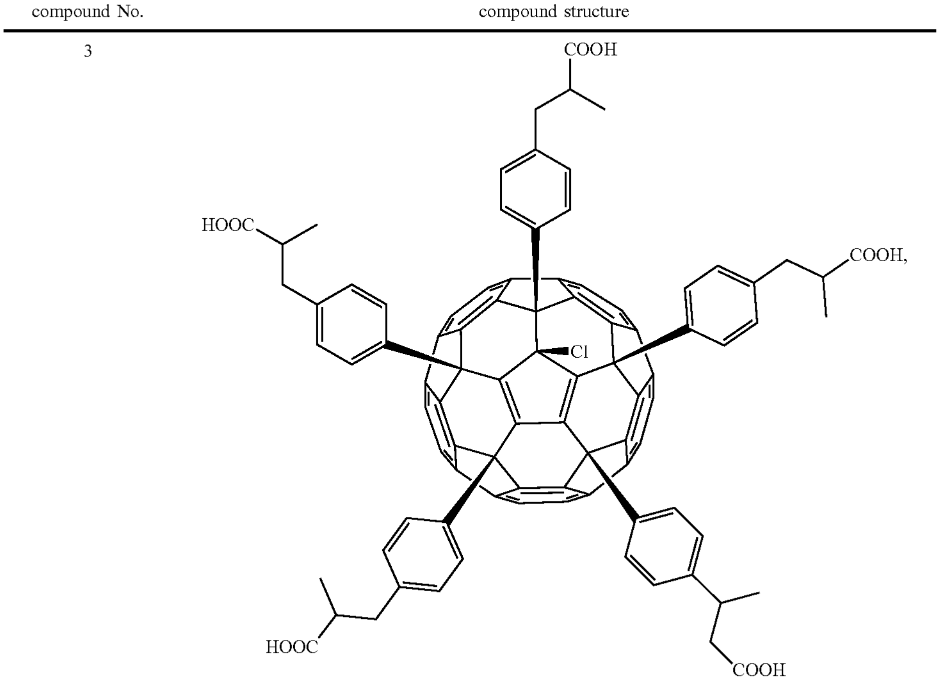 |
| 4 | 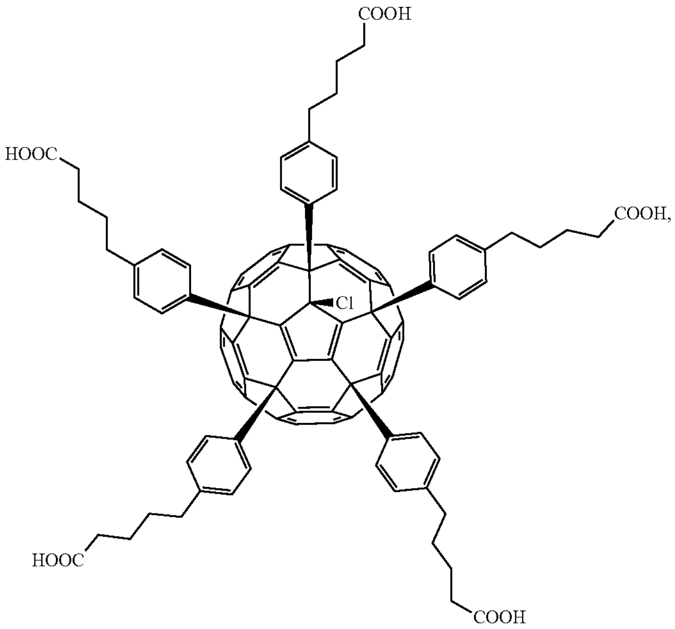 |
| 5 | 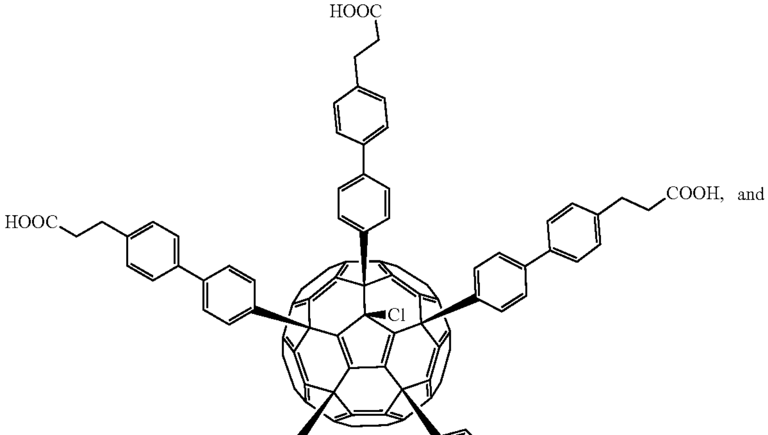 and |

or a stereoisomer, prodrug, pharmaceutically acceptable salt, or pharmaceutically acceptable solvate of the compound 3, the compound 4, the compound 5, or the compound 6.

17. The vesicle according to claim 6, wherein in the compound, R is selected from the group consisting of the following:

(1) H, F, Cl, Br, I, $C_1$-$C_6$ alkyl, and $C_1$-$C_6$ alkoxy; and (2)

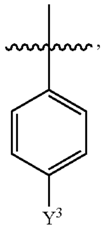

wherein $Y^3$ is

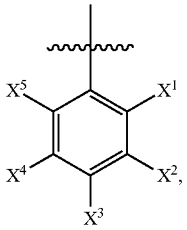

wherein $X^1$, $X^2$, $X^3$, $X^4$, and $X^5$ each are independently selected from the group consisting of H and $C_1$-$C_6$ alkyl substituted with 1, 2, or 3 carboxyl groups, and $X^1$, $X^2$, $X^3$, $X^4$, and $X^5$ are not all H;

or, $Y^3$ is

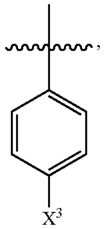

wherein $X^3$ is $C_1$-$C_6$ alkyl substituted with 1, 2, or 3 carboxyl groups; or $R^1$, $R^2$, $R^3$, $R^4$, and $R^5$ each are independently selected from the group consisting of the following:

(1)

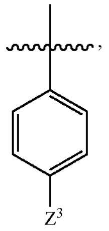

wherein $Z^3$ is independently $C_1$-$C_6$ alkyl substituted with 1, 2, or 3 carboxyl groups; and (2)

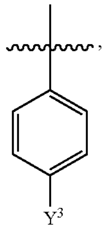

wherein $Y^3$ is

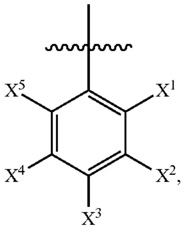

wherein $X^1$, $X^2$, $X^3$, $X^4$, and $X^5$ each are independently selected from the group consisting of H and $C_1$-$C_6$ alkyl substituted with 1, 2, or 3 carboxyl groups, and $X^1$, $X^2$, $X^3$, $X^4$, and $X^5$ are not all H;

or, $Y^3$ is

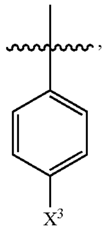

wherein $X^3$ is independently $C_1$-$C_6$ alkyl substituted with 1, 2, or 3 carboxyl groups.

18. The vesicle according to claim 6, wherein the compound is a compound selected from the group consisting of the following:

| compound No. | compound structure |
| --- | --- |
| 3 | 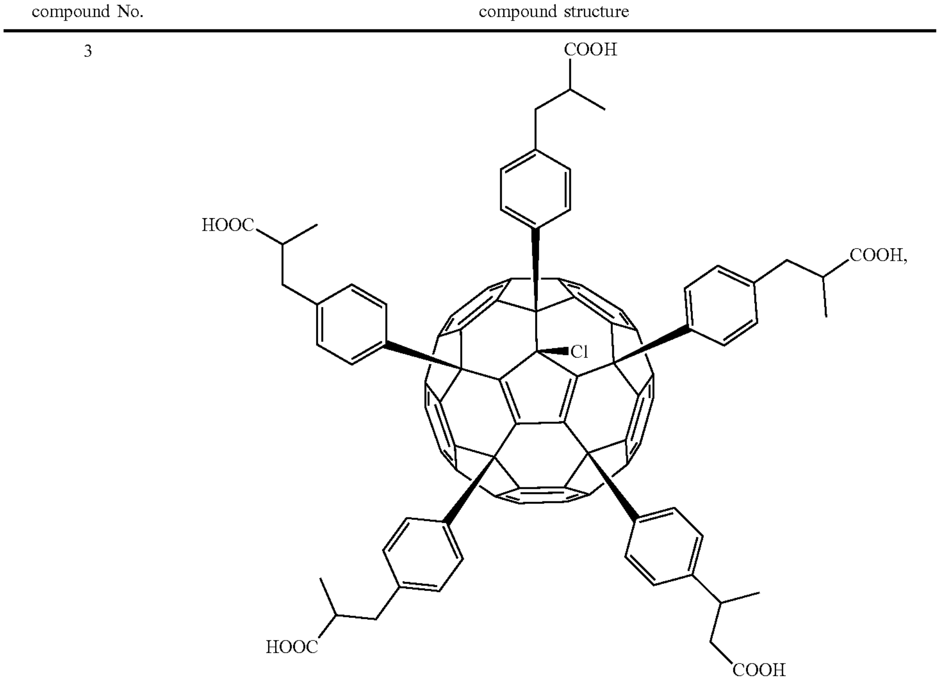 |
| 4 | 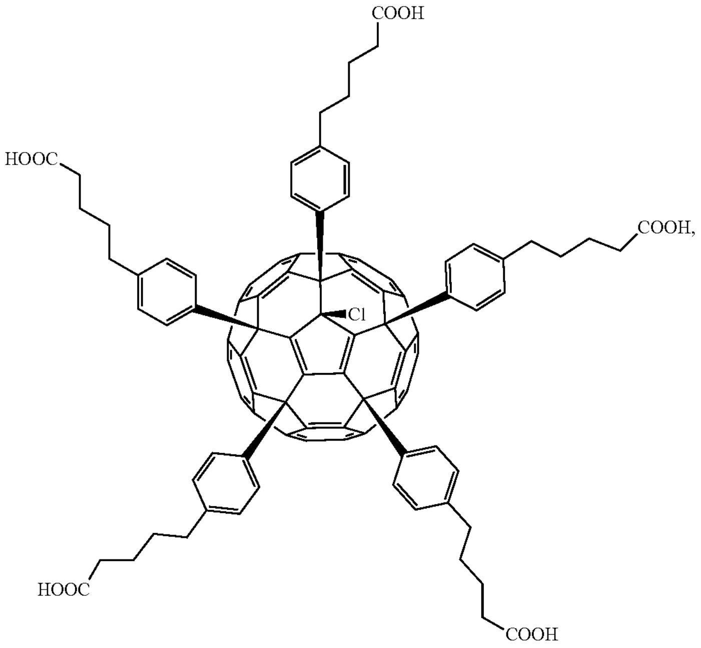 |
| 5 | 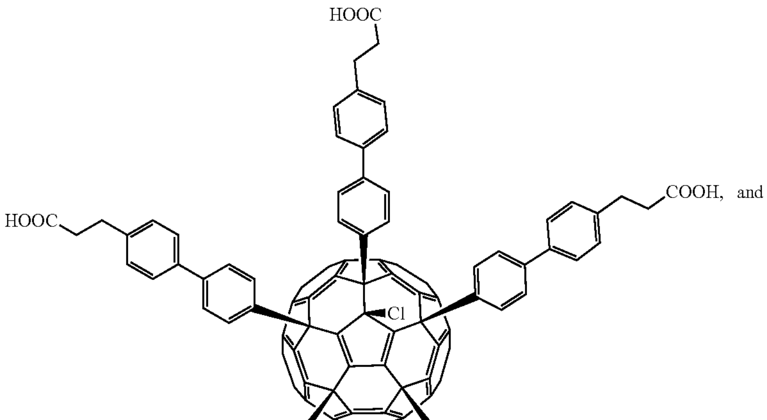 and |

or a stereoisomer, prodrug, pharmaceutically acceptable salt, or pharmaceutically acceptable solvate of the compound 3, the compound 4, the compound 5, or the compound 6.

19. The method of the use according to claim 7, wherein the fullerene is $C_{60}$ having a general formula shown in formula I, and the fullerene is a hollow cage-like structure;

formula I

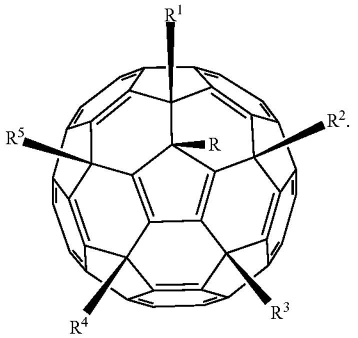

20. The method of the use according to claim 7, wherein R is selected from the group consisting of the following:

(1) H, F, Cl, Br, I, $C_1$-$C_6$ alkyl, and $C_1$-$C_6$ alkoxy; and (2)

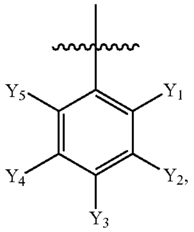

wherein $Y^1$, $Y^2$, $Y^3$, $Y^4$, and $Y^5$ are not all H and each are independently selected from the group consisting of the following:

1) H, and

2)

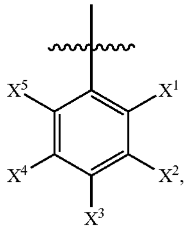

wherein $X^1$, $X^2$, $X^3$, $X^4$, and $X^5$ each are independently selected from the group consisting of H and $C_1$-$C_6$ alkyl substituted with 1, 2, or 3 carboxyl groups, and $X^1$, $X^2$, $X^3$, $X^4$, and $X^5$ are not all H.

* * * * *